United States Patent
Alargova et al.

(10) Patent No.: US 10,058,546 B2
(45) Date of Patent: *Aug. 28, 2018

(54) PHARMACEUTICAL COMPOSITIONS OF (R)-1-(2,2-DIFLUOROBENZO[D][1,3]DIOXOL-5-Y1)-N-(1-(2,3-DIHYDROXYPROPY1)-6-FLUORO-2-(1-HYDROXY-2-METHYLPROPAN-2-Y1)-1H-INDOL-5-Y1) CYCLOPROPANECARBOX-AMIDE AND ADMINISTRATION THEREOF

(71) Applicant: Vertex Pharmaceuticals Incorporated, Boston, MA (US)

(72) Inventors: Rossitza Gueorguieva Alargova, Brighton, MA (US); Craig Antony Dunbar, Needham, MA (US); Irina Nikolaevna Kadiyala, Newton, MA (US)

(73) Assignee: Vertex Pharmaceuticals Incorporated, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/342,999

(22) Filed: Nov. 3, 2016

(65) Prior Publication Data

US 2017/0266176 A1  Sep. 21, 2017

Related U.S. Application Data

(63) Continuation of application No. 14/656,043, filed on Mar. 12, 2015, now abandoned, which is a continuation of application No. 13/942,617, filed on Jul. 15, 2013, now Pat. No. 9,012,496.

(60) Provisional application No. 61/822,781, filed on May 13, 2013, provisional application No. 61/671,932, filed on Jul. 16, 2012.

(51) Int. Cl.
| | | |
|---|---|---|
| A61K 31/47 | (2006.01) | |
| A61K 31/36 | (2006.01) | |
| A61K 45/06 | (2006.01) | |
| A61K 31/404 | (2006.01) | |
| A61K 9/20 | (2006.01) | |
| A61K 9/16 | (2006.01) | |

(52) U.S. Cl.
CPC ............ *A61K 31/47* (2013.01); *A61K 9/1652* (2013.01); *A61K 9/2054* (2013.01); *A61K 31/404* (2013.01); *A61K 45/06* (2013.01); *A61K 31/36* (2013.01); *Y10S 514/851* (2013.01)

(58) Field of Classification Search
CPC ................................. A61K 31/36; A61K 31/47
USPC ........................................ 514/311, 464, 851
See application file for complete search history.

(56) References Cited

U.S. PATENT DOCUMENTS

| | | |
|---|---|---|
| 4,138,397 A | 2/1979 | Böhme |
| 5,304,121 A | 4/1994 | Sahatjian |
| 5,886,026 A | 3/1999 | Hunter et al. |
| 6,099,562 A | 8/2000 | Ding et al. |
| 6,426,331 B1 | 7/2002 | McKinney et al. |
| 6,479,483 B2 | 11/2002 | Bös et al. |
| 6,770,637 B2 | 8/2004 | Godel et al. |
| 6,777,400 B2 | 8/2004 | Biggadike et al. |
| 6,992,096 B2 | 1/2006 | Karp et al. |
| 7,202,262 B2 | 4/2007 | Karp et al. |
| 7,304,080 B2 | 12/2007 | Karp et al. |
| 7,407,976 B2 | 8/2008 | Miller et al. |
| 7,419,991 B2 | 9/2008 | Karp et al. |
| 7,495,103 B2 | 2/2009 | Hadida-Ruah et al. |
| 7,553,855 B2 | 6/2009 | Young et al. |
| 7,582,665 B2 | 9/2009 | Takemoto et al. |
| 7,598,412 B2 | 10/2009 | Hadida Ruah et al. |
| 7,645,789 B2 | 1/2010 | Hadida Ruah et al. |
| 7,659,268 B2 | 2/2010 | Hadida-Ruah et al. |
| 7,671,221 B2 | 3/2010 | Hadida Ruah et al. |
| 7,691,902 B2 | 4/2010 | Hadida Ruah et al. |
| 7,728,023 B2 | 6/2010 | Takeuchi et al. |
| 7,741,321 B2 | 6/2010 | Hadida Ruah et al. |
| 7,754,739 B2 | 7/2010 | Hadida Ruah et al. |
| 7,772,259 B2 | 8/2010 | Karp et al. |
| 7,776,905 B2 | 8/2010 | Hadida Ruah et al. |
| 7,846,951 B2 | 12/2010 | Miller et al. |
| 7,893,094 B2 | 2/2011 | Pollard et al. |
| 7,906,516 B2 | 3/2011 | Tsaklakidis et al. |
| 7,956,052 B2 | 6/2011 | Hadida Ruah et al. |
| 7,973,038 B2 | 7/2011 | Hadida Ruah et al. |
| 7,973,169 B2 | 7/2011 | Hadida Ruah et al. |
| 7,977,322 B2 | 7/2011 | Ruah et al. |
| 7,999,113 B2 | 8/2011 | Hadida-Ruah et al. |

(Continued)

FOREIGN PATENT DOCUMENTS

| | | |
|---|---|---|
| CN | 1512987 A | 7/2004 |
| CN | 1898221 A | 1/2007 |

(Continued)

OTHER PUBLICATIONS

Aridor, M. and W.E. Balch (1999) "Integration of endoplasmic reticulum signaling in health and disease" *Nature Med*, 5(7):745-751.

(Continued)

*Primary Examiner* — Kevin E Weddington
(74) *Attorney, Agent, or Firm* — Finnegan, Henderson, Farabow, Garrett & Dunner, LLP

(57) ABSTRACT

A pharmaceutical composition comprising Compound 1, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, and at least one excipient selected from: a filler, a disintegrant, a surfactant, a glidant and a lubricant, the composition being suitable for oral administration to a patient in need thereof to treat a CFTR mediated disease such as Cystic Fibrosis. Methods for treating a patient in need thereof include administering the pharmaceutical composition of Compound 1 are also disclosed.

14 Claims, 17 Drawing Sheets

(56) References Cited

U.S. PATENT DOCUMENTS

| | | |
|---|---|---|
| 8,012,999 B2 | 9/2011 | Hadida Ruah et al. |
| 8,039,491 B2 | 10/2011 | Hadida Ruah et al. |
| 8,076,357 B2 | 12/2011 | Young et al. |
| 8,101,767 B2 | 1/2012 | Ruah et al. |
| 8,124,781 B2 | 2/2012 | Siesel |
| 8,163,772 B2 | 4/2012 | DeMattei et al. |
| 8,188,283 B2 | 5/2012 | Binch et al. |
| 8,227,615 B2 | 7/2012 | Hadida-Ruah et al. |
| 8,232,302 B2 | 7/2012 | Miller et al. |
| 8,242,149 B2 | 8/2012 | Ruah et al. |
| 8,299,099 B2 | 10/2012 | Ruah et al. |
| 8,314,239 B2 | 11/2012 | Binch et al. |
| 8,314,256 B2 | 11/2012 | Ruah et al. |
| 8,318,733 B2 | 11/2012 | Hadida-Ruah et al. |
| 8,324,207 B2 | 12/2012 | Hadida Ruah et al. |
| 8,324,242 B2 | 12/2012 | Ruah et al. |
| 8,344,147 B2 | 1/2013 | Ambhaikar et al. |
| 8,354,427 B2 | 1/2013 | Van Goor |
| 8,362,253 B2 | 1/2013 | DeMattei et al. |
| 8,367,660 B2 | 2/2013 | Binch et al. |
| 8,389,727 B2 | 3/2013 | Zhang et al. |
| 8,399,479 B2 | 3/2013 | Binch et al. |
| 8,404,849 B2 | 3/2013 | Sun et al. |
| 8,404,865 B2 | 3/2013 | Ambhaikar et al. |
| 8,410,132 B2 | 4/2013 | Binch et al. |
| 8,410,274 B2 | 4/2013 | Hurter et al. |
| 8,415,387 B2 | 4/2013 | Ruah et al. |
| 8,431,605 B2 | 4/2013 | Hadida Ruah et al. |
| 8,436,014 B2 | 5/2013 | Zhang et al. |
| 8,461,156 B2 | 6/2013 | Hadida Ruah et al. |
| 8,461,342 B2 | 6/2013 | Siesel |
| 8,461,352 B2 | 6/2013 | Ambhaikar et al. |
| 8,471,029 B2 | 6/2013 | Arekar et al. |
| 8,476,442 B2 | 7/2013 | DeMattei et al. |
| 8,507,524 B2 | 8/2013 | Ruah et al. |
| 8,507,534 B2 | 8/2013 | Keshavarz-Shokri et al. |
| 8,507,687 B2 | 8/2013 | Keshavarz-Shokri et al. |
| 8,513,282 B2 | 8/2013 | Binch et al. |
| 8,524,767 B2 | 9/2013 | Miller et al. |
| 8,524,910 B2 | 9/2013 | Hadida Ruah et al. |
| 8,541,453 B2 | 9/2013 | Hadida-Ruah et al. |
| 8,552,006 B2 | 10/2013 | Binch et al. |
| 8,552,034 B2 | 10/2013 | Verwijs et al. |
| 8,563,573 B2 | 10/2013 | Ruah et al. |
| 8,563,593 B2 | 10/2013 | Alargova et al. |
| 8,575,209 B2 | 11/2013 | Ruah et al. |
| 8,586,615 B2 | 11/2013 | Hadida-Ruah et al. |
| 8,592,602 B2 | 11/2013 | Siesel |
| 8,598,181 B2 | 12/2013 | Hadida Ruah et al. |
| 8,598,205 B2 | 12/2013 | Binch et al. |
| 8,604,203 B2 | 12/2013 | Binch et al. |
| 8,609,703 B2 | 12/2013 | Ruah et al. |
| 8,614,325 B2 | 12/2013 | Yang et al. |
| 8,614,327 B2 | 12/2013 | Sheth et al. |
| 8,623,894 B2 | 1/2014 | DeMattei et al. |
| 8,623,905 B2 | 1/2014 | Ruah et al. |
| 8,629,162 B2 | 1/2014 | Hadida-Ruah et al. |
| 8,633,189 B2 | 1/2014 | Binch et al. |
| 8,642,609 B2 | 2/2014 | Makings et al. |
| 8,653,103 B2 | 2/2014 | Keshavarz-Shokri et al. |
| 8,674,108 B2 | 3/2014 | Luisi et al. |
| 8,710,075 B2 | 4/2014 | Binch et al. |
| 8,716,338 B2 | 5/2014 | Young |
| 8,722,704 B2 | 5/2014 | Hadida Ruah et al. |
| 8,741,922 B2 | 6/2014 | Zhang et al. |
| 8,741,925 B2 | 6/2014 | Hadida-Ruah et al. |
| 8,741,933 B2 | 6/2014 | Hadida Ruah et al. |
| 8,741,939 B2 | 6/2014 | Hadida Ruah et al. |
| 8,742,122 B2 | 6/2014 | Keshavarz-Shokri et al. |
| 8,748,612 B2 | 6/2014 | Binch et al. |
| 8,754,222 B2 | 6/2014 | Ambhaikar et al. |
| 8,754,224 B2 | 6/2014 | Hurter et al. |
| 8,759,335 B2 | 6/2014 | Hadida Ruah et al. |
| 8,765,957 B2 | 7/2014 | DeMattei et al. |
| 8,785,476 B2 | 7/2014 | Arekar et al. |
| 8,785,640 B2 | 7/2014 | Binch et al. |
| 8,796,308 B2 | 8/2014 | Yang et al. |
| 8,796,312 B2 | 8/2014 | Hadida Ruah et al. |
| 8,802,700 B2 | 8/2014 | Sheth et al. |
| 8,802,844 B2 | 8/2014 | Gallardo-Godoy |
| 8,802,868 B2 | 8/2014 | Keshavarz-Shokri et al. |
| 8,816,093 B2 | 8/2014 | Siesel |
| 8,822,451 B2 | 9/2014 | Ruah et al. |
| 8,829,204 B2 | 9/2014 | Hadida-Ruah et al. |
| 8,835,639 B2 | 9/2014 | DeMattei et al. |
| 8,846,718 B2 | 9/2014 | Keshavarz-Shokri et al. |
| 8,846,753 B2 | 9/2014 | Hadida Ruah et al. |
| 8,853,254 B2 | 10/2014 | Hadida Ruah et al. |
| 8,853,415 B2 | 10/2014 | Hadida Ruah et al. |
| 8,883,206 B2 | 11/2014 | Doukou et al. |
| 8,884,018 B2 | 11/2014 | Ambhaikar et al. |
| 8,889,875 B2 | 11/2014 | Ruah et al. |
| 8,912,199 B2 | 12/2014 | Hadida Ruah et al. |
| 8,952,049 B2 | 2/2015 | Ruah et al. |
| 8,952,050 B2 | 2/2015 | Ruah et al. |
| 8,962,856 B2 | 2/2015 | Hadida-Ruah et al. |
| 8,969,382 B2 | 3/2015 | Binch et al. |
| 8,969,386 B2 | 3/2015 | Hadida-Ruah et al. |
| 8,969,574 B2 | 3/2015 | Keshavarz-Shokri et al. |
| 8,993,600 B2 | 3/2015 | Hadida Ruah et al. |
| 8,999,976 B2 | 4/2015 | Binch et al. |
| 9,012,473 B2 | 4/2015 | Hadida Ruah et al. |
| 9,012,496 B2 | 4/2015 | Alargova et al. |
| 9,012,652 B2 | 4/2015 | Siesel |
| 9,035,072 B2 | 5/2015 | Belmont et al. |
| 9,045,425 B2 | 6/2015 | Luisi et al. |
| 9,051,303 B2 | 6/2015 | Keshavarz-Shokri et al. |
| 9,051,324 B2 | 6/2015 | Binch et al. |
| 9,079,916 B2 | 7/2015 | Hadida Ruah et al. |
| 9,090,619 B2 | 7/2015 | Hadida-Ruah et al. |
| 9,102,672 B2 | 8/2015 | Hadida-Ruah et al. |
| 9,127,162 B2 | 9/2015 | Harders et al. |
| 9,139,530 B2 | 9/2015 | Hurter et al. |
| 9,150,552 B2 | 10/2015 | Keshavarz-Shokri et al. |
| 9,192,606 B2 | 11/2015 | Young |
| 9,216,969 B2 | 12/2015 | Ruah et al. |
| 9,241,934 B2 | 1/2016 | Verwijs et al. |
| 9,249,131 B2 | 2/2016 | Hadida Ruah et al. |
| 9,254,291 B2 | 2/2016 | Looker et al. |
| 9,314,455 B2 | 4/2016 | Keshavarz-Shokri et al. |
| 9,321,725 B2 | 4/2016 | Miller et al. |
| 9,351,962 B2 | 5/2016 | Hadida Ruah et al. |
| 9,371,287 B2 | 6/2016 | DeMattei et al. |
| 9,399,648 B2 | 7/2016 | Gallardo-Godoy |
| 9,434,717 B2 | 9/2016 | Keshavarz-Shokri et al. |
| 9,504,683 B2 | 11/2016 | Hadida Ruah et al. |
| 9,522,145 B2 | 12/2016 | Hadida Ruah et al. |
| 9,550,761 B2 | 1/2017 | Hadida-Ruah et al. |
| 9,670,163 B2 | 6/2017 | Hurter et al. |
| 9,701,639 B2 | 7/2017 | Strohmeier et al. |
| 9,732,080 B2 | 8/2017 | Hadida-Ruah et al. |
| 9,751,839 B2 | 9/2017 | DeMattei et al. |
| 9,751,890 B2 | 9/2017 | Hadida Ruah et al. |
| 9,758,510 B2 | 9/2017 | Hadida Ruah et al. |
| 9,776,968 B2 | 10/2017 | Siesel |
| 9,840,499 B2 | 12/2017 | Keshavarz-Shokri et al. |
| 2003/0125315 A1 | 7/2003 | Mjalli et al. |
| 2003/0219489 A1 | 11/2003 | Curatolo et al. |
| 2004/0105820 A1 | 6/2004 | Weers et al. |
| 2005/0070718 A1 | 3/2005 | Lubisch et al. |
| 2005/0113423 A1 | 5/2005 | Van Goor et al. |
| 2005/0164973 A1 | 7/2005 | Karp et al. |
| 2005/0215614 A1 | 9/2005 | Singh et al. |
| 2005/0222271 A1 | 10/2005 | Huang |
| 2006/0003005 A1 | 1/2006 | Cao et al. |
| 2006/0004010 A1 | 1/2006 | Habashita et al. |
| 2006/0035943 A1 | 2/2006 | Karp et al. |
| 2006/0148863 A1 | 7/2006 | Karp et al. |
| 2006/0148864 A1 | 7/2006 | Karp et al. |
| 2006/0217448 A1 | 9/2006 | Kelly et al. |
| 2007/0099938 A1 | 5/2007 | Ohmoto et al. |
| 2007/0218138 A1 | 9/2007 | Bittorf et al. |
| 2008/0081814 A1 | 4/2008 | Cezanne et al. |
| 2008/0097083 A1 | 4/2008 | Cho et al. |

(56) References Cited

U.S. PATENT DOCUMENTS

| | | |
|---|---|---|
| 2008/0132560 A1 | 6/2008 | Chow et al. |
| 2008/0138803 A1 | 6/2008 | Galvan-Goldman (nee Galvan) et al. |
| 2008/0260820 A1 | 10/2008 | Borrelly et al. |
| 2009/0105272 A1 | 4/2009 | Grootenhuis et al. |
| 2009/0176839 A1 | 7/2009 | Keshavarz-Shokri et al. |
| 2009/0246820 A1 | 10/2009 | Singh et al. |
| 2009/0270465 A1 | 10/2009 | Albright et al. |
| 2010/0036130 A1 | 2/2010 | Siesel |
| 2010/0074949 A1 | 3/2010 | Rowe et al. |
| 2010/0125090 A1 | 5/2010 | Hadida Ruah et al. |
| 2010/0144798 A1 | 6/2010 | Van Goor et al. |
| 2010/0256184 A1 | 10/2010 | Rowe et al. |
| 2011/0064811 A1 | 3/2011 | Hurter et al. |
| 2011/0098311 A1 | 4/2011 | Van Goor et al. |
| 2011/0098484 A1 | 4/2011 | Saitoh et al. |
| 2011/0123449 A1 | 5/2011 | Zhang et al. |
| 2011/0177999 A1 | 7/2011 | Singh et al. |
| 2011/0251253 A1 | 10/2011 | Keshavarz-Shokri et al. |
| 2011/0257223 A1 | 10/2011 | Goor et al. |
| 2011/0288122 A1 | 11/2011 | Van Goor et al. |
| 2012/0035179 A1 | 2/2012 | Hadida-Ruah et al. |
| 2012/0046330 A1 | 2/2012 | Alargova et al. |
| 2012/0064157 A1 | 3/2012 | Doukou et al. |
| 2012/0122921 A1 | 5/2012 | DeMattei et al. |
| 2012/0122922 A1 | 5/2012 | Young et al. |
| 2012/0184583 A1 | 7/2012 | Van Goor et al. |
| 2012/0220625 A1 | 8/2012 | Rowe et al. |
| 2012/0232059 A1 | 9/2012 | Hadida-Ruah et al. |
| 2012/0258983 A1 | 10/2012 | Rowe et al. |
| 2013/0012536 A1 | 1/2013 | Hadida Ruah et al. |
| 2013/0018071 A1 | 1/2013 | Arekar et al. |
| 2013/0085158 A1 | 4/2013 | Keshavarz-Shokri et al. |
| 2013/0090354 A1 | 4/2013 | Van Goor et al. |
| 2013/0095181 A1 | 4/2013 | Verwijs et al. |
| 2013/0131107 A1 | 5/2013 | Van Goor et al. |
| 2013/0143919 A1 | 6/2013 | Van Goor et al. |
| 2013/0158071 A1 | 6/2013 | Van Goor et al. |
| 2013/0178496 A1 | 7/2013 | Binch et al. |
| 2013/0184276 A1 | 7/2013 | Hadida Ruah et al. |
| 2013/0186801 A1 | 7/2013 | Verwijs et al. |
| 2013/0196983 A1 | 8/2013 | Binch et al. |
| 2013/0224293 A1 | 8/2013 | Dokou et al. |
| 2013/0231364 A1 | 9/2013 | Binch et al. |
| 2013/0231368 A1 | 9/2013 | Zhang et al. |
| 2013/0245010 A1 | 9/2013 | Hadida Ruah et al. |
| 2013/0245011 A1 | 9/2013 | Hadida Ruah et al. |
| 2013/0303484 A1 | 11/2013 | Grootenhuis et al. |
| 2013/0331567 A1 | 12/2013 | Hadida-Ruah et al. |
| 2014/0023706 A1 | 1/2014 | Verwijs et al. |
| 2014/0094499 A1 | 4/2014 | Alargova et al. |
| 2014/0112988 A1 | 4/2014 | Rowe et al. |
| 2014/0121208 A1 | 5/2014 | Van Goor et al. |
| 2014/0142138 A1 | 5/2014 | Van Goor et al. |
| 2014/0155431 A1 | 6/2014 | Hadida-Ruah et al. |
| 2014/0155626 A1 | 6/2014 | Hadida-Ruah et al. |
| 2014/0163011 A1 | 6/2014 | Hadida-Ruah et al. |
| 2014/0163068 A1 | 6/2014 | Verwijs et al. |
| 2014/0221424 A1 | 8/2014 | Zha |
| 2014/0235668 A1 | 8/2014 | Binch et al. |
| 2014/0243289 A1 | 8/2014 | Grootenhuis et al. |
| 2014/0303204 A1 | 10/2014 | Binch et al. |
| 2014/0303205 A1 | 10/2014 | Yang et al. |
| 2014/0315948 A1 | 10/2014 | Rowe et al. |
| 2014/0323521 A1 | 10/2014 | Van Goor et al. |
| 2014/0329855 A1 | 11/2014 | Arekar et al. |
| 2014/0336393 A1 | 11/2014 | Ambhaikar et al. |
| 2014/0343098 A1 | 11/2014 | Sheth et al. |
| 2014/0350281 A1 | 11/2014 | DeMattei et al. |
| 2015/0010628 A1 | 1/2015 | Dokou et al. |
| 2015/0024047 A1 | 1/2015 | Dokou et al. |
| 2015/0031722 A1 | 1/2015 | Hadida-Ruah et al. |
| 2015/0065487 A1 | 3/2015 | Hadida-Ruah et al. |
| 2015/0065497 A1 | 3/2015 | Hadida-Ruah et al. |
| 2015/0065500 A1 | 3/2015 | Hadida-Ruah et al. |
| 2015/0080431 A1 | 3/2015 | Van Goor et al. |
| 2015/0094304 A1 | 4/2015 | Ruah et al. |
| 2015/0119441 A1 | 4/2015 | Hadida Ruah et al. |
| 2015/0141459 A1 | 5/2015 | Van Goor et al. |
| 2015/0150879 A2 | 6/2015 | Van Goer et al. |
| 2015/0164883 A1 | 6/2015 | Van Goor et al. |
| 2015/0166516 A1 | 6/2015 | Hadida-Ruah et al. |
| 2015/0174098 A1 | 6/2015 | Ruah et al. |
| 2015/0182517 A1 | 7/2015 | Alargova et al. |
| 2015/0203478 A1 | 7/2015 | Keshavarz-Shokri et al. |
| 2015/0218122 A1 | 8/2015 | Tanoury et al. |
| 2015/0231142 A1 | 8/2015 | Van Goor et al. |
| 2015/0246031 A1 | 9/2015 | Dokou et al. |
| 2015/0293078 A1 | 10/2015 | Singh et al. |
| 2015/0320736 A1 | 11/2015 | Phenix et al. |
| 2015/0336898 A1 | 11/2015 | Grootenhuis et al. |
| 2015/0336956 A1 | 11/2015 | Hadida-Ruah et al. |
| 2016/0022664 A2 | 1/2016 | Van Goor et al. |
| 2016/0022665 A2 | 1/2016 | Van Goor et al. |
| 2016/0039800 A1 | 2/2016 | Young |
| 2016/0067239 A9 | 3/2016 | Van Goor et al. |
| 2016/0095858 A1 | 4/2016 | Miller et al. |
| 2016/0096807 A1 | 4/2016 | Strohmeier et al. |
| 2016/0143898 A1 | 5/2016 | Hadida Ruah et al. |
| 2016/0151335 A1 | 6/2016 | Tait et al. |
| 2016/0166540 A1 | 6/2016 | Looker et al. |
| 2016/0200712 A1 | 7/2016 | Siesel |
| 2016/0221952 A1 | 8/2016 | Yang et al. |
| 2016/0221995 A1 | 8/2016 | Keshavarz-Shokri et al. |
| 2016/0228414 A1 | 8/2016 | Hadida Ruah et al. |
| 2016/0237079 A1 | 8/2016 | Hadida Ruah et al. |
| 2016/0271105 A1 | 9/2016 | Hadida Ruah et al. |
| 2016/0303096 A1 | 10/2016 | Verwijs et al. |
| 2016/0318931 A1 | 11/2016 | Hadida Ruah et al. |
| 2016/0324788 A1 | 11/2016 | Verwijs |
| 2016/0324846 A1 | 11/2016 | Verwijs et al. |
| 2016/0332997 A1 | 11/2016 | Hadida Ruah et al. |
| 2016/0354316 A1 | 12/2016 | Swinney et al. |
| 2017/0087144 A1 | 3/2017 | Rowe et al. |
| 2017/0096396 A1 | 4/2017 | DeMattei et al. |
| 2017/0100340 A1 | 4/2017 | Dokou et al. |
| 2017/0107205 A1 | 4/2017 | Hadida Ruah et al. |
| 2017/0107206 A1 | 4/2017 | Hadida Ruah et al. |
| 2017/0107225 A1 | 4/2017 | Hadida Ruah et al. |
| 2017/0189389 A1 | 7/2017 | Hadida-Ruah et al. |
| 2017/0231970 A1 | 8/2017 | Hurter et al. |
| 2018/0008546 A1 | 1/2018 | Verwijs et al. |

FOREIGN PATENT DOCUMENTS

| | | |
|---|---|---|
| CN | 101006076 A | 7/2007 |
| CN | 101151257 A | 3/2008 |
| CN | 101287732 A | 10/2008 |
| CN | 101460489 A | 6/2009 |
| CN | 101605543 A | 12/2009 |
| DE | 27 35 433 A1 | 2/1978 |
| EA | 4925 B1 | 10/2004 |
| EA | 6155 B1 | 10/2005 |
| EP | 1 380 576 A1 | 1/2004 |
| EP | 1 864 978 A1 | 12/2007 |
| JP | 61-103861 A | 5/1986 |
| JP | 7-45466 B2 | 5/1995 |
| JP | 2004-131393 A | 4/2004 |
| JP | 2009-530416 A | 8/2009 |
| RU | 2005115965 A | 1/2006 |
| RU | 2005128828 A | 5/2006 |
| TW | I244393 B | 12/2005 |
| WO | WO 1995/06046 A1 | 3/1995 |
| WO | WO 1996/19444 A1 | 6/1996 |
| WO | WO 1998/47868 A1 | 10/1998 |
| WO | WO 1998/58925 A1 | 12/1998 |
| WO | WO 2001/19830 A1 | 3/2001 |
| WO | WO 2001/47916 A1 | 7/2001 |
| WO | WO 2002/11883 A1 | 2/2002 |
| WO | WO 2002/12236 A1 | 2/2002 |
| WO | WO 2002/16349 A1 | 2/2002 |
| WO | WO 2003/002533 A1 | 1/2003 |
| WO | WO 2003/007945 A1 | 1/2003 |
| WO | WO 2003/055482 A1 | 7/2003 |

(56) References Cited

FOREIGN PATENT DOCUMENTS

| | | |
|---|---|---|
| WO | WO 2004/028480 A2 | 4/2004 |
| WO | WO 2004/035571 A1 | 4/2004 |
| WO | WO 2004/037806 A1 | 5/2004 |
| WO | WO 2004/041277 A1 | 5/2004 |
| WO | WO 2004/056745 A2 | 7/2004 |
| WO | WO 2004/080972 A1 | 9/2004 |
| WO | WO 2004/091502 A2 | 10/2004 |
| WO | WO 2004/110352 A2 | 12/2004 |
| WO | WO 2004/111014 A1 | 12/2004 |
| WO | WO 2005/016884 A1 | 2/2005 |
| WO | WO 2005/026137 A2 | 3/2005 |
| WO | WO 2005/035514 A2 | 4/2005 |
| WO | WO 2005/037802 A1 | 4/2005 |
| WO | WO 2005/049018 A1 | 6/2005 |
| WO | WO 2005/063746 A1 | 7/2005 |
| WO | WO 2005/075435 A1 | 8/2005 |
| WO | WO 2005/094374 A2 | 10/2005 |
| WO | WO 2005/120497 A2 | 12/2005 |
| WO | WO 2006/002421 A2 | 1/2006 |
| WO | WO 2006/014012 A2 | 2/2006 |
| WO | WO 2006/044456 A1 | 4/2006 |
| WO | WO 2006/044502 A2 | 4/2006 |
| WO | WO 2006/044503 A2 | 4/2006 |
| WO | WO 2006/044505 A2 | 4/2006 |
| WO | WO 2006/044682 A1 | 4/2006 |
| WO | WO 2006/099256 A2 | 9/2006 |
| WO | WO 2006/101740 A2 | 9/2006 |
| WO | WO 2006/110483 A1 | 10/2006 |
| WO | WO 2006/127588 A2 | 11/2006 |
| WO | WO 2007/021982 A2 | 2/2007 |
| WO | WO 2007/044560 A2 | 4/2007 |
| WO | WO 2007/056341 A1 | 5/2007 |
| WO | WO 2007/075567 A1 | 7/2007 |
| WO | WO 2007/075901 A2 | 7/2007 |
| WO | WO 2007/075946 A1 | 7/2007 |
| WO | WO 2007/079139 A2 | 7/2007 |
| WO | WO 2007/087066 A2 | 8/2007 |
| WO | WO 2007/109605 A2 | 9/2007 |
| WO | WO 2007/117715 A2 | 10/2007 |
| WO | WO 2008/051805 A2 | 5/2008 |
| WO | WO 2008/065732 A1 | 6/2008 |
| WO | WO 2008/127399 A2 | 10/2008 |
| WO | WO 2008/147952 A1 | 12/2008 |
| WO | WO 2009/006315 A1 | 1/2009 |
| WO | WO 2009/023509 A2 | 2/2009 |
| WO | WO 2009/036412 A1 | 3/2009 |
| WO | WO 2009/038683 A2 | 3/2009 |
| WO | WO 2009/038913 A2 | 3/2009 |
| WO | WO 2009/066775 A1 | 5/2009 |
| WO | WO 2009/073757 A1 | 6/2009 |
| WO | WO 2009/076141 A2 | 6/2009 |
| WO | WO 2009/076593 A1 | 6/2009 |
| WO | WO 2010/037066 A2 | 4/2010 |
| WO | WO 2010/053471 A1 | 5/2010 |
| WO | WO 2010/054138 A2 | 5/2010 |
| WO | WO 2011/050325 A1 | 4/2011 |
| WO | WO 2011/119984 A1 | 9/2011 |
| WO | WO 2011/127290 A2 | 10/2011 |
| WO | WO 2011/133951 A1 | 10/2011 |
| WO | WO 2013/185112 A1 | 12/2013 |
| WO | WO 2014/014841 A1 | 1/2014 |
| WO | WO 2016/086103 A1 | 6/2016 |
| WO | WO 2016/086136 A1 | 6/2016 |
| WO | WO 2016/160945 A1 | 10/2016 |

OTHER PUBLICATIONS

Beare, N.A. and J.F. Hartwig (Jan. 1, 2002) "Palladium-Catalyzed Arylation of Malonates and Cyanoesters Using Sterically Hindered Trialkyl- and Ferrocenyldialkylphosphine Ligands" *J Org Chem*, 67:541-555.

Bennett, J.C. and F. Plum (Eds.) (1996) *Cecil Textbook of Medicine*. 20th edition, vol. 2, pp. 1992-1996.

Bennett, J.C. and F. Plum (Eds.) (1996) *Cecil Textbook of Medicine*. 20th edition, vol. 2, pp. 2050-2057.

Berge, S.M. et al. (1977) "Pharmaceutical Salts" *J Pharm Sci*, 66(1):1-19.

Bjornsson, T.D. et al. (2003) "The conduct of in vitro and in vivo drug-drug interaction studies: A Pharmaceutical Research and Manufacturers of America (PhRMA) perspective" *Drug Metab Dispos*, 31(7):815-832.

Bombieri, C. et al. (1998) "Complete mutational screening of the CFTR gene in 120 patients with pulmonary disease" *Hum Genet*, 103:718-722.

Braun, J. et al. (1999) "No association between the deltaF508 cystic fibrosis mutation and type 2 diabetes mellitus" *Exp Clin Endocrinol Diabetes*, 107(8):568-569. Abstract; PubMed PMID:10612489 [online]. Retrieved from http://www.ncbi.nlm.nih.gov/pubmed/10612489, on Sep. 24, 2012.

Brittain, H.G. (Ed.) *Polymorphism in Pharmaceutical Solids*. Marcel Dekker, 1999; p. 236.

Bross, P. et al. (1999) "Protein Misfolding and Degradation in Genetic Diseases" *Human Mut*, 14:186-198.

Caira, M.R. (1998) "Crystalline Polymorphism of Organic Compounds" in *Topics of Current Chemistry*, 198:163-208.

Chen, R. et al. (2004) "Improved Dissolution of an Insoluble Drug Using a 4-Fluid Nozzle Spray-Drying Technique" *Chem Pharm Bull*, 52(9):1066-1070.

Chueshov, V.I. (Ed.) (2002) *Manufacturing Technologies of Drugs*. vol. 2. Kharkov:MTK-Kniga, Publishing House NPAU; excerpt, 7 pages.

Cutting, G.R. et al. (1990) "A cluster of cystic fibrosis mutations in the first nucleotide-binding fold of the cystic fibrosis conductance regulator protein" *Nature*, 346:366-369.

Dahl, M. and B.G. Nordestgaard (2009) "Markers of early disease and prognosis in COPD" *Intl J COPD*, 4:157-167.

Dahl, M. et al. (Oct. 9, 2005) "Asthma and COPD in cystic fibrosis intron-8 5T carriers. A population-based study" *Respiratory Research*, 6:113, doi:10.1186/1465-9921-6-113, 9 pages.

Dalemans, W. et al. (Dec. 1991) "Altered chloride ion channel kinetics associated with the ΔF508 cystic fibrosis mutation" *Nature*, 354:526-528.

Database Registry (Nov. 18, 1988) "6-Quinolineacetic acid, α-cyano-, ethyl ester" RN 117646-35-2, Retrieved from STN International [online]; retrieved on Feb. 13, 2015 (1 page).

Database Registry (May 19, 2004) "1,3-Benzodioxole-5-acetic acid, α-cyano-" RN 683220-08-8, Retrieved from STN International [online]; retrieved on Feb. 13, 2015 (1 page).

Dean, M. et al. (Jun. 1990) "Multiple mutations in highly conserved residues are found in mildly affected cystic fibrosis patients" *Cell*, 61:863-870.

Freireich, E.J. et al. (1966) "Quantitative comparison of toxicity of anticancer agents in mouse, rat, hamster, dog, monkey, and man" *Cancer Chemother Rep*, 50(4):219-244.

Fude, Cui (2002) *Pharmaceutics*. 1st Ed. China Medical Science Press, p. 443, 445-446. Chinese with English translation.

Fude, Cui (Feb. 2004) *Pharmaceutics*. 5th Ed. People's Medical Publishing House; p. 113-119, 334. Chinese with English translation.

Galietta, L.J.V. et al. (Jun. 1998) "An improved method to obtain highly differentiated monolayers of human bronchial epithelial cells" *In Vitro Cell Dev Biol*, 34:478-481.

González, J.E. et al. (Oct. 1995) "Voltage Sensing by Fluorescence Resonance Energy Transfer in Single Cells" *Biophys J*, 69(4):1272-1280.

González, J.E. et al. (Apr. 1997) "Improved indicators of cell membrane potential that use fluorescence resonance energy transfer" *Chem Biol*, 4(4):269-277.

González, J.E. et al. (1999) "Cell-based assays and instrumentation for screening ion-channel targets" *Drug Discov Today*, 4(9):431-439.

Gregory, R.J. et al. (Sep. 1990) "Expression and characterization of the cystic fibrosis transmembrane conductance regulator" *Nature*, 347:382-386.

(56) References Cited

OTHER PUBLICATIONS

Hancock, B. and M. Parks (2000) "What Is the True Solubility Advantage of Amorphous Pharmaceuticals?" *Pharm Res*, 17(4):397-404.
International Patent Application No. PCT/US2007/008975, filed Apr. 9, 2007, by Vertex Pharmaceuticals, Inc.: International Preliminary Report on Patentability and Written Opinion, dated Oct. 8, 2008.
International Patent Application No. PCT/US2007/008975, filed Apr. 9, 2007, by Vertex Pharmaceuticals, Inc.: International Search Report, dated Nov. 8, 2007.
International Patent Application No. PCT/US2008/012689, filed Nov. 12, 2008, by Vertex Pharmaceuticals, Inc.: International Preliminary Report on Patentability and Written Opinion, dated May 10, 2011.
International Patent Application No. PCT/US2008/012689, filed Nov. 12, 2008, by Vertex Pharmaceuticals, Inc.: International Search Report, dated Aug. 21, 2009.
International Patent Application No. PCT/US2009/063475, filed Nov. 6, 2009, by Vertex Pharmaceuticals, Inc.: International Search Report, dated Sep. 23, 2010.
International Patent Application No. PCT/US2009/063475, filed Nov. 6, 2009, by Vertex Pharmaceuticals, Inc.: International Preliminary Report on Patentability and Written Opinion, dated May 10, 2011.
International Patent Application No. PCT/US2011/030032, filed Mar. 25, 2011, by Vertex Pharmaceuticals, Inc.: International Search Report, dated Aug. 2, 2011.
International Patent Application No. PCT/US2011/030032, filed Mar. 25, 2011, by Vertex Pharmaceuticals, Inc.: International Preliminary Report on Patentability, dated Sep. 25, 2012.
International Patent Application No. PCT/US2011/033396, filed Apr. 21, 2011, by Vertex Pharmaceuticals, Inc.: International Preliminary Report on Patentability and Written Opinion, dated Oct. 23, 2012.
International Patent Application No. PCT/US2011/033396, filed Apr. 21, 2011, by Vertex Pharmaceuticals, Inc.: International Search Report, dated Nov. 11, 2011.
International Patent Application No. PCT/US2011/033687, filed Apr. 22, 2011, by Vertex Pharmaceuticals, Inc.: International Search Report and Written Opinion, dated Aug. 30, 2011.
International Patent Application No. PCT/US2011/048565, filed Aug. 22, 2011, by Vertex Pharmaceuticals, Inc.: International Search Report and Written Opinion, dated Mar. 20, 2012.
International Patent Application No. PCT/US2011/051725, filed Sep. 15, 2011, by Vertex Pharmaceuticals, Inc.: International Search Report and Written Opinion, dated May 24, 2012.
International Patent Application No. PCT/US2012/064217, filed Nov. 8, 2012, by Vertex Pharmaceuticals, Inc.: International Search Report and Written Opinion, dated Jan. 15, 2013.
International Patent Application No. PCT/US2013/050557, filed Jul. 15, 2013, by Vertex Pharmaceuticals Inc.: International Search Report and Written Opinion, dated Sep. 30, 2013.
International Patent Application No. PCT/US2015/025722, filed Apr. 14, 2015, by Vertex Pharmaceuticals Inc.: International Search Report and Written Opinion, dated Jul. 3, 2015.
Ishiguro, H. et al. (2006) "Dysfunction of pancreatic $HCO_3^-$ secretion and pathogenesis of cystic fibrosis/chronic pancreatitis" *J Japan Pancreas Soc*, 21(1):13-25. Japanese with English abstract.
Jenkins, R. and R.L. Snyder (1996) *Introduction to X-Ray Powder Diffractometry*. New York, NY: John Wiley & Sons, Inc.; pp. 23-26.
Jones, A. and J.M. Helm (Jan. 1, 2009) "Emerging Treatments in Cystic Fibrosis" *Drugs*, 69(14):1903-1910.
Kamal, A. et al. (2005) "Ultrasonic activated efficient method for the cleavage of epoxides with aromatic amines" *Ultrasonics Sonochemistry*, 12(6):429-431.
Kawakami (Jan. 2010) "Formulation of a Poorly Water-soluble Drug by Decrystallization" Chapter 5 in *New Development of Property Evaluation and Formulation Design of Poorly Water Soluble Drugs*. CMC Publishing Co., Ltd.; pp. 212-244. Japanese with English abstract.
Kerem, B-S. et al. (Sep. 1989) "Identification of the cystic fibrosis gene: Genetic analysis" *Science*, 245:1073-1080.
Kerem, B-S. et al. (Nov. 1990) "Identification of mutations in regions corresponding to the two putative nucleotide (ATP)-binding folds of the cystic fibrosis gene" *Proc. Natl. Acad. Sci. USA*, 87:8447-8451.
Kerem, E. et al. (2005) "Standards of care for patients with cystic fibrosis: a European consensus" *J Cystic Fibr*, 4:7-26.
Kerns, E.H. and L. Di (2008) *Drug-like Properties: Concepts, Structure Design and Methods: from ADME to Toxicity Optimization*. London, UK: Academic Press; pp. 122-136 and 197-208.
Konno, H. et al. (2008) "Effect of polymer type on the dissolution profile of amorphous solid dispersions containing felodipine" *Eur J Pharma Biopharma*, 70:493-499.
Krippendorff, B-F. et al. (2007) "Optimizing Classification of Drug-Drug Interaction Potential for CYP450 Isoenzyme Inhibition Assays in Early Drug Discovery" *J Biomol Screen*, 12(1):92-99.
Levin, M. and A.S. Verkman (Apr. 2005) "CFTR-Regulated Chloride Transport at the Ocular Surface in Living Mice Measured by Potential Differences" *Investigative Ophthalmology & Visual Science*, 46:1428-1434.
Miyamatsu, H. et al. (1974) "A New Nonsteroidal Antiinflammatory Agent. 3. Analogs of 2-Substituted 5-Benzothiazoleacetic Acids and Their Derivatives" *J Med Chem*, 17(5):491-496.
Morello, J-P et al. (2000) "Pharmacological chaperones: A new twist on receptor folding" *TiPS*, 21:466-469.
Notice of Allowance and Fee(s) Due for U.S. Appl. No. 13/290,491, dated Oct. 25, 2012.
Notice of Allowance and Fee(s) Due for U.S. Appl. No. 13/871,349, dated Aug. 12, 2014.
Notice of Allowance and Fee(s) Due for U.S. Appl. No. 13/871,349, dated Apr. 17, 2015.
Notice of Allowance and Fee(s) Due for U.S. Appl. No. 13/871,349, dated Oct. 13, 2015.
Notice of Allowance and Fee(s) Due for U.S. Appl. No. 13/887,839, dated Jul. 7, 2014.
Notice of Allowance and Fee(s) Due for U.S. Appl. No. 13/887,839, dated Oct. 16, 2014.
Notice of Allowance and Fee(s) Due for U.S. Appl. No. 13/887,839, dated Feb. 2, 2015.
Notice of Allowance and Fee(s) Due for U.S. Appl. No. 13/887,839, dated Sep. 30, 2015.
Notice of Allowance and Fee(s) Due for U.S. Appl. No. 14/031,360, dated Aug. 14, 2014.
Notice of Allowance and Fee(s) Due for U.S. Appl. No. 14/298,245, dated Jul. 21, 2015.
Notice of Allowance and Fee(s) Due for U.S. Appl. No. 14/298,245, dated Nov. 12, 2015.
Notice of Allowance and Fee(s) Due for U.S. Appl. No. 14/326,930, dated Aug. 14, 2015.
Notice of Allowance and Fee(s) Due for U.S. Appl. No. 14/326,930, dated Dec. 8, 2015.
Notice of Allowance and Fee(s) Due for U.S. Appl. No. 14/334,902, dated Oct. 19, 2015.
Notice of Allowance and Fee(s) Due for U.S. Appl. No. 14/334,902, dated Feb. 18, 2016.
Notice of Allowance and Fee(s) Due for U.S. Appl. No. 14/532,791, dated Jul. 24, 2015.
Notice of Allowance and Fee(s) Due for U.S. Appl. No. 14/532,791, dated Nov. 6, 2015.
Notice of Allowance and Fee(s) Due for U.S. Appl. No. 14/532,791, dated Mar. 1, 2016.
Notice of Allowance and Fee(s) Due for U.S. Appl. No. 14/567,475, dated Sep. 21, 2015.
Notice of Allowance and Fee(s) Due for U.S. Appl. No. 14/567,475, dated Jan. 5, 2016.
Notice of Allowance and Fee(s) Due for U.S. Appl. No. 14/579,098, dated Feb. 1, 2016.
Notice of Allowability for U.S. Appl. No. 14/579,098, dated Apr. 18, 2016.

(56) References Cited

OTHER PUBLICATIONS

Notice of Allowance and Fee(s) Due for U.S. Appl. No. 14/579,098, dated May 12, 2016.
Notice of Allowance and Fee(s) Due for U.S. Appl. No. 14/656,043, dated Aug. 4, 2016.
Notice of Allowance and Fee(s) Due for U.S. Appl. No. 14/687,286, dated Feb. 10, 2016.
Notice of Allowance and Fee(s) Due for U.S. Appl. No. 14/687,286, dated May 19, 2016.
Notice of Allowance and Fee(s) Due for U.S. Appl. No. 14/687,286, dated Sep. 28, 2016.
Notice of Allowance and Fee(s) Due for U.S. Appl. No. 14/877,914, dated Jul. 27, 2016.
Notice of Allowance and Fee(s) Due for U.S. Appl. No. 14/877,914, dated Nov. 14, 2016.
Notice of Allowance and Fee(s) Due for U.S. Appl. No. 14/925,804, dated May 17, 2016.
Notice of Allowance and Fee(s) Due for U.S. Appl. No. 15/001,036, dated Feb. 10, 2017.
Notice of Allowance and Fee(s) Due for U.S. Appl. No. 15/073,591, dated Sep. 28, 2016.
Notice of Allowance and Fee(s) Due for U.S. Appl. No. 15/160,100, dated May 3, 2017.
Notice of Allowance and Fee(s) Due for U.S. Appl. No. 15/162,887, dated Apr. 28, 2017.
Notice of Allowance and Fee(s) Due for U.S. Appl. No. 15/297,983, dated May 18, 2017.
Pasyk, E.A. and J.K. Foskett (May 1995) "Mutant (Δ F508) cystic fibrosis transmembrane conductance regulator Cl⁻ channel is functional when retained in endoplasmic reticulum of mammalian cells" *J Biol Chem*, 270(21):12347-12350.
Pettit, R.S. (2012) "Cystic Fibrosis Transmembrane Conductance Regulator—Modifying Medications: The Future of Cystic Fibrosis Treatment" *Annals of Pharmacotherapy*, 46:1065-1075.
Quinton, P.M. (1990) "Cystic fibrosis: a disease in electrolyte transport" *FASEB J*, 4:2709-2717.
Rich, D.P. et al. (Sep. 1990) "Expression of cystic fibrosis transmembrane conductance regulator corrects defective chloride channel regulation in cystic fibrosis airway epithelial cells" *Nature*, 347:358-363.
Riley, R.J. et al. (2007) "Time-dependent CYP inhibition" *Expert Opin Drug Metab Toxicol*, 3:51-66.
Riordan, J.R. et al. (Sep. 1989) "Identification of the cystic fibrosis gene: cloning and characterization of the complementary DNA" *Science*, 245:1066-1073.
Rutishauser, J. and M. Spiess (2002) "Endoplasmic reticulum storage diseases" *Swiss Med Wkly*, 132:211-222.
Satoshi (2005) "Advances in male infertility therapy" *Urology View*, 3(6):58-61. Japanese with English abstract.
Shastry, B.S. (2003) "Neurodegenerative disorders of protein aggregation" *Neurochem Intl*, 43:1-7.
Stankovic, M. et al. (2008) "The CFTR M470V gene variant as a potential modifier of COPD severity: study of Serbian population" *Genetic Testing*, 12(3):357-362.
Stauffer, S.R. et al. (Jan. 1, 2001) "Palladium-Catalyzed Arylation of Ethyl Cyanoacetate. Fluorescence Resonance Energy Transfer as a Tool for Reaction Discovery" *J Am Chem Soc*, 123(19):4641-4642.
Suzuki, H. et al. (1983) "A simple one-pot conversion of aryl halides into arylacetonitriles" *Chem Lett*, p. 193-194.
The Associated Press (Sep. 24, 2003) "FDA mulls drug to slow late-stage Alzheimer's" [online]. CNN.com. Retrieved from: http://www.cnn.com/2003/HEALTH/condtions/09/24/alzheimers.drug.ap/indexhtml, on Sep. 24, 2003.
The Free Online Dictionary, Definition of Amorphous [online]. Retrieved from: http://www.thefreedictionary.com/amorphous, on May 1, 2012.
Tzetis, M. et al. (2001) "CFTR gene mutations—including three novel nucleotide substitutions—and haplotype background in patients with asthma, disseminated bronchiectasis and chronic obstructive pulmonary disease" *Hum Genet*, 108:216-221.
U.S. Appl. No. 13/632,835, filed Oct. 1, 2012.
U.S. Appl. No. 14/179,762, filed Feb. 13, 2014.
U.S. Appl. No. 14/444,451, filed Jul. 28, 2014.
U.S. Appl. No. 15/234,877, filed Aug. 11, 2016, by Hadida-Ruah et al.
Van Goor, F. et al. (2006) "Rescue of deltaF508-CFTR trafficking and gating in human cystic fibrosis airway primary cultures by small molecules" *Am J Physiol Lung Cell Mol Physiol*, 290(6):L1117-L1130.
Vehring, R. (May 2008) "Pharmaceutical Particle Engineering via Spray Drying" *Pharm Res*, 25(5):999-1022.
Vertex Pharmaceuticals, Inc. (Apr. 5, 2012) "A phase 2, multicenter, double-blinded, placebo controlled, 3-part study to evaluate safety, efficacy, pharmacokinetics, and pharmacodynamics of VX-661 monotherapy and VX-661/VX-770 cotherapy in subjects with cystic fibrosis, homozygous for the F508del-CFTR mutation" [online]. Clinicaltrials.gov. Retrieved from: http://clinicaltrials.gov/archive/NCT01531673/2012_04-05; Identifier: NCT01531673.
Vertex Pharmaceuticals, Inc. (Apr. 18, 2013) "Treatment with VX-661 and Ivacaftor in a Phase 2 Study Resulted in Statistically Significant Improvements in Lung Function in People with Cystic Fibrosis Who Have Two Copies of the F508del Mutation" [online]. Cambridge, Mass.: *Business Wire*. Retrieved from: http://investors.vrtx.com/releasedetail.cfm?ReleaseID=757597.
Vertex Pharmaceuticals, Inc. (Jul. 18, 2013) "A Phase 2, Multi-center, Double-Blinded, Placebo Controlled, 3-Part Study to Evaluate Safety, Efficacy, Pharmacokinetics, and Pharmacodynamics of VX-661 Monotherapy and VX-661/VX-770 Cotherapy in Subjects With Cystic Fibrosis, Homozygous for the F508del-CFTR Mutation" [online]. ClinicalTrials.gov. Retrieved from: http://clinicaltrials.gov/archive/NCT01531673/2013_07_18; Identifier: NCT01531673.
Vertex Pharmaceuticals, Inc. (Mar. 25, 2014) "An Open-Label, Phase 1 Study in Healthy Adult Subjects to Examine the Effects of Multiple-Dose Ciprofloxacin on Ivacaftor and VX-661 in Combination With Ivacaftor" [online]. ClinicalTrials.gov. Retrieved from: https://clinicaltrials.gov/ct2/show/NCT02015507?term=vx-661&rank=4; Identifier: NCT02015507.
Vertex Pharmaceuticals, Inc. (May 1, 2014) "Addition of VX-661 to KALYDECO® (ivacaftor) Improves Lung Function in People with CF Who Are Heterozygous for the F508del and G551D Mutations in 28-day Phase 2 Proof-of-Concept Study" [online]. Boston: *Business Wire*. Retrieved from: http://investors.vrtx.com/releasedetail.cfm?ReleaseID=844677.
Vertex Pharmaceuticals, Inc. (Oct. 17, 2014) "Study to Evaluate Safety and Efficacy of VX-661 in Combination With Ivacaftor in Subjects With Cystic Fibrosis, Homozygous for the F508del-CFTR Mutation With an Open-Label Expansion" [online] ClinicalTrials.gov. Retrieved from: https://clinicaltrials.gov/ct2/show/NCT02070744?term=vx-661&rank=6; Identifier: NCT02070744.
Vertex Pharmaceuticals, Inc. (Mar. 23, 2015) "Vertex Announces Data from 12-Week Phase 2 Safety Study of VX-661 in Combination with Ivacaftor in People with Cystic Fibrosis Who Have Two Copies of the F508del Mutation" [online]. Boston: *Business Wire*. Retrieved from: http://investors.vrtx.com/releasedetail.cfm?ReleaseID=902790.
Vertex Pharmaceuticals, Inc. (May 5, 2015) "Study of VX-661 Alone and in Combination With Ivacaftor in Subjects Homozygous or Heterozygous to the F508del-Cystic Fibrosis Transmembrane Conductance Regulator (CFTR) Mutation" [online]. ClinicalTrials.gov, Identifier: NCT01531673. Retrieved from: https://clinicaltrials.gov/ct2/show/NCT01531673?term=vx-661&rank=3 (5 pages).
Wang, F. et al. (Mar. 1998) "Actions of genistein on cystic fibrosis transmembrane conductance regulator channel gating. Evidence for two binding sites with opposite effects" *J Gen Physiol*, 111(3):477-490.
Yu, H. et al. (2010) "VX-770, an investigational CFTR potentiator, acts on multiple CFTR forms in vitro" *Pediatric Pulmonology*, 45(33):318-319, Abstract 280.
Yu, H. et al. (2012) "Ivacaftor potentiation of multiple CFTR channels with gating mutations" *J Cystic Fibrosis*, 11(3):237-245.

(56) References Cited

OTHER PUBLICATIONS

Chiou, W.L. and S. Riegelman (Sep. 1971) "Pharmaceutical Applications of Solid Dispersion Systems" *J Pharm Sci*, 60(9):1281-1302.
Conti, S. et al. (2007) "Matrices containing NaCMC and HPMC 1. Dissolution performance characterization" *Intl J Pharma*, 333:136-142.
Friesen. D.T. et al. (2098) "Hydroxypropyl Methylcellulose Acetate Succinate-Based Spray-Dried Dispersions: An Overview" *Mol Pharma*, 5(6):1003-1019.
King, F.D. (Ed.) "Bioisosteres, Conformational Restriction and Pro-drugs—Case History: An Example of a Conformational Restriction Approach" In *Medical Chemistry: Principles and Practice*. 1994: Chapter 14, pp. 206-209.
Leuner, C. and J. Dressman (2000) "Improving drug solubility for oral delivery using solid dispersions" *Eur J Pharm Biopharm*, 50:47-60.
Notice of Allowance and Fee(s) Due for U.S. Appl. No. 14/027,791, dated Jul. 31, 2015.
Notice of Allowance and Fee(s) Due for U.S. Appl. No. 15/234,877, dated Jan. 11, 2018.
Notice of Allowance and Fee(s) Due for U.S. Appl. No. 14/687,286, dated Dec. 1, 2017.
Notice of Allowance and Fee(s) Due for U.S. Appl. No. 15/584,324, dated Nov. 20, 2017.
Tanno, F. et al. (2004) "Evaluation of Hypromellose Acetate Succinate (HPMCAS) as a Carrier in Solid Dispersions" *Drug Dev Ind Pharm*, 30(1):9-17.
Vasiliou, V. et al. (Apr. 2009) "Human ATP-binding cassette (ABC) transporter family" *Hum Genomics*, 3(3):281-290.
Wallis, C. (2001) "Mucolytic therapy in cystic fibrosis" *J R Soc Med*, 94(Suppl 40):17-24.

FIG. 15

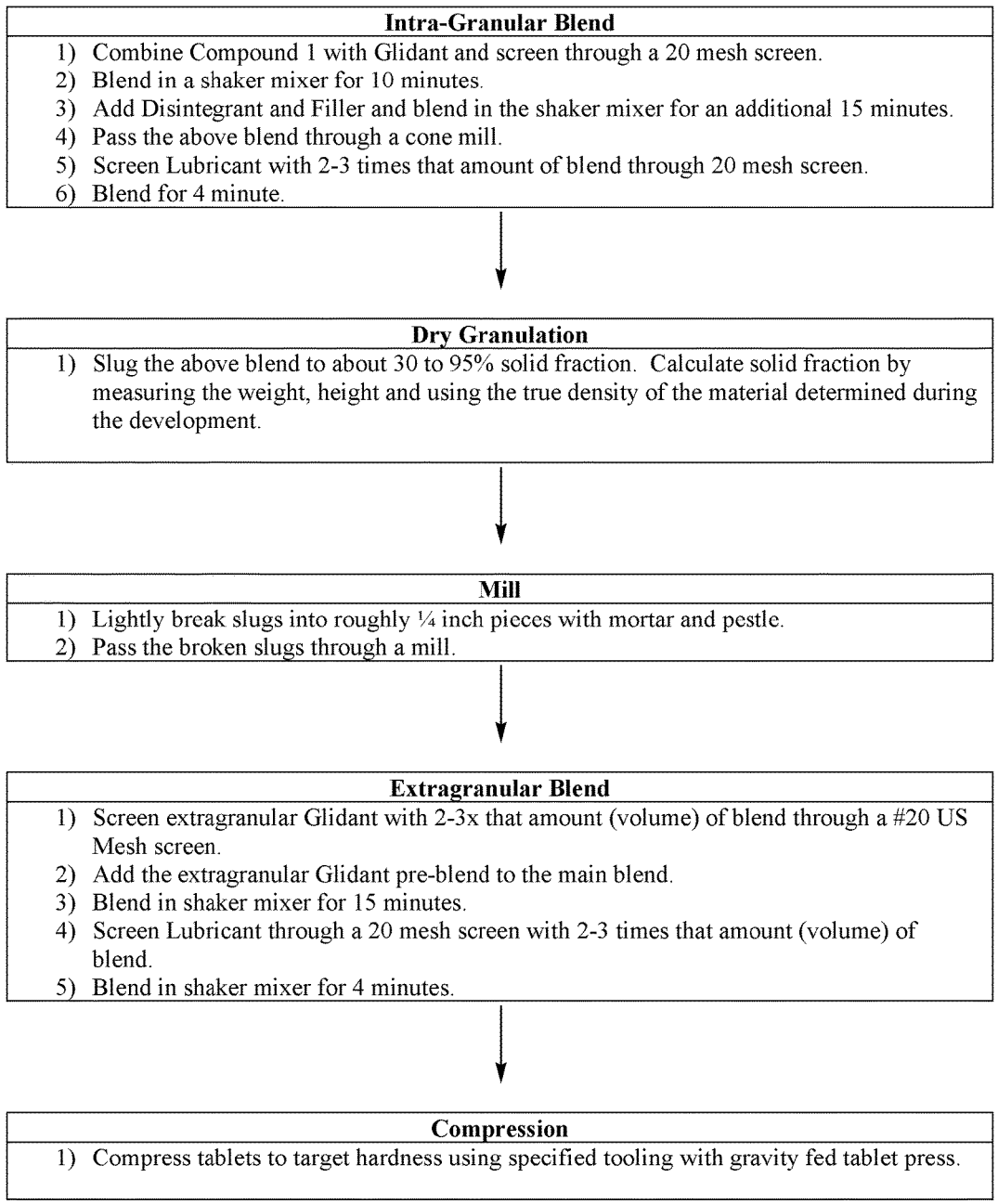

| Intra-Granular Blend |
|---|
| 1) Combine Compound 1 with Glidant and screen through a 20 mesh screen.<br>2) Blend in a shaker mixer for 10 minutes.<br>3) Add Disintegrant and Filler and blend in the shaker mixer for an additional 15 minutes.<br>4) Pass the above blend through a cone mill.<br>5) Screen Lubricant with 2-3 times that amount of blend through 20 mesh screen.<br>6) Blend for 4 minute. |

↓

| Dry Granulation |
|---|
| 1) Slug the above blend to about 30 to 95% solid fraction. Calculate solid fraction by measuring the weight, height and using the true density of the material determined during the development. |

↓

| Mill |
|---|
| 1) Lightly break slugs into roughly ¼ inch pieces with mortar and pestle.<br>2) Pass the broken slugs through a mill. |

↓

| Extragranular Blend |
|---|
| 1) Screen extragranular Glidant with 2-3x that amount (volume) of blend through a #20 US Mesh screen.<br>2) Add the extragranular Glidant pre-blend to the main blend.<br>3) Blend in shaker mixer for 15 minutes.<br>4) Screen Lubricant through a 20 mesh screen with 2-3 times that amount (volume) of blend.<br>5) Blend in shaker mixer for 4 minutes. |

↓

| Compression |
|---|
| 1) Compress tablets to target hardness using specified tooling with gravity fed tablet press. |

FIG. 16

| Intra-Granular Blend |
|---|
| 1) Combine Compound 1 Amorphous Form with colloidal silica dioxide and screen through a 20 mesh screen.<br>2) Blend in a shaker mixer for 10 minutes.<br>3) Add crosscarmelose sodium, microcrystalline cellulose, and lactose monohydrate and blend in the shaker mixer for an additional 15 minutes.<br>4) Pass the above blend through a cone mill.<br>5) Screen magnesium stearate with 2-3 times that amount of blend through 20 mesh screen.<br>6) Blend for 4 minute. |

↓

| Dry Granulation |
|---|
| 1) Slug the above blend to about 30 to 95% solid fraction. Calculate solid fraction by measuring the weight, height and using the true density of the material determined during the development. |

↓

| Mill |
|---|
| 1) Lightly break slugs into roughly ¼ inch pieces with mortar and pestle.<br>2) Pass the broken slugs through a mill. |

↓

| Extragranular Blend |
|---|
| 1) Screen extragranular colloidal silica dioxide with 2-3x that amount (volume) of blend through a #20 US Mesh screen.<br>2) Add the extragranular colloidal silica dioxide pre-blend to the main blend.<br>3) Blend in shaker mixer for 15 minutes.<br>4) Screen magnesium stearate through a 20 mesh screen with 2-3 times that amount (volume) of blend.<br>5) Blend in shaker mixer for 4 minutes. |

↓

| Compression |
|---|
| 1) Compress tablets to target hardness using specified tooling with gravity fed tablet press. |

FIG. 17

| Dry Blend |
|---|
| 1) Screen Compound 1 Amorphous Form through a 20 mesh screen.
2) Screen the microcrystalline cellulose, lactose monohydrate, crosscarmelose sodium, and magnesium stearate separately through a 30 mesh screen.
3) Weigh the required amount of colloidal silicon, premix with the screened lactose and screen together through # 30mesh stainless steel standard sieve.
4) Add components to the blender and mix in the following order:<br>    a. Add approximately $1/3^{rd}$ of the amount of microcrystalline cellulose into the blender and run the blender for 48 revolutions to coat the inner surface of the shell. This procedure prevents SDD from sticking to the inner blender walls.<br>    b. Charge Compound 1 Amorphous Form into the blender and keep the container for rinsing with microcrystalline cellulose to prevent loss of active to the container walls.<br>    c. Rinse the Compound 1 Amorphous Form container with the remaining amount of microcrystalline cellulose and add into the blender.<br>    d. Close the blender and mix for total of 360 revolutions.<br>    e. Add the mixture of lactose monohydrate and colloidal silicon, and crosscarmellose sodium into the blender and blend for 360 revolutions.<br>    f. Add the sifted magnesium stearate to the blender and blend for 96 revolutions. |

↓

| Compression |
|---|
| 1) Compress tablets to target hardness using specified tooling with gravity fed tablet press. |

PHARMACEUTICAL COMPOSITIONS OF (R)-1-(2,2-DIFLUOROBENZO[D][1,3]DIOXO1-5-Y1)-N-(1-(2,3-DIHYDROXYPROPY1)-6-FLUORO-2-(1-HYDROXY-2-METHYLPROPAN-2-Y1)-1H-INDOL-5-Y1) CYCLOPROPANECARBOX-AMIDE AND ADMINISTRATION THEREOF

CROSS-REFERENCE TO RELATED APPLICATIONS

This application is a continuation of U.S. application Ser. No. 14/656,043, filed Mar. 12, 2015, which is a continuation of U.S. application Ser. No. 13/942,617, filed Jul. 15, 2013 (now U.S. Pat. No. 9,012,496, issued Apr. 21, 2015), which claims the benefit of U.S. Provisional Application Ser. No. 61/671,932, filed Jul. 16, 2012, and U.S. Provisional Application Ser. No. 61/822,781, filed May 13, 2013, the entire contents of which are incorporated herein by reference.

TECHNICAL FIELD OF THE INVENTION

The invention relates to pharmaceutical compositions comprising (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide (Compound 1), methods for manufacturing such compositions, methods for administering pharmaceutical compositions comprising same, as well as treatment methods comprising same.

BACKGROUND OF THE INVENTION

CFTR is a cAMP/ATP-mediated anion channel that is expressed in a variety of cells types, including absorptive and secretory epithelia cells, where it regulates anion flux across the membrane, as well as the activity of other ion channels and proteins. In epithelia cells, normal functioning of CFTR is critical for the maintenance of electrolyte transport throughout the body, including respiratory and digestive tissue. CFTR is composed of approximately 1480 amino acids that encode a protein made up of a tandem repeat of transmembrane domains, each containing six transmembrane helices and a nucleotide binding domain. The two transmembrane domains are linked by a large, polar, regulatory (R)-domain with multiple phosphorylation sites that regulate channel activity and cellular trafficking.

The gene encoding CFTR has been identified and sequenced (See Gregory, R. J. et al. (1990) Nature 347:382-386; Rich, D. P. et al. (1990) Nature 347:358-362), (Riordan, J. R. et al. (1989) Science 245:1066-1073). A defect in this gene causes mutations in CFTR resulting in cystic fibrosis ("CF"), the most common fatal genetic disease in humans. Cystic fibrosis affects approximately one in every 2,500 infants in the United States. Within the general United States population, up to 10 million people carry a single copy of the defective gene without apparent ill effects. In contrast, individuals with two copies of the CF associated gene suffer from the debilitating and fatal effects of CF, including chronic lung disease.

In patients with cystic fibrosis, mutations in CFTR endogenously expressed in respiratory epithelia lead to reduced apical anion secretion causing an imbalance in ion and fluid transport. The resulting decrease in anion transport contributes to enhance mucus accumulation in the lung and the accompanying microbial infections that ultimately cause death in CF patients. In addition to respiratory disease, CF patients typically suffer from gastrointestinal problems and pancreatic insufficiency that, if left untreated, results in death. In addition, the majority of males with cystic fibrosis are infertile and fertility is decreased among females with cystic fibrosis. In contrast to the severe effects of two copies of the CF associated gene, individuals with a single copy of the CF associated gene exhibit increased resistance to cholera and to dehydration resulting from diarrhea—perhaps explaining the relatively high frequency of the CF gene within the population.

Sequence analysis of the CFTR gene of CF chromosomes has revealed a variety of disease-causing mutations (Cutting, G. R. et al. (1990) Nature 346:366-369; Dean, M. et al. (1990) Cell 61:863:870; and Kerem, B-S. et al. (1989) Science 245:1073-1080; Kerem, B-S et al. (1990) Proc. Natl. Acad. Sci. USA 87:8447-8451). To date, greater than 1000 disease-causing mutations in the CF gene have been identified as reported by the scientific and medical literature. The most prevalent mutation is a deletion of phenylalanine at position 508 of the CFTR amino acid sequence, and is commonly referred to as ΔF508-CFTR. This mutation occurs in approximately 70 percent of the cases of cystic fibrosis and is associated with a severe disease. Other mutations include the R117H and G551D.

The deletion of residue 508 in ΔF508-CFTR prevents the nascent protein from folding correctly. This results in the inability of the mutant protein to exit the ER, and traffic to the plasma membrane. As a result, the number of channels present in the membrane is far less than observed in cells expressing wild-type CFTR. In addition to impaired trafficking, the mutation results in defective channel gating. Together, the reduced number of channels in the membrane and the defective gating lead to reduced anion transport across epithelia leading to defective ion and fluid transport. (Quinton, P. M. (1990), FASEB J. 4: 2709-2727). Studies have shown, however, that the reduced numbers of ΔF508-CFTR in the membrane are functional, albeit less than wild-type CFTR. (Dalemans et al. (1991), Nature Lond. 354: 526-528; Denning et al., supra; Pasyk and Foskett (1995), J. Cell. Biochem. 270: 12347-50). In addition to ΔF508-CFTR, other disease causing mutations in CFTR that result in defective trafficking, synthesis, and/or channel gating could be up- or down-regulated to alter anion secretion and modify disease progression and/or severity.

Although CFTR transports a variety of molecules in addition to anions, it is clear that this role (the transport of anions) represents one element in an important mechanism of transporting ions and water across the epithelium. The other elements include the epithelial $Na^-$ channel, ENaC, $Na^+/2Cl^-/K^+$ co-transporter, $Na^+$—$K^+$-ATPase pump and the basolateral membrane $K^+$ channels, that are responsible for the uptake of chloride into the cell.

These elements work together to achieve directional transport across the epithelium via their selective expression and localization within the cell. Chloride absorption takes place by the coordinated activity of ENaC and CFTR present on the apical membrane and the $Na^+$—$K^+$-ATPase pump and $Cl^-$ channels expressed on the basolateral surface of the cell. Secondary active transport of chloride from the luminal side leads to the accumulation of intracellular chloride, which can then passively leave the cell via $Cl^-$ channels, resulting in a vectorial transport. Arrangement of $Na^+/2Cl^-/K^+$ co-transporter, $Na^+$—$K^+$-ATPase pump and the basolateral membrane $K^+$ channels on the basolateral surface and CFTR on the luminal side coordinate the secretion of chloride via CFTR on the luminal side. Because water is probably never actively transported itself, its flow across epithelia depends on tiny transepithelial osmotic gradients generated by the bulk flow of sodium and chloride.

As discussed above, it is believed that the deletion of residue 508 in ΔF508-CFTR prevents the nascent protein from folding correctly, resulting in the inability of this mutant protein to exit the ER, and traffic to the plasma membrane. As a result, insufficient amounts of the mature protein are present at the plasma membrane and chloride transport within epithelial tissues is significantly reduced. In fact, this cellular phenomenon of defective endoplasmic reticulum (ER) processing of ATP-binding cassette (ABC) transporters by the ER machinery, has been shown to be the underlying basis not only for CF disease, but for a wide range of other isolated and inherited diseases. The two ways that the ER machinery can malfunction is either by loss of coupling to ER export of the proteins leading to degradation, or by the ER accumulation of these defective/misfolded proteins [Aridor M, et al., Nature Med., 5(7), pp 745-751 (1999); Shastry, B. S., et al., Neurochem. International, 43, pp 1-7 (2003); Rutishauser, J., et al., Swiss Med Wkly, 132, pp 211-222 (2002); Morello, J P et al., TIPS, 21, pp. 466-469 (2000); Bross P., et al., Human Mut., 14, pp. 186-198 (1999)].

(R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide is disclosed in International PCT Publications WO 2010053471 and WO 2010054138 (said publications being incorporated herein by reference in their entirety) as a modulator of CFTR activity and thus as a useful treatment for CFTR-mediated diseases such as cystic fibrosis. Form A and amorphous form of (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide are disclosed in U.S. Provisional Patent Application Ser. Nos.: 61/317,376, filed Mar. 25, 2010, 61/319,953, filed Apr. 1, 2010, 61/321,561, filed Apr. 7, 2010, and 61/321,636, filed Apr. 7, 2010, all of which are incorporated by reference herein in their entirety. A need remains, however, for pharmaceutical compositions comprising Compound 1 that are readily prepared and that are suitable for use as therapeutics.

SUMMARY OF THE INVENTION

The invention relates to pharmaceutical compositions, pharmaceutical preparations, and solid dosage forms comprising (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide (Compound 1) which has the structure below:

1

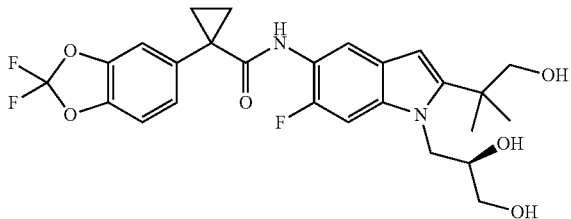

In one aspect, the invention features a tablet for oral administration comprising: a) Compound 1; b) a filler; c) a disintegrant; d) a lubricant; and e) a glidant.

In some embodiments, Compound 1 is in a substantially amorphous form (Compound 1 Amorphous Form). In other embodiments, Compound 1 is in a substantially crystalline solid form. In one embodiment, Compound 1 is in substantially crystalline Form A (Compound 1 Form A). In other embodiments, Compound 1 is in a mixture of solid (i.e., amorphous and crystalline) forms.

In one embodiment, Compound 1 or Compound 1 Amorphous Form is present in the tablet in an amount ranging from about 1 mg to about 250 mg. In one embodiment, Compound 1 or Compound 1 Amorphous Form is present in the tablet in an amount ranging from about 10 mg to about 250 mg. In one embodiment, Compound 1 or Compound 1 Amorphous Form is present in the tablet in an amount ranging from about 25 mg to about 250 mg. In one embodiment, Compound 1 or Compound 1 Amorphous Form is present in the tablet in an amount of about 50 mg to about 200 mg. In one embodiment, Compound 1 or Compound 1 Amorphous Form is present in the tablet in an amount of about 10 mg. In one embodiment, Compound 1 or Compound 1 Amorphous Form is present in the tablet in an amount of about 50 mg. In one embodiment, Compound 1 or Compound 1 Amorphous Form is present in the tablet in an amount of about 100 mg.

In one embodiment, the amount of Compound 1 or Compound 1 Amorphous Form in the tablet ranges from about 1 wt % to about 80 wt % by weight of the tablet. In one embodiment, the amount of Compound 1 or Compound 1 Amorphous Form in the tablet ranges from about 4 wt % to about 50 wt % by weight of the tablet. In one embodiment, the amount of Compound 1 or Compound 1 Amorphous Form in the tablet ranges from about 10 wt % to about 50 wt % by weight of the tablet. In one embodiment, the amount of Compound 1 or Compound 1 Amorphous Form in the tablet ranges from about 20 wt % to about 30 wt % by weight of the tablet. In one embodiment, the amount of Compound 1 or Compound 1 Amorphous Form in the tablet is about 5 wt % of the tablet. In one embodiment, the amount of Compound 1 or Compound 1 Amorphous Form in the tablet is about 25 wt % of the tablet.

In one embodiment, the filler is selected from lactose monohydrate, mannitol, sorbitol, cellulose, calcium phosphate, starch, sugar, cellulose, modified cellulose, sodium carboxymethyl cellulose, ethyl cellulose hydroxymethyl cellulose, hydroxypropylcellulose, cellulose acetate, microcrystalline cellulose, dibasic calcium phosphate, sucrose, lactose, corn starch, potato starch, or any combination thereof. In one embodiment, the filler is microcrystalline cellulose (MCC) and lactose monohydrate and is present in the tablet in an amount ranging from about 10 wt % to about 90 wt % by weight of the tablet. In one embodiment, the filler is microcrystalline cellulose (MCC) and lactose monohydrate and is present in the tablet in an amount ranging from about 40 wt % to about 90 wt % by weight of the tablet.

In one embodiment, the disintegrant is selected from agar-agar, algins, calcium carbonate, carboxmethylcellulose, cellulose, hydroxypropylcellulose, low substituted hydroxypropylcellulose, clays, croscarmellose sodium, crospovidone, gums, magnesium aluminum silicate, methylcellulose, polacrilin potassium, sodium alginate, sodium starch glycolate, maize starch, potato starch, tapioca starch, or any combination thereof. In one embodiment, the disintegrant is croscarmellose sodium and is present in the tablet at a concentration of 6 wt % or less by weight of the tablet.

In one embodiment, the lubricant is selected from magnesium stearate, calcium stearate, zinc stearate, sodium stearate, stearic acid, aluminum stearate, leucine, glyceryl behenate, hydrogenated vegetable oil, sodium stearly fumarate, or any combination thereof. In one embodiment, the lubricant is magnesium stearate and has a concentration of less than 2 wt % by weight of the tablet.

In one embodiment, the glidant is selected from colloidal silicon dioxide, talc, corn starch, or a combination thereof. In one embodiment, the glidant is colloidal silicon dioxide and has a concentration of 3 wt % or less by weight of the tablet.

In one embodiment, the tablet further comprises a colorant.

In one aspect, the invention features A tablet comprising a plurality of granules, the composition comprising: a) Compound 1 Amorphous Form in an amount ranging from about 10 wt % to about 50 wt % by weight of the composition; b) a filler in an amount ranging from about 10 wt % to about 90 wt % by weight of the composition; c) a disintegrant in an amount ranging from about 1 wt % to about 5 wt % by weight of the composition; d) a lubricant in an amount ranging from about 0.3 wt % to about 3 wt % by weight of the composition; and e) a glidant in an amount ranging from about 0.3 wt % to about 3 wt % by weight of the composition.

In one embodiment, Compound 1 is Compound 1 Amorphous Form and is in a spray dried dispersion. In one embodiment, the spray dried dispersion comprises a polymer. In one embodiment, the polymer is hydroxypropylmethylcellulose (HPMC). In one embodiment, the polymer is hydroxypropylmethylcellulose acetate succinate (HPMCAS).

In one embodiment, the polymer is present in an amount from 20% by weight to 70% by weight. In one embodiment, the polymer is present in an amount from 30% by weight to 60% by weight. In one embodiment, the polymer is present in an amount of about 49.5% by weight.

In one embodiment, the tablet further comprises a surfactant. In one embodiment, the surfactant is sodium lauryl sulfate. In one embodiment, the surfactant is present in an amount from 0.1% by weight to 5% by weight. In one embodiment, the surfactant is present in an amount of about 0.5% by weight.

In another aspect, the invention features a tablet of the formulation set forth in Table 1.

TABLE 1

| Component | Function | Final Blend Composition % w/w | Tablet (mg/tablet) |
| --- | --- | --- | --- |
| 50% Compound 1/ 49.5% HPMCAS-HG/ 0.5% sodium lauryl sulfate | Active as a spray dried dispersion (SSD) | 50.00 | 10.0 SDD (5.00 Compound 1) |
| Microcrystalline cellulose | Filler | 22.62 | 45.2 |
| Lactose Monohydrate | Filler | 22.63 | 45.3 |
| Crosscarmelose Sodium | Disintegrant | 3.00 | 0.60 |
| Magnesium Stearate | Lubricant | 0.25 | 0.05 |
| Colloidal Silica Dioxide | Glidant | 1.00 | 0.20 |
| | Intragranular content | 99.5 | |

TABLE 1-continued

| Component | Function | Final Blend Composition % w/w | Tablet (mg/tablet) |
| --- | --- | --- | --- |
| Extragranular Blend | | | |
| Colloidal Silica Dioxide | Glidant | 0.25 | 0.05 |
| Magnesium Stearate | Lubricant | 0.25 | 0.05 |
| | Extragranular content | 0.5 | |
| | Total | 100.00 | 20.0 |

In another aspect, the invention features a tablet of the formulation set forth in Table 2.

TABLE 2

| Component | Function | Final Blend Composition % w/w | Tablet (mg/tablet) |
| --- | --- | --- | --- |
| 50% Compound 1/ 49.5% HPMCAS-HG/ 0.5% sodium lauryl sulfate | Active as a spray dried dispersion (SSD) | 9.53 | 20.00 SDD (10.00 Compound 1) |
| Microcrystalline cellulose | Filler | 43.24 | 90.80 |
| Lactose Monohydrate | Filler | 43.24 | 90.80 |
| Crosscarmelose Sodium | Disintegrant | 3.00 | 6.30 |
| Magnesium Stearate | Lubricant | 0.50 | 1.05 |
| Colloidal Silica Dioxide | Glidant | 0.50 | 1.05 |
| | Total | 100.00 | 210.0 |

In another aspect, the invention features a tablet of the formulation set forth in Table 3.

TABLE 3

| Component | Function | Final Blend Composition % w/w | Tablet (mg/tablet) |
| --- | --- | --- | --- |
| 50% Compound 1/ 49.5% HPMCAS-HG/ 0.5% sodium lauryl sulfate | Active as a spray dried dispersion (SSD) | 50.00 | 100.0 SDD (50.00 Compound 1) |
| Microcrystalline cellulose | Filler | 22.62 | 45.20 |
| Lactose Monohydrate | Filler | 22.63 | 45.30 |
| Crosscarmelose Sodium | Disintegrant | 3.00 | 6.0 |
| Magnesium Stearate | Lubricant | 0.25 | 0.5 |
| Colloidal Silica Dioxide | Glidant | 1.00 | 2.0 |
| | Intragranular content | 99.5 | |
| Extragranular Blend | | | |
| Colloidal Silica Dioxide | Glidant | 0.25 | 0.5 |
| Magnesium Stearate | Lubricant | 0.25 | 0.5 |
| | Extragranular content | 0.5 | |
| | Total | 100.00 | 200.0 |

In another aspect, the invention features a tablet of the formulation set forth in Table 4.

TABLE 4

| Component | Function | Final Blend Composition % w/w | Tablet (mg/tablet) |
|---|---|---|---|
| 50% Compound 1/ 49.5% HPMCAS-HG/ 0.5% sodium lauryl sulfate | Active as a spray dried dispersion (SSD) | 50.00 | 200.0 SDD (100.00 Compound 1) |
| Microcrystalline cellulose | Filler | 22.63 | 90.5 |
| Lactose Monohydrate | Filler | 22.63 | 90.5 |
| Crosscarmelose Sodium | Disintegrant | 3.00 | 12.0 |
| Magnesium Stearate | Lubricant | 0.25 | 1.0 |
| Colloidal Silica Dioxide | Glidant | 1.00 | 4.0 |
|  | Intragranular content | 99.5 |  |
| Extragranular Blend |  |  |  |
| Colloidal Silica Dioxide | Glidant | 0.25 | 1.0 |
| Magnesium Stearate | Lubricant | 0.25 | 1.0 |
|  | Extragranular content | 0.5 |  |
| Total |  | 100.00 | 400.0 |

In another aspect, the invention features a tablet of the formulation set forth in Table 5. Table 5.

TABLE 5

| Component | Function | Final Blend Composition % w/w | Tablet (mg/tablet) |
|---|---|---|---|
| 50% Compound 1/ 49.5% HPMCAS-HG/ 0.5% SLS | Active as a spray dried dispersion (SSD) | 50.00 | 500.0 SDD (250.00 Compound 1) |
| Microcrystalline cellulose (Avicel PH101) | Filler | 22.63 | 226.3 |
| Lactose Monohydrate (Foremost 310) | Filler | 22.63 | 226.3 |
| Crosscarmelose Sodium (AcDiSol) | Disintegrant | 3.00 | 30.0 |
| Magnesium Stearate | Lubricant | 0.25 | 2.5 |
| Colloidal Silica Dioxide (Cabot M5P) | Glidant | 1.00 | 10.0 |
|  | Intragranular content | 99.5 |  |
| Extragranular Blend |  |  |  |
| Colloidal Silica Dioxide (Cabot M5P) | Glidant | 0.25 | 2.5 |
| Magnesium Stearate | Lubricant | 0.25 | 2.5 |
|  | Extragranular content | 0.5 |  |
| Total |  | 100.00 | 1000.0 |

In another aspect, the invention provides a pharmaceutical composition in the form of a tablet that comprises Compound 1, and one or more pharmaceutically acceptable excipients, for example, a filler, a disintegrant, a surfactant, a glidant, and a lubricant and any combination thereof, where the tablet has a dissolution of at least about 50% in about 30 minutes. In another embodiment, the dissolution rate is at least about 75% in about 30 minutes. In another embodiment, the dissolution rate is at least about 90% in about 30 minutes.

In another aspect, the invention provides a pharmaceutical composition in the form of a tablet that comprises a powder blend or granules comprising Compound 1, and, one or more pharmaceutically acceptable excipients, for example, a filler, a disintegrant, a surfactant, a glidant, and a lubricant, wherein the tablet has a hardness of at least about 5 kP (kP=kilo Ponds; 1 kP=~9.8 N). In another embodiment, the tablet has a target friability of less than 1.0% after 400 revolutions.

In another aspect, the invention provides a tablet as described herein further comprising an additional therapeutic agent. In one embodiment, the additional therapeutic agent is a mucolytic agent, bronchodilator, an antibiotic, an anti-infective agent, an anti-inflammatory agent, a CFTR modulator other than Compound 1, or a nutritional agent. In some embodiments, the additional therapeutic agent is N-(5-hydroxy-2,4-ditert-butyl-phenyl)-4-oxo-1H-quinoline-3-carboxamide.

In one aspect, the invention features a method of administering a tablet comprising orally administering to a patient at least once per day a tablet comprising: a) about 25 to 200 mg of Compound 1 Amorphous Form; b) a filler; c) a disintegrant; d) a surfactant; e) a glidant; and f) a lubricant. In one embodiment, the tablet comprises about 2.5 mg of Compound 1 Amorphous Form. In one embodiment, the tablet comprises about 5 mg of Compound 1 Amorphous Form. In one embodiment, the tablet comprises about 10 mg of Compound 1 Amorphous Form. In one embodiment, the tablet comprises about 25 mg of Compound 1 Amorphous Form. In one embodiment, the tablet comprises about 50 mg of Compound 1 Amorphous Form. In one embodiment, the tablet comprises about 100 mg of Compound 1 Amorphous Form. In one embodiment, the tablet comprises about 150 mg of Compound 1 Amorphous Form. In one embodiment, the tablet comprises about 200 mg of Compound 1 Amorphous Form.

In one aspect, the invention features a method of administering a tablet comprising orally administering to a patient twice per day a tablet comprising: a) about 2.5 to 200 mg of Compound 1 Amorphous Form; b) a filler; c) a disintegrant; d) a surfactant; e) a glidant; and f) a lubricant. In one embodiment, the tablet comprises about 2.5 mg of Compound 1 Amorphous Form. In one embodiment, the tablet comprises about 5 mg of Compound 1 Amorphous Form. In one embodiment, the tablet comprises about 10 mg of Compound 1 Amorphous Form. In one embodiment, the tablet comprises about 25 mg of Compound 1 Amorphous Form. In one embodiment, the tablet comprises about 50 mg of Compound 1 Amorphous Form. In one embodiment, the tablet comprises about 100 mg of Compound 1 Amorphous Form. In one embodiment, the tablet comprises about 150 mg of Compound 1 Amorphous Form. In one embodiment, the tablet comprises about 200 mg of Compound 1 Amorphous Form.

In one aspect, the invention features a method for administering a tablet comprising orally administering to a patient once every 12 hours a tablet comprising: a) about 2.5 to 200 mg of Compound 1 Amorphous Form; b) a filler; c) a disintegrant; d) a surfactant; e) a glidant; and f) a lubricant. In one embodiment, the tablet comprises about 2.5 mg of Compound 1 Amorphous Form. In one embodiment, the tablet comprises about 5 mg of Compound 1 Amorphous Form. In one embodiment, the tablet comprises about 10 mg of Compound 1 Amorphous Form. In one embodiment, the tablet comprises about 25 mg of Compound 1 Amorphous Form. In one embodiment, the tablet comprises about 50 mg of Compound 1 Amorphous Form. In one embodiment, the tablet comprises about 100 mg of Compound 1 Amorphous Form. In one embodiment, the tablet comprises about 200 mg of Compound 1 Amorphous Form.

In one aspect, the invention features a method of treating or lessening the severity of a disease in a subject comprising administering to the subject a tablet of the present invention, wherein the disease is selected from cystic fibrosis, asthma, smoke induced COPD, chronic bronchitis, rhinosinusitis, constipation, pancreatitis, pancreatic insufficiency, male infertility caused by congenital bilateral absence of the vas deferens (CBAVD), mild pulmonary disease, idiopathic pancreatitis, allergic bronchopulmonary aspergillosis (ABPA), liver disease, hereditary emphysema, hereditary hemochromatosis, coagulation-fibrinolysis deficiencies, protein C deficiency, Type 1 hereditary angioedema, lipid processing deficiencies, familial hypercholesterolemia, Type 1 chylomicronemia, abetalipoproteinemia, lysosomal storage diseases, I-cell disease/pseudo-Hurler, mucopoly saccharidoses, Sandhof/Tay-Sachs, Crigler-Najjar type II, polyendocrinopathy/hyperinsulemia, Diabetes mellitus, Laron dwarfism, myleoperoxidase deficiency, primary hypoparathyroidism, melanoma, glycanosis CDG type 1, congenital hyperthyroidism, osteogenesis imperfecta, hereditary hypofibrinogenemia, ACT deficiency, Diabetes insipidus (DI), neurophyseal DI, neprogenic DI, Charcot-Marie Tooth syndrome, Perlizaeus-Merzbacher disease, neurodegenerative diseases, Alzheimer's disease, Parkinson's disease, amyotrophic lateral sclerosis, progressive supranuclear plasy, Pick's disease, several polyglutamine neurological disorders, Huntington's, spinocerebullar ataxia type I, spinal and bulbar muscular atrophy, dentatorubal pallidoluysian, myotonic dystrophy, spongiform encephalopathies, hereditary Creutzfeldt-Jakob disease (due to prion protein processing defect), Fabry disease, Straussler-Scheinker syndrome, COPD, dry-eye disease, Sjogren's disease, Osteoporosis, Osteopenia, Gorham's Syndrome, chloride channelopathies, myotonia congenita (Thomson and Becker forms), Bartter's syndrome type III, Dent's disease, hyperekplexia, epilepsy, hyperekplexia, lysosomal storage disease, Angelman syndrome, Primary Ciliary Dyskinesia (PCD), inherited disorders of the structure and/or function of cilia, PCD with situs inversus (also known as Kartagener syndrome), PCD without situs inversus, or ciliary aplasia.

In one embodiment, the disease is cystic fibrosis, emphysema, COPD, or osteoporosis. In one embodiment, the disease is cystic fibrosis.

In one embodiment, the subject has cystic fibrosis transmembrane receptor (CFTR) with a ΔF508 mutation. In one embodiment, the subject has cystic fibrosis transmembrane receptor (CFTR) with a R117H mutation. In one embodiment, the subject has cystic fibrosis transmembrane receptor (CFTR) with a G551D mutation.

In one embodiment, the method comprises administering an additional therapeutic agent. In one embodiment, the additional therapeutic agent is a mucolytic agent, bronchodilator, an antibiotic, an anti-infective agent, an anti-inflammatory agent, a CFTR modulator other than Compound 1, or a nutritional agent. In some embodiments, the additional therapeutic agent is N-(5-hydroxy-2,4-ditert-butyl-phenyl)-4-oxo-1H-quinoline-3-carboxamide.

In another aspect, the invention is directed to a method of treating or lessening the severity of Cystic Fibrosis in patients homozygous for the F580del-CFTR mutation, comprising administering a tablet for oral administration comprising:

a. 5 to 250 mg of (R)-1-(2,2-difluorobenzo[d][1,3]dioxol-5-yl)-N-(1-(2,3-dihydroxypropyl)-6-fluoro-2-(1-hy-droxy-2-methylpropan-2-yl)-1H-indol-5-yl)cyclopropanecarboxamide (Compound 1);
b. a filler;
c. a disintegrant;
d. a lubricant; and
e. a glidant.

followed by co-administration of 100 to 300 mg N-(5-hydroxy-2,4-ditert-butyl-phenyl)-4-oxo-1H-quinoline-3-carboxamide (Compound 2) as a pharmaceutical composition comprising Compound 2 and a pharmaceutically acceptable carrier.

In another aspect, the invention is directed to a method for treating cystic fibrosis in a patient, comprising co-administering:

a) a pharmaceutical composition comprising 5 to 250 mg of (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide (Compound 1) and a pharmaceutically acceptable carrier; and
b) a pharmaceutical composition comprising 100 to 300 mg N-(5-hydroxy-2,4-ditert-butyl-phenyl)-4-oxo-1H-quinoline-3-carboxamide (Compound 2) and a pharmaceutically acceptable carrier;

wherein the patient has a defective gene that causes a deletion of phenylalanine at position 508 of the cystic fibrosis transmembrane conductance regulator amino acid sequence.

In another embodiment, the pharmaceutically acceptable carrier in part a) comprises: i) a filler; ii) a disintegrant; iii) a lubricant; and iv) a glidant.

In another embodiment, the 5 to 250 mg of Compound 1 is administered prior to the 100 to 300 mg of Compound 2. In another embodiment, the 5 to 250 mg of Compound 1 is administered concurrently with the 100 to 300 mg of Compound 2. In another embodiment, the 5 to 250 mg of Compound 1 is administered subsequent to the 100 to 300 mg of Compound 2.

In another embodiment, Compound 1 is in the form of Compound 1 Amorphous Form.

In another embodiment, Compound 1 or Compound 1 Amorphous Form is present in the tablet in an amount of about 10 mg. In another embodiment, Compound 1 or Compound 1 Amorphous Form is present in the tablet in an amount of about 30 mg. In another embodiment, Compound 1 or Compound 1 Amorphous Form is present in the tablet in an amount of about 100 mg.

In another embodiment, the tablet has the formulation set forth in the following table:

| Component | Function | Final Blend Composition % w/w | Tablet (mg/tablet) |
| --- | --- | --- | --- |
| 50% Compound 1/ 49.5% HPMCAS-HG/ 0.5% sodium lauryl sulfate | Active as a spray dried dispersion (SSD) | 50.00 | 10.0 SDD (5.00 Compound 1) |
| Microcrystalline cellulose | Filler | 22.62 | 4.52 |
| Lactose Monohydrate | Filler | 22.63 | 4.53 |
| Crosscarmelose Sodium | Disintegrant | 3.00 | 0.60 |
| Magnesium Stearate | Lubricant | 0.25 | 0.05 |
| Colloidal Silica Dioxide | Glidant | 1.00 | 0.20 |
| | Intragranular content | 99.5 | |

-continued

| Component | Function | Final Blend Composition % w/w | Tablet (mg/tablet) |
|---|---|---|---|
| Extragranular Blend | | | |
| Colloidal Silica Dioxide | Glidant | 0.25 | 0.05 |
| Magnesium Stearate | Lubricant | 0.25 | 0.05 |
| | Extragranular content | 0.5 | |
| | Total | 100.00 | 20.0 |

In another embodiment, the tablet has the formulation set forth in the following table:

| Component | Function | Final Blend Composition % w/w | Tablet (mg/tablet) |
|---|---|---|---|
| 50% Compound 1/ 49.5% HPMCAS-HG/ 0.5% sodium lauryl sulfate | Active as a spray dried dispersion (SSD) | 9.53 | 20.00 SDD (10.00 Compound 1) |
| Microcrystalline cellulose | Filler | 43.24 | 90.80 |
| Lactose Monohydrate | Filler | 43.24 | 90.80 |
| Crosscarmelose Sodium | Disintegrant | 3.00 | 6.30 |
| Magnesium Stearate | Lubricant | 0.50 | 1.05 |
| Colloidal Silica Dioxide | Glidant | 0.50 | 1.05 |
| | Total | 100.00 | 210.0 |

In another embodiment, the tablet has the formulation set forth in the following table:

| Component | Function | Final Blend Composition % w/w | Tablet (mg/tablet) |
|---|---|---|---|
| 50% Compound 1/ 49.5% HPMCAS-HG/ 0.5% sodium lauryl sulfate | Active as a spray dried dispersion (SSD) | 50.00 | 100.0 SDD (50.00 Compound 1) |
| Microcrystalline cellulose | Filler | 22.62 | 45.20 |
| Lactose Monohydrate | Filler | 22.63 | 45.30 |
| Crosscarmelose Sodium | Disintegrant | 3.00 | 6.0 |
| Magnesium Stearate | Lubricant | 0.25 | 0.5 |
| Colloidal Silica Dioxide | Glidant | 1.00 | 2.0 |
| | Intragranular content | 99.5 | |
| Extragranular Blend | | | |
| Colloidal Silica Dioxide | Glidant | 0.25 | 0.5 |
| Magnesium Stearate | Lubricant | 0.25 | 0.5 |
| | Extragranular content | 0.5 | |
| | Total | 100.00 | 200.0 |

In another embodiment, the tablet has the formulation set forth in the following table:

| Component | Function | Final Blend Composition % w/w | Tablet (mg/tablet) |
|---|---|---|---|
| 50% Compound 1/ 49.5% HPMCAS-HG/ 0.5% SLS | Active as a spray dried dispersion (SSD) | 50.00 | 200.0 SDD (100.00 Compound 1) |
| Microcrystalline cellulose (Avicel PH101) | Filler | 22.63 | 90.5 |
| Lactose Monohydrate (Foremost 310) | Filler | 22.63 | 90.5 |
| Crosscarmelose Sodium (AcDiSol) | Disintegrant | 3.00 | 12.0 |
| Magnesium Stearate | Lubricant | 0.25 | 1.0 |
| Colloidal Silica Dioxide (Cabot M5P) | Glidant | 1.00 | 4.0 |
| | Intragranular content | 99.5 | |
| Extragranular Blend | | | |
| Colloidal Silica Dioxide (Cabot M5P) | Glidant | 0.25 | 1.0 |
| Magnesium Stearate | Lubricant | 0.25 | 1.0 |
| | Extragranular content | 0.5 | |
| | Total | 100.00 | 400.0 |

In another embodiment, the tablet has the formulation set forth in the following table:

| Component | Function | Final Blend Composition % w/w | Tablet (mg/tablet) |
|---|---|---|---|
| 50% Compound 1/ 49.5% HPMCAS-HG/ 0.5% SLS | Active as a spray dried dispersion (SSD) | 50.00 | 500.0 SDD (250.00 Compound 1) |
| Microcrystalline cellulose (Avicel PH101) | Filler | 22.63 | 226.3 |
| Lactose Monohydrate (Foremost 310) | Filler | 22.63 | 226.3 |
| Crosscarmelose Sodium (AcDiSol) | Disintegrant | 3.00 | 30.0 |
| Magnesium Stearate | Lubricant | 0.25 | 2.5 |
| Colloidal Silica Dioxide (Cabot M5P) | Glidant | 1.00 | 10.0 |
| | Intragranular content | 99.5 | |
| Extragranular Blend | | | |
| Colloidal Silica Dioxide (Cabot M5P) | Glidant | 0.25 | 2.5 |
| Magnesium Stearate | Lubricant | 0.25 | 2.5 |
| | Extragranular content | 0.5 | |
| | Total | 100.00 | 1000.0 |

In another embodiment, Compound 1 is administered once a day. In another embodiment, 150 mg of Compound 2 is administered. In another embodiment, 250 mg of Compound 2 is administered. In another embodiment, Compound 1 is administered every 12 hours. In another embodiment, Compound 2 is administered every 12 hours.

In another embodiment, the method comprises administering an additional therapeutic agent. In another embodiment, the additional therapeutic agent is a mucolytic agent, bronchodialator, an antibiotic, an anti-infective agent, an anti-inflammatory agent, a CFTR modulator other than Compound 2, or a nutritional agent. In another embodiment, the additional therapeutic agent is a CFTR modulator other than Compound 2.

In another embodiment, the patient is homozygous for the defective gene.

BRIEF DESCRIPTION OF THE DRAWINGS

FIG. 15 is a flow chart depicting an exemplary process for preparing pharmaceutical compositions comprising Compound 1.

FIG. 16 is a flow chart depicting an exemplary process for preparing pharmaceutical compositions comprising Compound 1.

FIG. 17 is a flow chart depicting an exemplary process for preparing pharmaceutical compositions comprising Compound 1.

DETAILED DESCRIPTION OF THE INVENTION

Definitions

Figure 1:
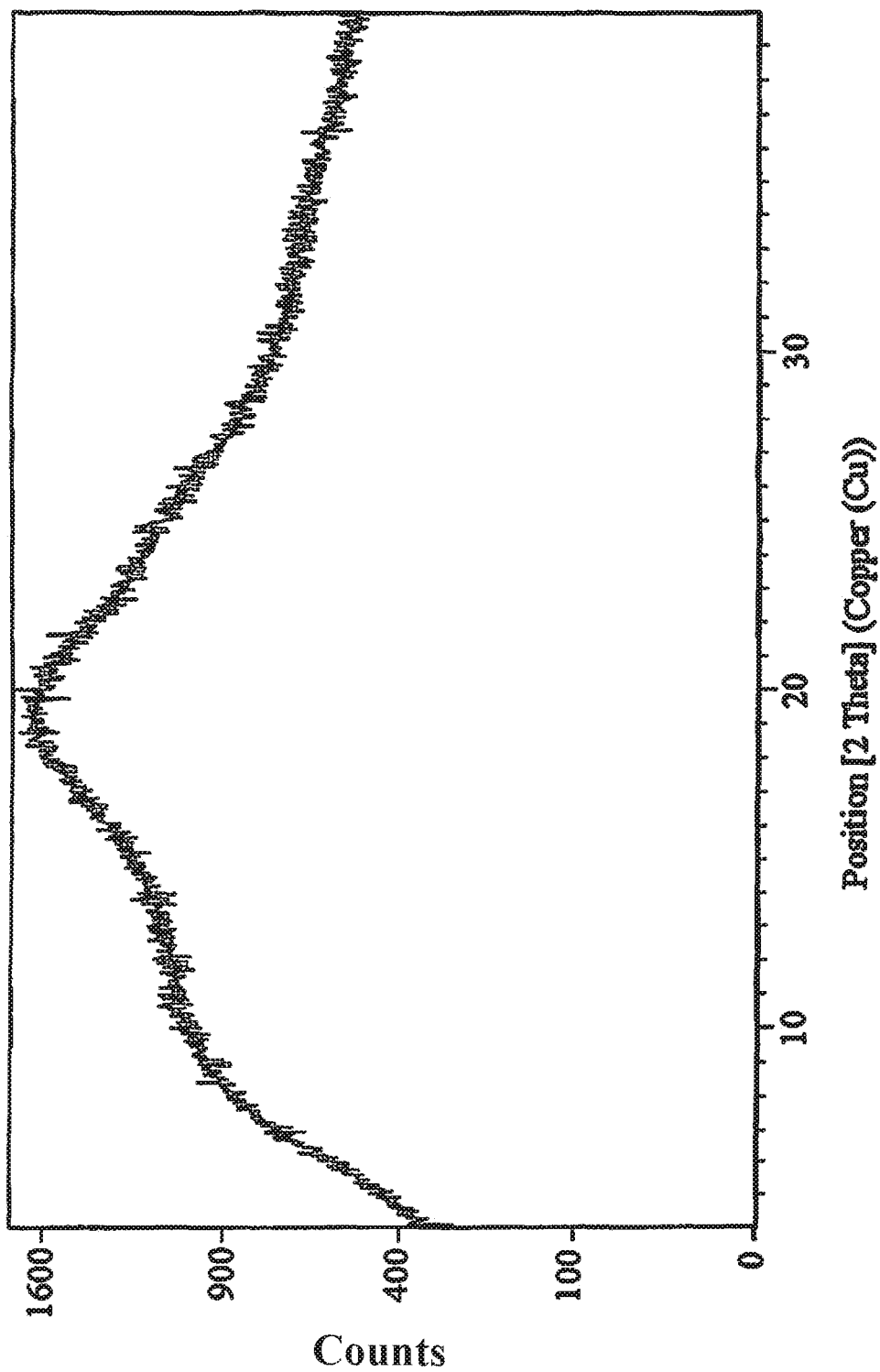
FIG. 1 is an X-ray powder diffraction pattern of Compound 1 Amorphous Form prepared by spray dried methods.

As used herein, "CFTR" stands for cystic fibrosis transmembrane conductance regulator.

As used herein, a "ΔF508 mutation" or "F508-del mutation" is a specific mutation within the CFTR protein. The mutation is a deletion of the three nucleotides that comprise the codon for amino acid phenylalanine at position 508, resulting in CFTR protein that lacks this phenylalanine residue.

As used herein, a patient who is "homozygous" for a particular mutation, e.g. ΔF508, has the same mutation on each allele.

As used herein, a patient who is "heterozygous" for a particular mutation, e.g. ΔF508, has this mutation on one allele, and a different mutation on the other allele.

As used herein, the term "CFTR corrector" refers to a compound that increases the amount of functional CFTR protein to the cell surface, resulting in enhanced ion transport.

As used herein, the term "CFTR potentiator" refers to a compound that increases the channel activity of CFTR protein located at the cell surface, resulting in enhanced ion transport.

As used herein, the term "active pharmaceutical ingredient" or "API" refers to a biologically active compound.

As used herein the term "amorphous" refers to solid forms that consist of disordered arrangements of molecules and do not possess a distinguishable crystal lattice.

As used herein "crystalline" refers to compounds or compositions where the structural units are arranged in fixed geometric patterns or lattices, so that crystalline solids have rigid long range order. The structural units that constitute the crystal structure can be atoms, molecules, or ions. Crystalline solids show definite melting points.

The term "modulating" as used herein means increasing or decreasing, e.g. activity, by a measurable amount.

The term "chemically stable", as used herein, means that the solid form of Compound 1 does not decompose into one or more different chemical compounds when subjected to specified conditions, e.g., 40° C./75% relative humidity, for a specific period of time. e.g. 1 day, 2 days, 3 days, 1 week, 2 weeks, or longer. In some embodiments, less than 25% of the solid form of Compound 1 decomposes, in some embodiments, less than about 20%, less than about 15%, less than about 10%, less than about 5%, less than about 3%, less than about 1%, less than about 0.5% of the form of Compound 1 decomposes under the conditions specified. In some embodiments, no detectable amount of the solid form of Compound 1 decomposes.

The term "physically stable", as used herein, means that the solid form of Compound 1 does not change into one or more different physical forms of Compound 1 (e.g. different solid forms as measured by XRPD, DSC, etc.) when subjected to specific conditions, e.g., 40° C./75% relative humidity, for a specific period of time. e.g. 1 day, 2 days, 3 days, 1 week, 2 weeks, or longer. In some embodiments, less than 25% of the solid form of Compound 1 changes into one or more different physical forms when subjected to specified conditions. In some embodiments, less than about 20%, less than about 15%, less than about 10%, less than about 5%, less than about 3%, less than about 1%, less than about 0.5% of the solid form of Compound 1 changes into one or more different physical forms of Compound 1 when subjected to specified conditions. In some embodiments, no detectable amount of the solid form of Compound 1 changes into one or more physically different solid forms of Compound 1.

The term "substantially free" (as in the phrase "substantially free of form X") when referring to a designated solid form of Compound 1 (e.g., an amorphous or crystalline form described herein) means that there is less than 20% (by weight) of the designated form(s) or co-form(s) (e.g., a crystalline or amorphous form of Compound 1) present, more preferably, there is less than 10% (by weight) of the designated form(s) present, more preferably, there is less than 5% (by weight) of the designated form(s) present, and most preferably, there is less than 1% (by weight) of the designated form(s) present.

As used herein, a "dispersion" refers to a disperse system in which one substance, the dispersed phase, is distributed, in discrete units, throughout a second substance (the continuous phase or vehicle). The size of the dispersed phase can vary considerably (e.g. colloidal particles of nanometer dimension, to multiple microns in size). In general, the dispersed phases can be solids, liquids, or gases. In the case of a solid dispersion, the dispersed and continuous phases are both solids. In pharmaceutical applications, a solid dispersion can include a crystalline drug (dispersed phase) in an amorphous polymer (continuous phase), or alternatively, an amorphous drug (dispersed phase) in an amorphous polymer (continuous phase). In some embodiments an amorphous solid dispersion includes the polymer constituting the dispersed phase, and the drug constitutes the continuous phase. In some embodiments, the dispersion includes amorphous Compound 1 or substantially amorphous Compound 1.

The term "solid amorphous dispersion" generally refers to a solid dispersion of two or more components, usually a drug and polymer, but possibly containing other components such as surfactants or other pharmaceutical excipients, where Compound 1 is amorphous or substantially amorphous (e.g., substantially free of crystalline Compound 1), and the physical stability and/or dissolution and/or solubility of the amorphous drug is enhanced by the other components.

The abbreviations "MTBE" and "DCM" stand for methyl t-butyl ether and dichloromethane, respectively.

The abbreviation "XRPD" stands for X-ray powder diffraction.

The abbreviation "DSC" stands for differential scanning calorimetry.

The abbreviation "TGA" stands for thermogravimetric analysis.

As used herein, the term "active pharmaceutical ingredient" or "API" refers to a biologically active compound. Exemplary APIs include (R)-1-(2,2-difluorobenzo[d][1,3]dioxol-5-yl)-N-(1-(2,3-dihydroxypropyl)-6-fluoro-2-(I-hydroxy-2-methylpropan-2-yl)-1H-indol-5-yl)cyclopropanecarboxamide (Compound 1).

The terms "solid form", "solid forms" and related terms, when used herein to refer to (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide (Compound 1), refer to a solid form e.g. an amorphous powder or crystals and the like, comprising Compound 1 which is not predominantly in a liquid or a gaseous state.

As used herein, the term "substantially amorphous" refers to a solid material having little or no long range order in the position of its molecules. For example, substantially amorphous materials have less than about 15% crystallinity (e.g., less than about 10% crystallinity or less than about 5% crystallinity). It is also noted that the term 'substantially amorphous' includes the descriptor, 'amorphous', which refers to materials having no (0%) crystallinity.

As used herein, the term "substantially crystalline" (as in the phrase substantially crystalline Compound 1 Form A) refers to a solid material having predominantly long range order in the position of its molecules. For example, substantially crystalline materials have more than about 85% crystallinity (e.g., more than about 90% crystallinity or more than about 95% crystallinity). It is also noted that the term 'substantially crystalline' includes the descriptor, 'crystalline', which refers to materials having 100% crystallinity.

As used herein, the term "composition" generally refers to a composition of two or more components, usually one or more drugs (e.g., one drug (e.g., Compound 1 Amorphous Form)) and one or more pharmaceutical excipients.

As used herein, the term "solid dosage form" generally refers to a pharmaceutical composition, which when used in an oral mode of administration include capsules, tablets, pills, powders and granules. In such solid dosage forms, the active compound is mixed with at least one inert, pharmaceutically acceptable excipient or carrier.

As used herein, an "excipient" includes functional and non-functional ingredients in a pharmaceutical composition.

As used herein, a "disintegrant" is an excipient that hydrates a pharmaceutical composition and aids in tablet dispersion. As used herein, a "filler" is an excipient that adds bulkiness and better product properties to a pharmaceutical composition, including facilitating precise metering and handling making compositions practical to produce and convenient to use.

As used herein, a "surfactant" is an excipient that imparts pharmaceutical compositions with enhanced solubility and/or wetability.

As used herein, a "binder" is an excipient that imparts a pharmaceutical composition with enhanced cohesion or tensile strength (e.g., hardness).

As used herein, a "glidant" is an excipient that imparts a pharmaceutical compositions with enhanced flow properties.

As used herein, a "colorant" is an excipient that imparts a pharmaceutical composition with a desired color. Examples of colorants include commercially available pigments such as FD&C Blue #1 Aluminum Lake, FD&C Blue #2, other FD&C Blue colors, titanium dioxide, iron oxide, and/or combinations thereof. In one embodiment, the pharmaceutical composition provided by the invention is purple.

As used herein, a "lubricant" is an excipient that is added to pharmaceutical compositions that are pressed into tablets. The lubricant aids in compaction of granules into tablets and ejection of a tablet of a pharmaceutical composition from a die press.

As used herein, "cubic centimeter" and "cc" are used interchangeably to represent a unit of volume. Note that 1 cc=1 mL.

As used herein, "kiloPond" and "kP" are used interchangeably and refer to the measure of force where a kP=approximately 9.8 Newtons.

As used herein, "friability" refers to the property of a tablet to remain intact and withhold its form despite an external force of pressure. Friability can be quantified using the mathematical expression presented in equation 1:

$$\% \text{ friability} = 100 \times \frac{(W_0 - W_f)}{W_0} \quad (1)$$

wherein $W_0$ is the original weight of the tablet and $W_f$ is the final weight of the tablet after it is put through the friabilator. Friability is measured using a standard USP testing apparatus that tumbles experimental tablets for 100 or 400 revolutions. Some tablets of the invention have a friability of less than 5.0%. In another embodiment, the friability is less than 2.0%. In another embodiment, the target friability is less than 1.0% after 400 revolutions.

As used herein, "mean particle diameter" is the average particle diameter as measured using techniques such as laser light scattering, image analysis, or sieve analysis. In one embodiment, the granules used to prepare the pharmaceutical compositions provided by the invention have a mean particle diameter of less than 1.0 mm.

As used herein, "bulk density" is the mass of particles of material divided by the total volume the particles occupy. The total volume includes particle volume, inter-particle void volume and internal pore volume. Bulk density is not an intrinsic property of a material; it can change depending on how the material is processed. In one embodiment, the granules used to prepare the pharmaceutical compositions provided by the invention have a bulk density of about 0.5-0.7 g/cc.

An effective amount or "therapeutically effective amount" of a drug compound of the invention may vary according to factors such as the disease state, age, and weight of the subject, and the ability of the compound of the invention to elicit a desired response in the subject. Dosage regimens may be adjusted to provide the optimum therapeutic response. An effective amount is also one in which any toxic or detrimental effects (e.g., side effects) of the compound of the invention are outweighed by the therapeutically beneficial effects.

As used herein, the article "a" or "the" is not necessarily limited to a single article. For example, "a filler" may refer to one or more fillers, for example microcrystalline cellulose and lactose monohydrate together.

With respect to Compound 1 (i.e., Compound 1 Amorphous Form or Compound 1 Form A), the terms "about" and "approximately", when used in connection with doses, amounts, or weight percent of ingredients of a composition or a dosage form, mean a dose, amount, or weight percent that is recognized by one of ordinary skill in the art to provide a pharmacological effect equivalent to that obtained from the specified dose, amount, or weight percent. Specifically the term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 30%, 25%, 20%, 15%, 10%, 9%, 8%, 7%, 6%, 5%, 4%, 3%, 2%, 1%, 0.5%, 0.1%, or 0.05% of a given value or range.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. All tautomeric forms of the Compound 1 are included herein. For example, Compound 1 may exist as tautomers, both of which are included herein:

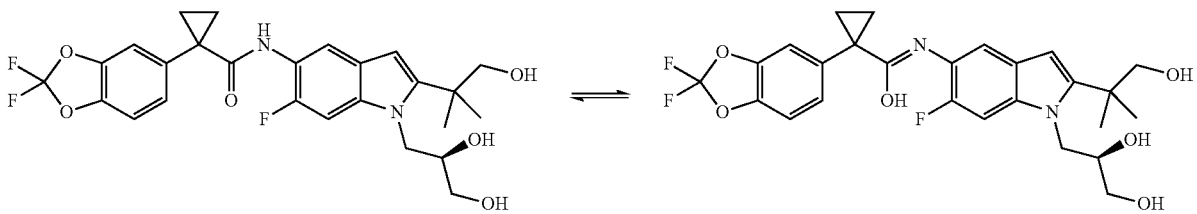 [SMILES: CC(C)(CO)c1cc2cc(NC(=O)C3(c4ccc5c(c4)OC(F)(F)O5)CC3)c(F)cc2n1C[C@@H](O)CO ; CC(C)(CO)c1cc2cc(/N=C(\O)C3(c4ccc5c(c4)OC(F)(F)O5)CC3)c(F)cc2n1C[C@@H](O)CO]

As used herein, and unless otherwise specified, the terms "therapeutically effective amount" and "effective amount" of a compound mean an amount sufficient to provide a therapeutic benefit in the treatment or management of a disease or disorder, or to delay or minimize one or more symptoms associated with the disease or disorder. A "therapeutically effective amount" and "effective amount" of a compound mean an amount of therapeutic agent, alone or in combination with one or more other agent(s), which provides a therapeutic benefit in the treatment or management of the disease or disorder. The terms "therapeutically effective amount" and "effective amount" can encompass an amount that improves overall therapy, reduces or avoids symptoms or causes of disease or disorder, or enhances the therapeutic efficacy of another therapeutic agent.

"Substantially pure" as used in the phrase "substantially pure Compound 1 Amorphous Form," means greater than about 90% purity. In another embodiment, substantially pure refers to greater than about 95% purity. In another embodiment, substantially pure refers to greater than about 98% purity. In another embodiment, substantially pure refers to greater than about 99% purity.

"Co-administered" or "Co-administration" as used herein refers to administering one or more additional therapeutic agents prior to, concurrent with, or subsequent to Compound 1 or a pharmaceutical composition thereof.

Additionally, unless otherwise stated, structures depicted herein are also meant to include compounds that differ only in the presence of one or more isotopically enriched atoms. For example, Compound 1, wherein one or more hydrogen atoms are replaced deuterium or tritium, or one or more carbon atoms are replaced by a $^{13}$C- or $^{14}$C-enriched carbon are within the scope of this invention. Such compounds are useful, for example, as analytical tools, probes in biological assays, or compounds with improved therapeutic profile.

Pharmaceutical Compositions

The invention provides pharmaceutical compositions, pharmaceutical formulations and solid dosage forms such as tablets comprising Compound 1 Amorphous Form or Compound 1 Form A. In some embodiments of this aspect, the amount of Compound 1 that is present in the pharmaceutical composition is 2.5 mg, 5 mg, 10 mg, 25 mg, 50 mg, 75 mg, 100 mg, 125 mg, 150 mg, 200 mg, or 250 mg. In some embodiments of this aspect, weight/weight relative percent of Compound 1 that is present in the pharmaceutical composition is from 10 to 50 percent. In these and other embodiments, Compound 1 is present as substantially pure Compound 1 Amorphous Form. "Substantially pure" means greater than ninety percent pure; preferably greater than 95 percent pure; more preferably greater than 99.5 percent pure (i.e., not mixed with crystalline forms of Compound 1).

Thus, in one aspect, the invention provides a pharmaceutical composition comprising:
a. Compound 1 Amorphous Form;
b. a filler;
c. a disintegrant;
d. a lubricant; and
e. a glidant.

In one embodiment of this aspect, the pharmaceutical composition comprises 2.5 mg of Compound 1 Amorphous Form. In one embodiment of this aspect, the pharmaceutical composition comprises 5 mg of Compound 1 Amorphous Form. In one embodiment of this aspect, the pharmaceutical composition comprises 10 mg of Compound 1 Amorphous Form. In one embodiment of this aspect, the pharmaceutical composition comprises 25 mg of Compound 1 Amorphous Form. In another embodiment of this aspect, the pharmaceutical composition comprises 50 mg of Compound 1 Amorphous Form. In another embodiment of this aspect, the pharmaceutical composition comprises 100 mg of Compound 1 Amorphous Form. In another embodiment of this aspect, the pharmaceutical composition comprises 125 mg of Compound 1 Amorphous Form. In another embodiment of this aspect, the pharmaceutical composition comprises 150 mg of Compound 1 Amorphous Form. In another embodiment of this aspect, the pharmaceutical composition comprises 200 mg of Compound 1 Amorphous Form. In another embodiment of this aspect, the pharmaceutical composition comprises 250 mg of Compound 1 Amorphous Form.

In some embodiments, the pharmaceutical compositions comprises Compound 1 Amorphous Form, wherein Compound 1 Amorphous Form is present in an amount of at least 4 wt % (e.g., at least 5 wt %, at least 10 wt %, at least 20 wt %, at least 30 wt %, at least 40 wt %, at least 50 wt %, or at least 60 wt %) by weight of the composition.

In some embodiments, the pharmaceutical composition comprises Compound 1 Amorphous Form, a filler, a disintegrant, a glidant, and a lubricant. In this embodiment, the composition comprises from about 4 wt % to about 50 wt % (e.g., about 10-45 wt %) of Compound 1 Amorphous Form by weight of the composition, and more typically, from 20 wt % to about 40 wt % (e.g., about 25-30 wt %) of Compound 1 Amorphous Form by weight of the composition.

In some embodiments, the pharmaceutical composition comprises Compound 1 Amorphous Form, a filler, a disintegrant, a glidant, and a lubricant. In this embodiment, the composition comprises from about 4 wt % to about 50 wt % (e.g., about 10-45 wt %) of Compound 1 Amorphous Form by weight of the composition, and more typically from 20 wt % to about 40 wt % (e.g., about 25-30 wt %) of Compound 1 Amorphous Form by weight of the composition.

The concentration of Compound 1 Amorphous Form in the composition depends on several factors such as the amount of pharmaceutical composition needed to provide a desired amount of Compound 1 Amorphous Form and the desired dissolution profile of the pharmaceutical composition.

In another embodiment, the pharmaceutical composition comprises Compound 1 in which the Compound 1 in its solid form has a mean particle diameter, measured by light scattering (e.g., using a Malvern Mastersizer available from Malvern Instruments in England) of 0.1 microns to 10 microns. In another embodiment, the particle size of Compound 1 is 1 micron to 5 microns. In another embodiment, Compound 1 has a particle size D50 of 2.0 microns.

As indicated, in addition to Compound 1 Amorphous Form, in some embodiments of the invention, the pharmaceutical compositions which are oral formulations also comprise one or more excipients such as fillers, disintegrants, surfactants, glidants, lubricants, colorants, or fragrances and any combination thereof.

Fillers suitable for the invention are compatible with the ingredients of the pharmaceutical composition, i.e., they do not substantially reduce the solubility, the hardness, the chemical stability, the physical stability, or the biological activity of the pharmaceutical composition. Exemplary fillers include: sugars, for example, confectioner's sugar, compressible sugar, dextrates, dextrin, dextrose, lactose, lactose monohydrate, mannitol, sorbitol, cellulose, and modified celluloses, for example, powdered cellulose, talc, calcium phosphate, starch, celluloses, modified celluloses, (e.g. sodium carboxymethyl cellulose, ethyl cellulose hydroxymethyl cellulose, hydroxypropylcellulose), cellulose acetate, microcrystalline cellulose, calcium phosphates, dibasic calcium phosphate, starches (e.g. corn starch, potato starch), sugars (e.g., sorbitol) lactose, sucrose, or the like), or any combination thereof.

Thus, in one embodiment, the pharmaceutical composition comprises at least one filler in an amount of at least 5 wt % (e.g., at least about 20 wt %, at least about 30 wt %, or at least about 40 wt %) by weight of the composition. For example, the pharmaceutical composition comprises from about 10 wt % to about 90 wt % (e.g., from about 30 wt % to about 90 wt %, from about 40 wt % to about 85 wt %, or from about 45 wt % to about 80 wt %) of filler, by weight of the composition. In another example, the pharmaceutical composition comprises at least about 40 wt % (e.g., at least 20 wt % or at least 20 wt %) of microcrystalline cellulose, for example MCC Avicel PH102, and lactose monohydrate by weight of the composition.

Disintegrants suitable for the invention enhance the dispersal of the pharmaceutical composition and are compatible with the ingredients of the pharmaceutical composition, i.e., they do not substantially reduce the chemical stability, the physical stability, the hardness, or the biological activity of the pharmaceutical composition. Exemplary disintegrants include croscarmellose sodium, sodium starch glycolate, or a combination thereof.

Thus, in one embodiment, the pharmaceutical composition comprises disintegrant in an amount of about 10 wt % or less (e.g., about 7 wt % or less, about 6 wt % or less, or about 5 wt % or less) by weight of the composition. For example, the pharmaceutical composition comprises from about 1 wt % to about 10 wt % (e.g., from about 1.5 wt % to about 7.5 wt % or from about 2.5 wt % to about 6 wt %) of disintegrant, by weight of the composition. In some examples, the pharmaceutical composition comprises from about 0.1% to about 10 wt % (e.g., from about 0.5 wt % to about 7.5 wt % or from about 1.5 wt % to about 6 wt %) of disintegrant, by weight of the composition. In still other examples, the pharmaceutical composition comprises from about 0.5% to about 10 wt % (e.g., from about 1.5 wt % to about 7.5 wt % or from about 2.5 wt % to about 6 wt %) of disintegrant, by weight of the composition.

Surfactants suitable for the invention enhance the wettability of the pharmaceutical composition and are compatible with the ingredients of the pharmaceutical composition, i.e., they do not substantially reduce the chemical stability, the physical stability, the hardness, or the biological activity of the pharmaceutical composition. Exemplary surfactants include sodium lauryl sulfate (SLS), sodium stearyl fumarate (SSF), polyoxyethylene 20 sorbitan mono-oleate (e.g., Tween™), any combination thereof, or the like.

Thus, in one embodiment, the pharmaceutical composition comprises a surfactant in an amount of about 10 wt % or less (e.g., about 5 wt % or less, about 2 wt % or less, about 1 wt % or less, about 0.8 wt % or less, or about 0.6 wt % or less) by weight of the composition. For example, the pharmaceutical composition includes from about 10 wt % to about 0.1 wt % (e.g., from about 5 wt % to about 0.2 wt % or from about 2 wt % to about 0.3 wt %) of surfactant, by weight of the composition. In yet another example, the pharmaceutical composition comprises from about 10 wt % to about 0.1 wt % (e.g., from about 5 wt % to about 0.2 wt % or from about 2 wt % to about 0.3 wt %) of sodium lauryl sulfate, by weight of the composition.

Glidants suitable for the invention enhance the flow properties of the pharmaceutical composition and are compatible with the ingredients of the pharmaceutical composition, i.e., they do not substantially reduce the solubility, the hardness, the chemical stability, the physical stability, or the biological activity of the pharmaceutical composition. Exemplary glidants include colloidal silicon dioxide, talc, or a combination thereof.

Thus, in one embodiment, the pharmaceutical composition comprises a glidant in an amount of 2 wt % or less (e.g., 1.75 wt %, 1.25 wt % or less, or 1.00 wt % or less) by weight of the composition. For example, the pharmaceutical composition comprises from about 2 wt % to about 0.05 wt % (e.g., from about 1.5 wt % to about 0.07 wt % or from about 1.0 wt % to about 0.09 wt %) of glidant, by weight of the composition. In another example, the pharmaceutical composition comprises 2 wt % or less (e.g., 1.75 wt %, 1.25 wt % or less, or 1.00 wt % or less) of colloidal silicon dioxide, by weight of the composition. In yet another example, the pharmaceutical composition comprises from about 2 wt % to about 0.05 wt % (e.g., from about 1.5 wt % to about 0.07 wt % or from about 1.0 wt % to about 0.09 wt %) of colloidal silicon dioxide, by weight of the composition.

In some embodiments, the pharmaceutical composition can include an oral solid pharmaceutical dosage form which can comprise a lubricant that can prevent adhesion of a granulate-bead admixture to a surface (e.g., a surface of a mixing bowl, a compression die and/or punch). A lubricant can also reduce interparticle friction within the granulate and improve the compression and ejection of compressed pharmaceutical compositions from a die press. The lubricant is also compatible with the ingredients of the pharmaceutical composition, i.e., they do not substantially reduce the solubility, the hardness, or the biological activity of the pharmaceutical composition. Exemplary lubricants include magnesium stearate, calcium stearate, zinc stearate, sodium stearate, stearic acid, aluminum stearate, leucine, glyceryl behenate, hydrogenated vegetable oil or any combination thereof. In one embodiment, the pharmaceutical composition comprises a lubricant in an amount of 5 wt % or less (e.g., 4.75 wt %, 4.0 wt % or less, or 3.00 wt % or less, or 2.0 wt % or less) by weight of the composition. For example, the pharmaceutical composition comprises from about 5 wt % to about 0.10 wt % (e.g., from about 4.5 wt % to about 0.5 wt % or from about 3 wt % to about 0.5 wt %) of lubricant, by weight of the composition. In another example, the pharmaceutical composition comprises 5 wt % or less (e.g., 4.0 wt % or less, 3.0 wt % or less, or 2.0 wt % or less, or 1.0 wt % or less) of magnesium stearate, by weight of the composition. In yet another example, the pharmaceutical composition comprises from about 5 wt % to about 0.10 wt % (e.g., from about 4.5 wt % to about 0.15 wt % or from about 3.0 wt % to about 0.50 wt %) of magnesium stearate, by weight of the composition.

Pharmaceutical compositions of the invention can optionally comprise one or more colorants, flavors, and/or fragrances to enhance the visual appeal, taste, and/or scent of the composition. Suitable colorants, flavors, or fragrances are compatible with the ingredients of the pharmaceutical composition, i.e., they do not substantially reduce the solubility, the chemical stability, the physical stability, the hardness, or the biological activity of the pharmaceutical composition. In one embodiment, the pharmaceutical composition comprises a colorant, a flavor, and/or a fragrance. In one embodiment, the pharmaceutical compositions provided by the invention are purple.

In some embodiments, the pharmaceutical composition includes or can be made into tablets and the tablets can be coated with a colorant and optionally labeled with a logo, other image and/or text using a suitable ink. In still other embodiments, the pharmaceutical composition includes or can be made into tablets and the tablets can be coated with a colorant, waxed, and optionally labeled with a logo, other image and/or text using a suitable ink. Suitable colorants and inks are compatible with the ingredients of the pharmaceutical composition, i.e., they do not substantially reduce the solubility, the chemical stability, the physical stability, the hardness, or the biological activity of the pharmaceutical composition. The suitable colorants and inks can be any color and are water based or solvent based. In one embodiment, tablets made from the pharmaceutical composition are coated with a colorant and then labeled with a logo, other image, and/or text using a suitable ink. For example, tablets comprising pharmaceutical composition as described herein can be coated with about 3 wt % (e.g., less than about 6 wt % or less than about 4 wt %) of film coating comprising a colorant. The colored tablets can be labeled with a logo and text indicating the strength of the active ingredient in the tablet using a suitable ink. In another example, tablets comprising pharmaceutical composition as described herein can be coated with about 3 wt % (e.g., less than about 6 wt % or less than about 4 wt %) of a film coating comprising a colorant.

In another embodiment, tablets made from the pharmaceutical composition are coated with a colorant, waxed, and then labeled with a logo, other image, and/or text using a suitable ink. For example, tablets comprising pharmaceutical composition as described herein can be coated with about 3 wt % (e.g., less than about 6 wt % or less than about 4 wt %) of film coating comprising a colorant. The colored tablets can be waxed with Carnauba wax powder weighed out in the amount of about 0.01% w/w of the starting tablet core weight. The waxed tablets can be labeled with a logo and text indicating the strength of the active ingredient in the tablet using a suitable ink. In another example, tablets comprising pharmaceutical composition as described herein can be coated with about 3 wt % (e.g., less than about 6 wt % or less than about 4 wt %) of a film coating comprising a colorant The colored tablets can be waxed with Carnauba wax powder weighed out in the amount of about 0.01% w/w of the starting tablet core weight. The waxed tablets can be labeled with a logo and text indicating the strength of the active ingredient in the tablet using a pharmaceutical grade ink such as a black ink (e.g., Opacode® S-1-17823, a solvent based ink, commercially available from Colorcon, Inc. of West Point, Pa.).

One exemplary pharmaceutical composition comprises from about 4 wt % to about 70 wt % (e.g., from about 10 wt % to about 60 wt %, from about 15 wt % to about 50 wt %, or from about 25 wt % to about 50 wt %, or from about 20 wt % to about 70 wt %, or from about 30 wt % to about 70 wt %, or from about 40 wt % to about 70 wt %, or from about 50 wt % to about 70 wt %) of Compound 1 Amorphous Form, by weight of the composition. The aforementioned compositions can also include one or more pharmaceutically acceptable excipients, for example, from about 40 wt % to about 90 wt % of a filler; from about 1 wt % to about 5 wt % of a disintegrant; from about 2 wt % to about 0.25 wt % of a surfactant; from about 2 wt % to about 0.05 wt % of a glidant; and from about 5 wt % to about 0.1 wt % of a lubricant. Or, the pharmaceutical composition comprises a composition containing from about 15 wt % to about 70 wt % (e.g., from about 20 wt % to about 60 wt %, from about 25 wt % to about 55 wt %, or from about 30 wt % to about 50 wt %) of Compound 1 Amorphous Form, by weight of the composition; and one or more excipients, for example, from about 40 wt % to about 90 wt % of a filler; from about 1 wt % to about 5 wt % of a disintegrant; from about 2 wt % to about 0.25 wt % of a surfactant; from about 2 wt % to about 0.05 wt % of a glidant; and from about 5 wt % to about 0.1 wt % of a lubricant.

Another exemplary pharmaceutical composition comprises from about 4 wt % to about 70 wt % (e.g., from about 10 wt % to about 60 wt %, from about 15 wt % to about 50 wt %, or from about 25 wt % to about 50 wt % or from about 20 wt % to about 70 wt %, or from about 30 wt % to about 70 wt %, or from about 40 wt % to about 70 wt %, or from about 50 wt % to about 70 wt %) of Compound 1 Amorphous Form by weight of the composition, and one or more excipients, for example, from about 40 wt % to about 90 wt % of a filler; from about 1 wt % to about 5 wt % of a disintegrant; from about 2 wt % to about 0.25 wt % of a surfactant; from about 2 wt % to about 0.05 wt % of a glidant; and from about 2 wt % to about 0.1 wt % of a lubricant.

In one embodiment, the invention is a dry blend or a granular pharmaceutical composition comprising:
a. about 25 wt % of Compound 1 Amorphous Form by weight of the composition;
b. about 22.5 wt % of microcrystalline cellulose by weight of the composition;
c. about 22.5 wt % of lactose monohydrate by weight of the composition;
d. about 3 wt % of sodium croscarmellose sodium by weight of the composition;
e. about 0.25 wt % of sodium lauryl sulfate by weight of the composition;
f. about 0.5 wt % of magnesium stearate by weight of the composition; and
g. about 1.25 wt % of colloidal silica by weight of the composition.

In one embodiment, the invention is a dry blend or a granular pharmaceutical composition comprising:
a. about 25 wt % of Compound 1 Amorphous Form by weight of the composition;
b. about 22.5 wt % of microcrystalline cellulose by weight of the composition;
c. about 22.5 wt % of lactose monohydrate by weight of the composition;
d. about 3 wt % of sodium croscarmellose sodium by weight of the composition;
e. about 0.25 wt % of sodium lauryl sulfate by weight of the composition;
f. about 0.5 wt % of magnesium stearate by weight of the composition;
g. about 1.25 wt % of colloidal silica by weight of the composition; and
h. about 25 wt % of a polymer.

In one embodiment, the invention is a dry blend or a granular pharmaceutical composition comprising:
a. about 5 wt % of Compound 1 Amorphous Form by weight of the composition;
b. about 42.9 wt % of microcrystalline cellulose by weight of the composition;
c. about 42.9 wt % of lactose monohydrate by weight of the composition;
d. about 3 wt % of sodium croscarmellose sodium by weight of the composition;
e. about 0.5 wt % of magnesium stearate by weight of the composition;
g. about 1.25 wt % of colloidal silica by weight of the composition; and
h. about 5 wt % of a polymer.

In another embodiment, the polymer is HPMCAS.

The pharmaceutical compositions of the invention can be processed into a tablet form, capsule form, pouch form, lozenge form, or other solid form that is suited for oral administration. Thus in some embodiments, the pharmaceutical compositions are in tablet form.

In still another pharmaceutical oral formulation of the invention, a shaped pharmaceutical tablet composition having an initial hardness of 5-21 kP±20 percent comprises: about 25 wt % of Compound 1 Amorphous Form; about 22.5 wt % of microcrystalline cellulose by weight of the composition; about 22.5 wt % of lactose monohydrate by weight of the composition; about 3 wt % of sodium croscarmellose sodium by weight of the composition; about 0.25 wt % of sodium lauryl sulfate by weight of the composition; about 0.5 wt % of magnesium stearate by weight of the composition; and about 1.25 wt % of colloidal silica by weight of the composition. Wherein the amount of Compound 1 Amorphous Form in the shaped pharmaceutical tablet ranges from about 25 mg to about 200 mg, for example, 50 mg, or 75 mg, or 100 mg, or 150 mg or 200 mg Compound 1 Amorphous Form per tablet.

In certain embodiments, the shaped pharmaceutical tablet contains about 10 mg of Compound 1 Amorphous Form. In certain embodiments, the shaped pharmaceutical tablet contains about 50 mg of Compound 1 Amorphous Form. In certain embodiments, the shaped pharmaceutical tablet contains about 100 mg of Compound 1 Amorphous Form.

Another aspect of the invention provides a pharmaceutical formulation consisting of a tablet or capsule that includes a Compound 1 Amorphous Form and other excipients (e.g., a filler, a disintegrant, a surfactant, a glidant, a colorant, a lubricant, or any combination thereof), each of which is described above and in the Examples below, wherein the tablet has a dissolution of at least about 50% (e.g., at least about 60%, at least about 70%, at least about 80%, at least about 90%, or at least about 99%) in about 30 minutes. In one example, the pharmaceutical composition consists of a tablet that includes Compound 1 Amorphous Form in an amount ranging from 25 mg to 200 mg, for example, 25 mg, or 50 mg, or 75 mg, or 100 mg, or 150 mg, or 200 mg and one or more excipients (e.g., a filler, a disintegrant, a surfactant, a glidant, a colorant, a lubricant, or any combination thereof), each of which is described above and in the Examples below, wherein the tablet has a dissolution of from about 50% to about 100% (e.g., from about 55% to about 95% or from about 60% to about 90%) in about 30 minutes.

In one embodiment, the tablet comprises a composition comprising at least about 10 mg (e.g., at least about 25 mg, at least about 30 mg, at least about 40 mg, or at least about 50 mg) of Compound 1 Amorphous Form; and one or more excipients from: a filler, a disintegrant, a surfactant, a glidant, and a lubricant. In another embodiment, the tablet comprises a composition comprising at least about 10 mg (e.g., at least about 25 mg, at least about 30 mg, at least about 40 mg, at least about 50 mg, at least about 100 mg, or at least 150 mg) of Compound 1 Amorphous Form and one or more excipients from: a filler, a disintegrant, a surfactant, a glidant, and a lubricant.

Dissolution can be measured with a standard USP Type II apparatus that employs a dissolution media of 0.1% CTAB dissolved in 900 mL of DI water, buffered at pH 6.8 with 50 mM potassium phosphate monoasic, stirring at about 50-75 rpm at a temperature of about 37° C. A single experimental tablet is tested in each test vessel of the apparatus. Dissolution can also be measured with a standard USP Type II apparatus that employs a dissolution media of 0.7% sodium lauryl sulfate dissolved in 900 mL of 50 mM sodium phosphate buffer (pH 6.8), stirring at about 65 rpm at a temperature of about 37° C. A single experimental tablet is tested in each test vessel of the apparatus. Dissolution can also be measured with a standard USP Type II apparatus that employs a dissolution media of 0.5% sodium lauryl sulfate dissolved in 900 mL of 50 mM sodium phosphate buffer (pH 6.8), stirring at about 65 rpm at a temperature of about 37° C. A single experimental tablet is tested in each test vessel of the apparatus.

Methods of Preparing Compound 1 Amorphous Form and Compound 1 Form A

Compound 1 is the starting point and in one embodiment can be prepared by coupling an acid chloride moiety with an amine moiety according to Schemes 1-4.

Scheme 1. Synthesis of the acid chloride moiety.

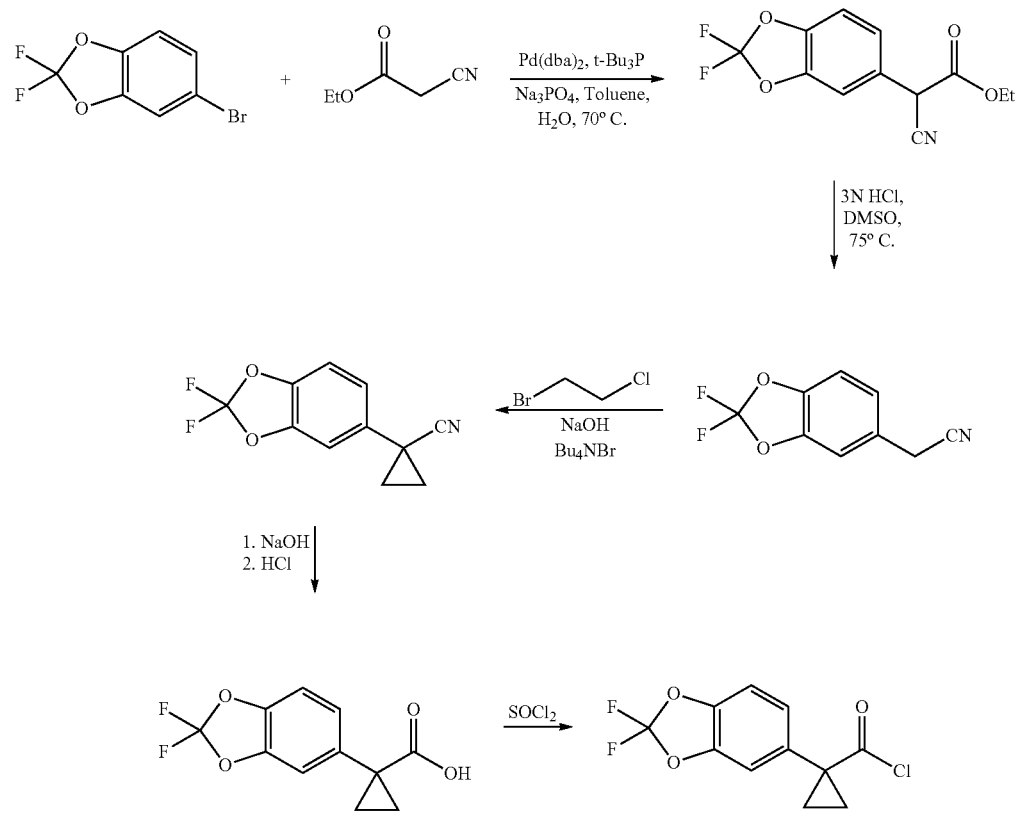

Scheme 2. Synthesis of acid chloride moiety-alternative synthesis.

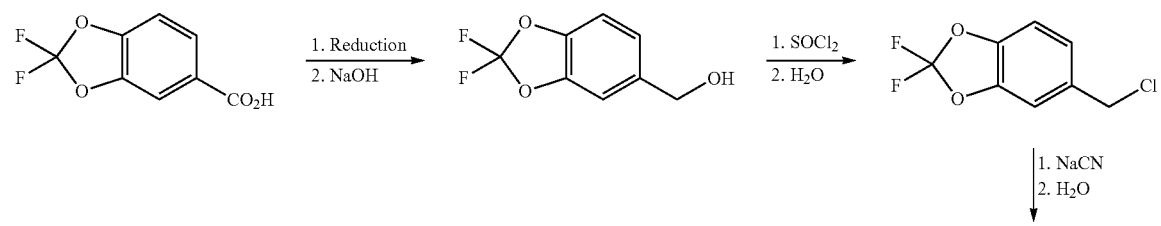

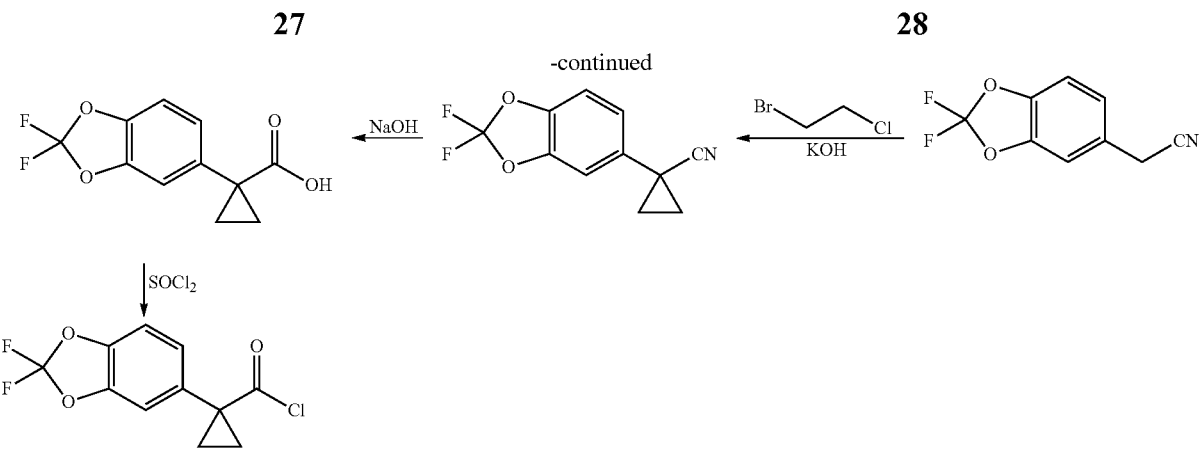
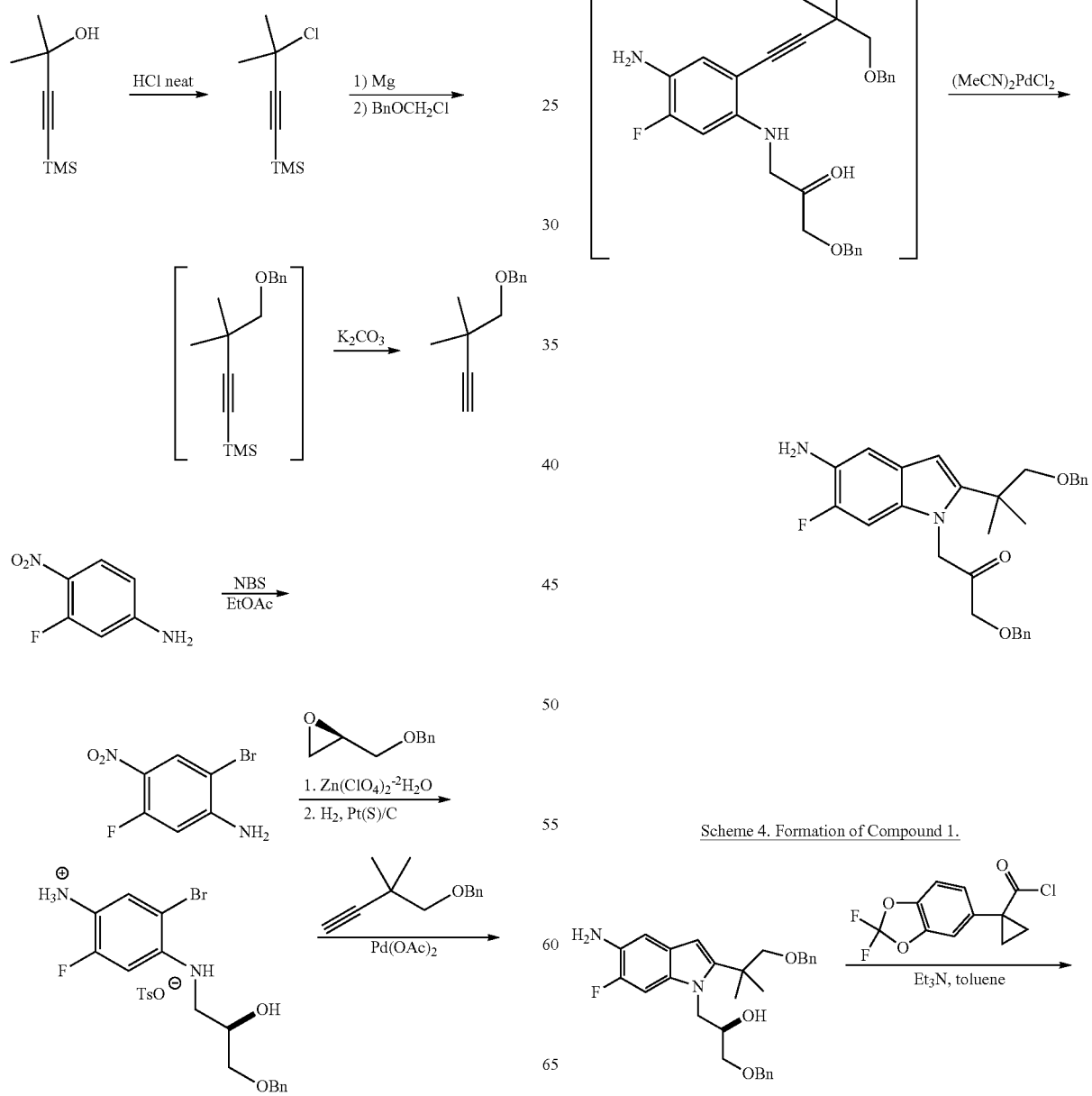

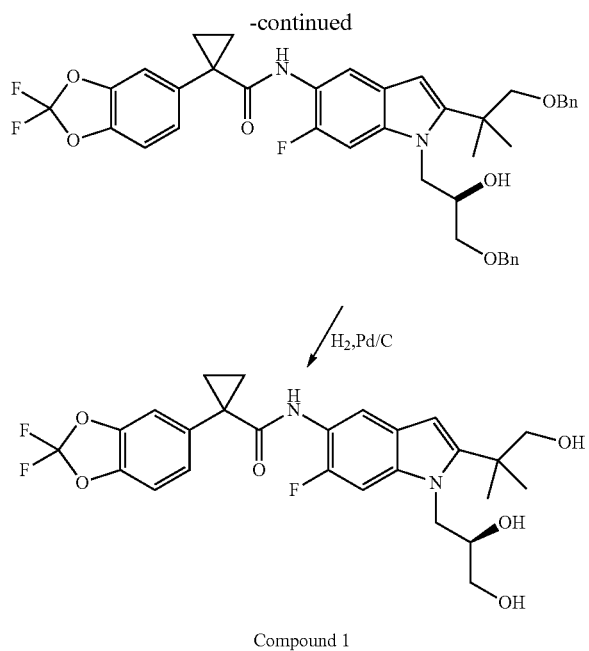

Compound 1

Methods of Preparing Compound 1 Amorphous Form

Starting from Compound 1, or even a crystalline form of Compound 1, Compound 1 Amorphous Form may be prepared by rotary evaporation or by spray dry methods.

Dissolving Compound 1 in an appropriate solvent like methanol and rotary evaporating the methanol to leave a foam produces Compound 1 Amorphous Form. In some embodiments, a warm water bath is used to expedite the evaporation.

Compound 1 Amorphous Form may also be prepared from Compound 1 using spray dry methods. Spray drying is a process that converts a liquid feed to a dried particulate form. Optionally, a secondary drying process such as fluidized bed drying or vacuum drying, may be used to reduce residual solvents to pharmaceutically acceptable levels. Typically, spray drying involves contacting a highly dispersed liquid suspension or solution, and a sufficient volume of hot air to produce evaporation and drying of the liquid droplets. The preparation to be spray dried can be any solution, coarse suspension, slurry, colloidal dispersion, or paste that may be atomized using the selected spray drying apparatus. In a standard procedure, the preparation is sprayed into a current of warm filtered air that evaporates the solvent and conveys the dried product to a collector (e.g. a cyclone). The spent air is then exhausted with the solvent, or alternatively the spent air is sent to a condenser to capture and potentially recycle the solvent. Commercially available types of apparatus may be used to conduct the spray drying. For example, commercial spray dryers are manufactured by Buchi Ltd. And Niro (e.g., the PSD line of spray driers manufactured by Niro) (see, US 2004/0105820; US 2003/0144257).

Spray drying typically employs solid loads of material from about 3% to about 30% by weight, (i.e., drug and excipients), for example about 4% to about 20% by weight, preferably at least about 10%. In general, the upper limit of solid loads is governed by the viscosity of (e.g., the ability to pump) the resulting solution and the solubility of the components in the solution. Generally, the viscosity of the solution can determine the size of the particle in the resulting powder product.

Techniques and methods for spray drying may be found in Perry's Chemical Engineering Handbook, 6$^{th}$ Ed., R. H. Perry, D. W. Green & J. O. Maloney, eds.), McGraw-Hill book co. (1984); and Marshall "Atomization and Spray-Drying" 50, Chem. Eng. Prog. Monogr. Series 2 (1954). In general, the spray drying is conducted with an inlet temperature of from about 60° C. to about 200° C., for example, from about 95° C. to about 185° C., from about 110° C. to about 182° C., from about 96° C. to about 180° C., e.g., about 145° C. The spray drying is generally conducted with an outlet temperature of from about 30° C. to about 90° C., for example from about 40° C. to about 80° C., about 45° C. to about 80° C. e.g., about 75° C. The atomization flow rate is generally from about 4 kg/h to about 12 kg/h, for example, from about 4.3 kg/h to about 10.5 kg/h, e.g., about 6 kg/h or about 10.5 kg/h. The feed flow rate is generally from about 3 kg/h to about 10 kg/h, for example, from about 3.5 kg/h to about 9.0 kg/h, e.g., about 8 kg/h or about 7.1 kg/h. The atomization ratio is generally from about 0.3 to 1.7, e.g., from about 0.5 to 1.5, e.g., about 0.8 or about 1.5.

Removal of the solvent may require a subsequent drying step, such as tray drying, fluid bed drying (e.g., from about room temperature to about 100° C.), vacuum drying, microwave drying, rotary drum drying or biconical vacuum drying (e.g., from about room temperature to about 200° C.).

In one embodiment, the solid dispersion is fluid bed dried.

In one process, the solvent includes a volatile solvent, for example a solvent having a boiling point of less than about 100° C. In some embodiments, the solvent includes a mixture of solvents, for example a mixture of volatile solvents or a mixture of volatile and non-volatile solvents. Where mixtures of solvents are used, the mixture can include one or more non-volatile solvents, for example, where the non-volatile solvent is present in the mixture at less than about 15%, e.g., less than about 12%, less than about 10%, less than about 8%, less than about 5%, less than about 3%, or less than about 2%.

Preferred solvents are those solvents where Compound 1 has a solubility of at least about 10 mg/ml, (e.g., at least about 15 mg/ml, 20 mg/ml, 25 mg/ml, 30 mg/ml, 35 mg/ml, 40 mg/ml, 45 mg/ml, 50 mg/ml, or greater). More preferred solvents include those where Compound 1 has a solubility of at least about 20 mg/ml.

Exemplary solvents that could be tested include acetone, cyclohexane, dichloromethane, N,N-dimethylacetamide (DMA), N,N-dimethylformamide (DMF), 1,3-dimethyl-2-imidazolidinone (DMI), dimethyl sulfoxide (DMSO), dioxane, ethyl acetate, ethyl ether, glacial acetic acid (HAc), methyl ethyl ketone (MEK), N-methyl-2-pyrrolidinone (NMP), methyl tert-butyl ether (MTBE), tetrahydrofuran (THF), pentane, acetonitrile, methanol, ethanol, isopropyl alcohol, isopropyl acetate, and toluene. Exemplary co-solvents include acetone/DMSO, acetone/DMF, acetone/water, MEK/water, THF/water, dioxane/water. In a two solvent system, the solvents can be present in of from about 0.1% to about 99.9%. In some preferred embodiments, water is a co-solvent with acetone where water is present from about 0.1% to about 15%, for example about 9% to about 11%, e.g., about 10%. In some preferred embodiments, water is a co-solvent with MEK where water is present from about 0.1% to about 15%, for example about 9% to about 11%, e.g., about 10%. In some embodiments the solvent solution include three solvents. For example, acetone and water can be mixed with a third solvent such as DMA, DMF, DMI, DMSO, or HAc. In instances where amorphous Compound 1 is a component of a solid amorphous dispersion, preferred solvents dissolve both Compound 1 and the polymer. Suitable solvents include those described above, for example, MEK, acetone, water, methanol, and mixtures thereof.

The particle size and the temperature drying range may be modified to prepare an optimal solid dispersion. As would be appreciated by skilled practitioners, a small particle size would lead to improved solvent removal. Applicants have found however, that smaller particles can lead to fluffy particles that, under some circumstances do not provide optimal solid dispersions for downstream processing such as tabletting. At higher temperatures, crystallization or chemical degradation of Compound 1 may occur. At lower temperatures, a sufficient amount of the solvent may not be removed. The methods herein provide an optimal particle size and an optimal drying temperature.

In general, particle size is such that D10 (μm) is less than about 5, e.g., less than about 4.5, less than about 4.0, or less than about 3.5, D50 (μm) is generally less than about 17, e.g., less than about 16, less than about 15, less than about 14, less than about 13, and D90 (μm) is generally less than about 175, e.g., less than about 170, less than about 170, less than about 150, less than about 125, less than about 100, less than about 90, less than about 80, less than about 70, less than about 60, or less than about less than about 50. In general bulk density of the spray dried particles is from about 0.08 g/cc to about 0.20 g/cc, e.g., from about 0.10 to about 0.15 g/cc, e.g., about 0.11 g/cc or about 0.14 g/cc. Tap density of the spray dried particles generally ranges from about 0.08 g/cc to about 0.20 g/cc, e.g., from about 0.10 to about 0.15 g/cc, e.g., about 0.11 g/cc or about 0.14 g/cc, for 10 taps; 0.10 g/cc to about 0.25 g/cc, e.g., from about 0.11 to about 0.21 g/cc, e.g., about 0.15 g/cc, about 0.19 g/cc, or about 0.21 g/cc for 500 taps; 0.15 g/cc to about 0.27 g/cc, e.g., from about 0.18 to about 0.24 g/cc, e.g., about 0.18 g/cc, about 0.19 g/cc, about 0.20 g/cc, or about 0.24 g/cc for 1250 taps; and 0.15 g/cc to about 0.27 g/cc, e.g., from about 0.18 to about 0.24 g/cc, e.g., about 0.18 g/cc, about 0.21 g/cc, about 0.23 g/cc, or about 0.24 g/cc for 2500 taps.

Polymers

Solid dispersions including Compound 1 Amorphous Form and a polymer (or solid state carrier) also are included herein. For example, Compound 1 is present as an amorphous compound as a component of a solid amorphous dispersion. The solid amorphous dispersion, generally includes Compound 1 and a polymer. Exemplary polymers include cellulosic polymers such as HPMC or HPMCAS and pyrrolidone containing polymers such as PVP/VA. In some embodiments, the solid amporphous dispersion includes one or more additional exipients, such as a surfactant.

In one embodiment, a polymer is able to dissolve in aqueous media. The solubility of the polymers may be pH-independent or pH-dependent. The latter include one or more enteric polymers. The term "enteric polymer" refers to a polymer that is preferentially soluble in the less acidic environment of the intestine relative to the more acid environment of the stomach, for example, a polymer that is insoluble in acidic aqueous media but soluble when the pH is above 5-6. An appropriate polymer should be chemically and biologically inert. In order to improve the physical stability of the solid dispersions, the glass transition temperature ($T_g$) of the polymer should be as high as possible. For example, preferred polymers have a glass transition temperature at least equal to or greater than the glass transition temperature of the drug (i.e., Compound 1). Other preferred polymers have a glass transition temperature that is within about 10 to about 15° C. of the drug (i.e., Compound 1). Examples of suitable glass transition temperatures of the polymers include at least about 90° C., at least about 95° C., at least about 100° C., at least about 105° C., at least about 110° C., at least about 115° C., at least about 120° C., at least about 125° C., at least about 130° C., at least about 135° C., at least about 140° C., at least about 145° C., at least about 150° C., at least about 155° C., at least about 160° C., at least about 165° C., at least about 170° C., or at least about 175° C. (as measured under dry conditions). Without wishing to be bound by theory, it is believed that the underlying mechanism is that a polymer with a higher $T_g$ generally has lower molecular mobility at room temperature, which can be a crucial factor in stabilizing the physical stability of the amorphous solid dispersion.

Additionally, the hygroscopicity of the polymers should be as low, e.g., less than about 10%. For the purpose of comparison in this application, the hygroscopicity of a polymer or composition is characterized at about 60% relative humidity. In some preferred embodiments, the polymer has less than about 10% water absorption, for example less than about 9%, less than about 8%, less than about 7%, less than about 6%, less than about 5%, less than about 4%, less than about 3%, or less than about 2% water absorption. The hygroscopicity can also affect the physical stability of the solid dispersions. Generally, moisture adsorbed in the polymers can greatly reduce the $T_g$ of the polymers as well as the resulting solid dispersions, which will further reduce the physical stability of the solid dispersions as described above.

In one embodiment, the polymer is one or more water-soluble polymer(s) or partially water-soluble polymer(s). Water-soluble or partially water-soluble polymers include but are not limited to, cellulose derivatives (e.g., hydroxypropylmethylcellulose (HPMC), hydroxypropylcellulose (HPC)) or ethylcellulose; polyvinylpyrrolidones (PVP); polyethylene glycols (PEG); polyvinyl alcohols (PVA); acrylates, such as polymethacrylate (e.g., Eudragit® E); cyclodextrins (e.g., β-cyclodextin) and copolymers and derivatives thereof, including for example PVP-VA (polyvinylpyrollidone-vinyl acetate).

In some embodiments, the polymer is hydroxypropylmethylcellulose (HPMC), such as HPMC E50, HPMCE15, or HPMC60SH50).

As discussed herein, the polymer can be a pH-dependent enteric polymer. Such pH-dependent enteric polymers include, but are not limited to, cellulose derivatives (e.g., cellulose acetate phthalate (CAP)), hydroxypropyl methyl cellulose phthalates (HPMCP), hydroxypropyl methyl cellulose acetate succinate (HPMCAS), carboxymethylcellulose (CMC) or a salt thereof (e.g., a sodium salt such as (CMC-Na)); cellulose acetate trimellitate (CAT), hydroxypropyl cellulose acetate phthalate (HPCAP), hydroxypropylmethyl-cellulose acetate phthalate (HPMCAP), and methylcellulose acetate phthalate (MCAP), or polymethacrylates (e.g., Eudragit® S). In some embodiments, the polymer is hydroxypropyl methyl cellulose acetate succinate (HPMCAS). In some embodiments, the polymer is hydroxypropyl methyl cellulose acetate succinate HG grade (HPMCAS-HG).

In yet another embodiment, the polymer is a polyvinylpyrrolidone co-polymer, for example, avinylpyrrolidone/vinyl acetate co-polymer (PVP/VA).

In embodiments where Compound 1 forms a solid dispersion with a polymer, for example with an HPMC, HPMCAS, or PVP/VA polymer, the amount of polymer relative to the total weight of the solid dispersion ranges from about 0.1% to 99% by weight. Unless otherwise specified, percentages of drug, polymer and other excipients as described within a dispersion are given in weight percentages. The amount of polymer is typically at least about 20%, and preferably at least about 30%, for example, at least about 35%, at least about 40%, at least about 45%, or about 50% (e.g., 49.5%). The amount is typically about 99% or less, and preferably about 80% or less, for example about 75% or less, about 70% or less, about 65% or less, about 60% or less, or about 55% or less. In one embodiment, the polymer is in an amount of up to about 50% of the total weight of the dispersion (and even more specifically, between about 40% and 50%, such as about 49%, about 49.5%, or about 50%). HPMC and HPMCAS are available in a variety of grades from ShinEtsu, for example, HPMCAS is available in a number of varieties, including AS-LF, AS-MF, AS-HF, AS-LG, AS-MG, AS-HG. Each of these grades vary with the percent substitution of acetate and succinate.

In some embodiments, Compound 1 and polymer are present in roughly equal amounts, for example each of the polymer and the drug make up about half of the percentage weight of the dispersion. For example, the polymer is present in about 49.5% and the drug is present in about 50%.

In some embodiments, Compound 1 and the polymer combined represent 1% to 20% w/w total solid content of the non-solid dispersion prior to spray drying. In some embodiments, Compound 1 and the polymer combined represent 5% to 15% w/w total solid content of the non-solid dispersion prior to spray drying. In some embodiments, Compound 1 and the polymer combined represent about 11% w/w total solid content of the non-solid dispersion prior to spray drying.

In some embodiments, the dispersion further includes other minor ingredients, such as a surfactant (e.g., SLS). In some embodiments, the surfactant is present in less than about 10% of the dispersion, for example less than about 9%, less than about 8%, less than about 7%, less than about 6%, less than about 5%, less than about 4%, less than about 3%, less than about 2%, about 1%, or about 0.5%.

In embodiments including a polymer, the polymer should be present in an amount effective for stabilizing the solid dispersion. Stabilizing includes inhibiting or preventing, the crystallization of Compound 1. Such stabilizing would inhibit the conversion Compound 1 from amorphous to crystalline form. For example, the polymer would prevent at least a portion (e.g., about 5%, about 10%, about 15%, about 20%, about 25%, about 30%, about 35%, about 40%, about 45%, about 50%, about 55%, about 60%, about 65%, about 70%, about 75%, or greater) of Compound 1 from converting from an amorphous to a crystalline form. Stabilization can be measured, for example, by measuring the glass transition temperature of the solid dispersion, measuring the rate of relaxation of the amorphous material, or by measuring the solubility or bioavailability of Compound 1.

Suitable polymers for use in combination with Compound 1, for example to form a solid dispersion such as an amorphous solid dispersion, should have one or more of the following properties:

The glass transition temperature of the polymer should have a temperature of no less than about 10-15° C. lower than the glass transition temperature of Compound 1. Preferably, the glass transition temperature of the polymer is greater than the glass transition temperature of Compound 1, and in general at least 50° C. higher than the desired storage temperature of the drug product. For example, at least about 100° C., at least about 105° C., at least about 105° C., at least about 110° C., at least about 120° C., at least about 130° C., at least about 140° C., at least about 150° C., at least about 160° C., at least about 160° C., or greater.

The polymer should be relatively non-hygroscopic. For example, the polymer should, when stored under standard conditions, absorb less than about 10% water, for example, less than about 9%, less than about 8%, less than about 7%, less than about 6%, or less than about 5%, less than about 4%, or less than about 3% water. Preferably the polymer will, when stored under standard conditions, be substantially free of absorbed water.

The polymer should have similar or better solubility in solvents suitable for spray drying processes relative to that of Compound 1. In preferred embodiments, the polymer will dissolve in one or more of the same solvents or solvent systems as Compound 1. It is preferred that the polymer is soluble in at least one non-hydroxy containing solvent such as methylene chloride, acetone, or a combination thereof.

The polymer, when combined with Compound 1, for example in a solid dispersion or in a liquid suspension, should increase the solubility of Compound 1 in aqueous and physiologically relative media either relative to the solubility of Compound 1 in the absence of polymer or relative to the solubility of Compound 1 when combined with a reference polymer. For example, the polymer could increase the solubility of amorphous Compound 1 by reducing the amount of amorphous Compound 1 that converts to crystalline Compound 1, either from a solid amorphous dispersion or from a liquid suspension.

The polymer should decrease the relaxation rate of the amorphous substance.

The polymer should increase the physical and/or chemical stability of Compound 1.

The polymer should improve the manufacturability of Compound 1.

The polymer should improve one or more of the handling, administration or storage properties of Compound 1.

The polymer should not interact unfavorably with other pharmaceutical components, for example excipients.

The suitability of a candidate polymer (or other component) can be tested using the spray drying methods (or other methods) described herein to form an amorphous composition. The candidate composition can be compared in terms of stability, resistance to the formation of crystals, or other properties, and compared to a reference preparation, e.g., a preparation of neat amorphous Compound 1 or crystalline Compound 1. For example, a candidate composition could be tested to determine whether it inhibits the time to onset of solvent mediated crystallization, or the percent conversion at a given time under controlled conditions, by at least 50%, 75%, 100%, or 110% as well as the reference preparation, or a candidate composition could be tested to determine if it has improved bioavailability or solubility relative to crystalline Compound 1.

Surfactants

A solid dispersion or other composition may include a surfactant. A surfactant or surfactant mixture would generally decrease the interfacial tension between the solid dispersion and an aqueous medium. An appropriate surfactant or surfactant mixture may also enhance aqueous solubility and bioavailability of Compound 1 from a solid dispersion. The surfactants for use in connection with the present invention include, but are not limited to, sorbitan fatty acid esters (e.g., Spans®), polyoxyethylene sorbitan fatty acid esters (e.g., Tweens®), sodium lauryl sulfate (SLS), sodium dodecylbenzene sulfonate (SDBS) dioctyl sodium sulfosuccinate (Docusate), dioxycholic acid sodium salt (DOSS), Sorbitan Monostearate, Sorbitan Tristearate, hexadecyltrimethyl ammonium bromide (HTAB), Sodium N-lauroylsarcosine, Sodium Oleate, Sodium Myristate, Sodium Stearate, Sodium Palmitate, Gelucire 44/14, ethylenediamine tetraacetic acid (EDTA), Vitamin E d-alpha tocopheryl polyethylene glycol 1000 succinate (TPGS), Lecithin, MW 677-692, Glutanic acid monosodium monohydrate, Labrasol, PEG 8 caprylic/capric glycerides, Transcutol, diethylene glycol monoethyl ether, Solutol HS-15, polyethylene glycol/hydroxystearate, Taurocholic Acid, Pluronic F68, Pluronic F108, and Pluronic F127 (or any other polyoxyethylene-polyoxypropylene co-polymers (Pluronics®) or saturated polyglycolized glycerides (Gelucirs®)). Specific example of such surfactants that may be used in connection with this invention include, but are not limited to, Span 65, Span 25, Tween 20, Capryol 90, Pluronic F108, sodium lauryl sulfate (SLS), Vitamin E TPGS, pluronics and copolymers. SLS is generally preferred.

The amount of the surfactant (e.g., SLS) relative to the total weight of the solid dispersion may be between 0.1-15%. Preferably, it is from about 0.5% to about 10%, more preferably from about 0.5 to about 5%, e.g., about 0.5 to 4%, about 0.5 to 3%, about 0.5 to 2%, about 0.5 to 1%, or about 0.5%.

In certain embodiments, the amount of the surfactant relative to the total weight of the solid dispersion is at least about 0.1%, preferably about 0.5%. In these embodiments, the surfactant would be present in an amount of no more than about 15%, and preferably no more than about 12%, about 11%, about 10%, about 9%, about 8%, about 7%, about 6%, about 5%, about 4%, about 3%, about 2% or about 1%. An embodiment wherein the surfactant is in an amount of about 0.5% by weight is preferred.

Candidate surfactants (or other components) can be tested for suitability for use in the invention in a manner similar to that described for testing polymers.

Methods for Forming Compound 1 Form A

In one embodiment, Compound 1 Form A is prepared by slurrying Compound 1 in an appropriate solvent for an effective amount of time. In another embodiment, the appropriate solvent is ethyl acetate, dichloromethane, MTBE, isopropyl acetate, various ratios of water/ethanol solutions, various ratios of water/acetonitrile solutions, various ratios of water/methanol solutions, or various ratios of water/isopropyl alcohol solutions. For example, various ratios of water/ethanol solutions include water/ethanol 1:9 (vol/vol), water/ethanol 1:1 (vol/vol), and water/ethanol 9:1 (vol/vol). Various ratios of water/acetonitrile solutions include water/acetonitrile 1:9 (vol/vol), water/acetonitrile 1:1 (vol/vol), and water/acetonitrile 9:1 (vol/vol). Various ratios of water/methanol solutions include water/methanol 1:9 (vol/vol), water/methanol 1:1 (vol/vol), and water/methanol 9:1 (vol/vol). Various ratios of water/isopropyl alcohol solutions include water/isopropyl alcohol 1:9 (vol/vol), water/isopropyl alcohol 1:1 (vol/vol), and water/isopropyl alcohol 9:1 (vol/vol).

Generally, about 40 mg of Compound 1 is slurred in about 1.5 ml of an appropriate solvent (target concentration at 26.7 mg/ml) at room temperature for an effective amount of time. In some embodiments, the effective amount of time is about 24 hours to about 2 weeks. In some embodiments, the effective amount of time is about 24 hours to about 1 week. In some embodiments, the effective amount of time is about 24 hours to about 72 hours. The solids are then collected.

In another embodiment, Compound 1 Form A is prepared by dissolving Compound 1 in an appropriate solvent and then evaporating the solvent. In one embodiment, the appropriate solvent is one in which Compound 1 has a solubility of greater than 20 mg/ml. For example, these solvents include acetonitrile, methanol, ethanol, isopropyl alcohol, acetone, and the like.

Generally, Compound 1 is dissolved in an appropriate solvent, filtered, and then left for either slow evaporation or fast evaporation. An example of slow evaporation is covering a container, such as a vial, comprising the Compound 1 solution with parafilm having one hole poked in it. An example of fast evaporation is leaving a container, such as a vial, comprising the Compound 1 solution uncovered. The solids are then collected.

In another aspect, the invention features a process of preparing Compound 1 Form A comprising dissolving Compound 1 in a first solvent and adding a second solvent that Compound 1 has poor solubility in (solubility <1 mg/ml). For example, the first solvent may be a solvent that Compound 1 has greater than 20 mg/ml solubility in, e.g. ethyl acetate, ethanol, isopropyl alcohol, or acetone. The second solvent may be, for example, heptane or water.

Generally, Compound 1 is dissolved in the first solvent and filtered to remove any seed crystals. The second solvent is added slowly while stirring. The solids are precipitated and collected by filtering.

Methods for Preparing the Pharmaceutical Compositions

The dosage unit forms of the invention can be produced by compacting or compressing an admixture or composition, for example, a powder or granules, under pressure to form a stable three-dimensional shape (e.g., a tablet). As used herein, "tablet" includes compressed pharmaceutical dosage unit forms of all shapes and sizes, whether coated or uncoated.

The expression "dosage unit form" as used herein refers to a physically discrete unit of agent appropriate for the patient to be treated. In general, a compacted mixture has a density greater than that of the mixture prior to compaction. A dosage unit form of the invention can have almost any shape including concave and/or convex faces, rounded or angled corners, and a rounded to rectilinear shape. In some embodiments, the compressed dosage forms of the invention comprise a rounded tablet having flat faces. The solid pharmaceutical dosage forms of the invention can be prepared by any compaction and compression method known by persons of ordinary skill in the art of forming compressed solid pharmaceutical dosage forms. In particular embodiments, the formulations provided herein may be prepared using conventional methods known to those skilled in the field of pharmaceutical formulation, as described, e.g., in pertinent textbooks. See, e.g., Remington: The Science and Practice of Pharmacy, 21st Ed., Lippincott Williams & Wilkins, Baltimore, Md. (2003); Ansel et al., Pharmaceutical Dosage Forms And Drug Delivery Systems, 7th Edition, Lippincott Williams & Wilkins, (1999); The Handbook of Pharmaceutical Excipients, $4^{th}$ edition, Rowe et al., Eds., American Pharmaceuticals Association (2003); Gibson, Pharmaceutical Preformulation And Formulation, CRC Press (2001), these references hereby incorporated herein by reference in their entirety.

Granulation and Compression

In some embodiments, solid forms, including powders comprising the active agent, Compound 1 Amorphous Form, and the included pharmaceutically acceptable excipients (e.g. filler, disintegrant, surfactant, glidant, lubricant, or any combination thereof) can be subjected to a dry granulation process. The dry granulation process causes the powder to agglomerate into larger particles having a size suitable for further processing. Dry granulation can improve the flowability of a mixture in order to be able to produce tablets that comply with the demand of mass variation or content uniformity.

Formulations as described herein may be produced using one or more mixing and dry granulations steps. The order and the number of the mixing and granulation steps do not seem to be critical. However, at least one of the excipients and Compound 1 can be been subject to dry granulation or wet high shear granulation before compression into tablets. Dry granulation of Compound 1 Amorphous Form and the excipients made together prior to tablet compression seem, surprisingly, to be a simple, inexpensive and efficient way of providing close physical contact between the ingredients of the present compositions and formulations and thus results in a tablet formulation with good stability properties. Dry granulation can be carried out by a mechanical process, which transfers energy to the mixture without any use of any liquid substances (neither in the form of aqueous solutions, solutions based on organic solutes, or mixtures thereof) in contrast to wet granulation processes, also contemplated herein. Generally, the mechanical process requires compaction such as the one provided by roller compaction. An example of an alternative method for dry granulation is slugging.

In some embodiments, roller compaction is a granulation process comprising highly intensive mechanical compacting of one or more substances. In some embodiments, a pharmaceutical composition comprising an admixture of powders is pressed, that is roller compacted, between 2 counter rotating rollers to make a solid sheet which is subsequently crushed in a sieve to form a particulate matter. In this particulate matter, a close mechanical contact between the ingredients can be obtained. An example of roller compaction equipment is Minipactor® a Gerteis 3W-Polygran from Gerteis Maschinen+Processengineering AG.

In some embodiments, tablet compression according to the invention can occur without any use of any liquid substances (neither in the form of aqueous solutions, solutions based on organic solutes, or mixtures thereof), i.e. a dry granulation process. In a typical embodiment the resulting core or tablet has a compressive strength in the range of 1 to 15 kP; such as 1.5 to 12.5 kP, preferably in the range of 2 to 10 kP.

Brief Manufacturing Procedure

In some embodiments, the ingredients are weighed according to the formula set herein. Next, all of the intragranular ingredients are sifted and mixed well. The ingredients can be lubricated with a suitable lubricant, for example, magnesium stearate. The next step can comprise compaction/slugging of the powder admixture and sized ingredients. Next, the compacted or slugged blends are milled into granules and sifted to obtain the desired size. Next, the granules can be further lubricated with, for example, magnesium stearate. Next the granular composition of the invention can be compressed on suitable punches into various pharmaceutical formulations in accordance with the invention. Optionally the tablets can be coated with a film, colorant or other coating.

Another aspect of the invention provides a method for producing a pharmaceutical composition comprising providing an admixture of a composition comprising Compound 1 Amorphous Form and one or more excipients selected from: a filler, a glidant, a surfactant, a lubricant, a disintegrant, and compressing the composition into a tablet having a dissolution of at least about 50% in about 30 minutes.

In another embodiment, a wet granulation process is performed to yield the pharmaceutical formulation of the invention from an admixture of powdered and liquid ingredients. For example, a pharmaceutical composition comprising an admixture of a composition comprising Compound 1 Amorphous Form and one or more excipients selected from: a filler, a glidant, a surfactant, a lubricant, a disintegrant, are weighed as per the formula set herein. Next, all of the intragranular ingredients are sifted and mixed in a high shear or low shear granulator using water or water with a surfactant or water with a binder or water with a surfactant and a binder to granulate the powder blend. A fluid other than water can also be used with or without surfactant and/or binder to granulate the powder blend. Next, the wet granules can optionally be milled using a suitable mill. Next, water may optionally be removed from the admixture by drying the ingredients in any suitable manner. Next, the dried granules can optionally be milled to the required size. Next, extra granular excipients can be added by blending (for example a filler, and a disintegrant). Next, the sized granules can be further lubricated with magnesium stearate and a disintegrant, for example, croscarmellose sodium. Next the granular composition of the invention can be sifted for sufficient time to obtain the correct size and then compressed on suitable punches into various pharmaceutical formulations in accordance with the invention. Optionally, the tablets can be coated with a film, colorant or other coating.

Each of the ingredients of this exemplary admixture is described above and in the Examples below. Furthermore, the admixture can comprise optional additives, such as, one or more colorants, one or more flavors, and/or one or more fragrances as described above and in the Examples below. In some embodiments, the relative concentrations (e.g., wt %) of each of these ingredients (and any optional additives) in the admixture are also presented above and in the Examples below. The ingredients constituting the admixture can be provided sequentially or in any combination of additions; and, the ingredients or combination of ingredients can be provided in any order. In one embodiment, the lubricant is the last component added to the admixture.

In another embodiment, the admixture comprises a composition of Compound 1 Amorphous Form, and any one or more of the excipients; a glidant, a surfactant, a lubricant, a disintegrant, and a filler, wherein each of these ingredients is provided in a powder form (e.g., provided as particles having a mean or average diameter, measured by light scattering, of 250 µm or less (e.g., 150 m or less, 100 µm or less, 50 µm or less, 45 µm or less, 40 µm or less, or 35 µm or less)). For instance, the admixture comprises a composition of Compound 1 Amorphous Form, a glidant, a surfactant, a lubricant, a disintegrant, and a filler, wherein each of these ingredients is provided in a powder form (e.g., provided as particles having a mean diameter, measured by light scattering, of 250 µm or less (e.g., 150 µm or less, 100 µm or less, 50 µm or less, 45 µm or less, 40 µm or less, or 35 µm or less)). In another example, the admixture comprises a composition of Compound 1 Amorphous Form, a surfactant, a lubricant, a disintegrant, and a filler, wherein each of these ingredients is provided in a powder form (e.g., provided as particles having a mean diameter, measured by light scattering, of 250 µm or less (e.g., 150 µm or less, 100 µm or less, 50 µm or less, 45 µm or less, 40 µm or less, or 35 µm or less))

In another embodiment, the admixture comprises a composition of Compound 1 Amorphous Form, and any combination of: a glidant, a surfactant, a lubricant, a disintegrant, and a filler, wherein each of these ingredients is substantially free of water. Each of the ingredients comprises less than 5 wt % (e.g., less than 2 wt %, less than 1 wt %, less than 0.75 wt %, less than 0.5 wt %, or less than 0.25 wt %) of water by weight of the ingredient. For instance, the admixture comprises a composition of Compound 1 Amorphous Form, a glidant, a surfactant, a lubricant, a disintegrant, and a filler, wherein each of these ingredients is substantially free of water. In some embodiments, each of the ingredients comprises less than 5 wt % (e.g., less than 2 wt %, less than 1 wt %, less than 0.75 wt %, less than 0.5 wt %, or less than 0.25 wt %) of water by weight of the ingredient.

In another embodiment, compressing the admixture into a tablet is accomplished by filling a form (e.g., a mold) with the admixture and applying pressure to admixture. This can be accomplished using a die press or other similar apparatus. In some embodiments, the admixture of Compound 1 Amorphous Form and excipients can be first processed into granular form. The granules can then be sized and compressed into tablets or formulated for encapsulation according to known methods in the pharmaceutical art. It is also noted that the application of pressure to the admixture in the form can be repeated using the same pressure during each compression or using different pressures during the compressions. In another example, the admixture of powdered ingredients or granules can be compressed using a die press that applies sufficient pressure to form a tablet having a dissolution of about 50% or more at about 30 minutes (e.g., about 55% or more at about 30 minutes or about 60% or more at about 30 minutes). For instance, the admixture is compressed using a die press to produce a tablet hardness of at least about 5 kP (at least about 5.5 kP, at least about 6 kP, at least about 7 kP, at least about 10 kP, or at least 15 kP). In some instances, the admixture is compressed to produce a tablet hardness of between about 5 and 20 kP.

In some embodiments, tablets comprising a pharmaceutical composition as described herein can be coated with about 3.0 wt % of a film coating comprising a colorant by weight of the tablet. In certain instances, the colorant suspension or solution used to coat the tablets comprises about 20% w/w of solids by weight of the colorant suspension or solution. In still further instances, the coated tablets can be labeled with a logo, other image or text.

In another embodiment, the method for producing a pharmaceutical composition comprises providing an admixture of a solid forms, e.g. an admixture of powdered and/or liquid ingredients, the admixture comprising Compound 1 Amorphous Form and one or more excipients selected from: a glidant, a surfactant, a lubricant, a disintegrant, and a filler; mixing the admixture until the admixture is substantially homogenous, and compressing or compacting the admixture into a granular form. Then the granular composition comprising Compound 1 Amorphous Form can be compressed into tablets or formulated into capsules as described above or in the Examples below. Alternatively, methods for producing a pharmaceutical composition comprises providing an admixture of Compound 1 Amorphous Form, and one or more excipients, e.g. a glidant, a surfactant, a lubricant, a disintegrant, and a filler; mixing the admixture until the admixture is substantially homogenous, and compressing/compacting the admixture into a granular form using a roller compactor using a dry granulation composition as set forth in the Examples below or alternatively, compressed/compacted into granules using a high shear wet granule compaction process as set forth in the Examples below. Pharmaceutical formulations, for example a tablet as described herein, can be made using the granules prepared incorporating Compound 1 Amorphous Form in addition to the selected excipients described herein.

In some embodiments, the admixture is mixed by stirring, blending, shaking, or the like using hand mixing, a mixer, a blender, any combination thereof, or the like. When ingredients or combinations of ingredients are added sequentially, mixing can occur between successive additions, continuously throughout the ingredient addition, after the addition of all of the ingredients or combinations of ingredients, or any combination thereof. The admixture is mixed until it has a substantially homogenous composition.

In one embodiment, the pharmaceutical compositions of the present invention may be prepared according to the flow chart depicted in FIG. 15.

In another embodiment, the pharmaceutical compositions of the present invention may be prepared according to the flow chart depicted in FIG. 16.

In another embodiment, the pharmaceutical compositions of the present invention may be prepared according to the flow chart depicted in FIG. 17.

In another embodiment, Compound 1 Amorphous Form is in a 50% by wgt. mixture with a polymer and surfactant, the brand of colloidal silica dioxide glidant used is Cabot M5P, the brand of crosscarmelose sodium disintegrant used is AcDiSol, the brand of microcrystalline cellulose filler used is Avicel PH101, and the brand of lactose monohydrate used is Foremost 310. In another embodiment, the Compound 1 Amorphous Form polymer is a hydroxylpropylmethylcellulose (HPMC) and the surfactant is sodium lauryl sulfate. In another embodiment, the Compound 1 Amorphous Form polymer is hydroxypropylmethylcellulose acetate succinate (HPMCAS). In another embodiment, the Compound 1 Amorphous Form polymer is hydroxypropylmethylcellulose acetate succinate-high grade (HPMCAS-HG).

In various embodiments, a second therapeutic agent can be formulated together with Compound 1 Amorphous Form to form a unitary or single dose form, for example, a tablet or capsule.

Dosage forms prepared as above can be subjected to in vitro dissolution evaluations according to Test 711 "Dissolution" in United States Pharmacopoeia 29, United States Pharmacopeial Convention, Inc., Rockville, Md., 2005 ("USP"), to determine the rate at which the active substance is released from the dosage forms. The content of active substance and the impurity levels are conveniently measured by techniques such as high performance liquid chromatography (HPLC).

In some embodiments, the invention includes use of packaging materials such as containers and closures of high-density polyethylene (HDPE), low-density polyethylene (LDPE) and or polypropylene and/or glass, glassine foil, aluminum pouches, and blisters or strips composed of aluminum or high-density polyvinyl chloride (PVC), optionally including a desiccant, polyethylene (PE), polyvinylidene dichloride (PVDC), PVC/PE/PVDC, and the like. These package materials can be used to store the various pharmaceutical compositions and formulations in a sterile fashion after appropriate sterilization of the package and its contents using chemical or physical sterilization techniques commonly employed in the pharmaceutical arts.

Methods for Administering the Pharmaceutical Compositions

In one aspect, the pharmaceutical compositions of the invention can be administered to a patient once daily or about every twenty four hours. Alternatively, the pharmaceutical compositions of the invention can be administered to a patient twice daily or about every twelve hours. These pharmaceutical compositions are administered as oral formulations containing about 2.5 mg, 5 mg, 10 mg, 25 mg, 50 mg, 100 mg, 125 mg, 150 mg, 200 mg, or 250 mg of Compound 1 Amorphous Form. In this aspect, in addition to Compound 1 Amorphous Form, the pharmaceutical compositions comprise a filler; a disintegrant; a surfactant; a glidant; and a lubricant.

It will also be appreciated that the compound and pharmaceutically acceptable compositions and formulations of the invention can be employed in combination therapies; that is, Compound 1 Amorphous Form and pharmaceutically acceptable compositions thereof can be co-administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, for example, a CFTR mediated disease, or condition, are known as "appropriate for the disease or condition being treated."

In one embodiment, the additional therapeutic agent is selected from a mucolytic agent, bronchodialator, an antibiotic, an anti-infective agent, an anti-inflammatory agent, a CFTR modulator other than Compound 1 of the invention, or a nutritional agent.

In one embodiment, the additional therapeutic agent is an antibiotic. Exemplary antibiotics useful herein include tobramycin, including tobramycin inhaled powder (TIP), azithromycin, aztreonam, including the aerosolized form of aztreonam, amikacin, including liposomal formulations thereof, ciprofloxacin, including formulations thereof suitable for administration by inhalation, levoflaxacin, including aerosolized formulations thereof, and combinations of two antibiotics, e.g., fosfomycin and tobramycin.

In another embodiment, the additional agent is a mucolyte. Exemplary mucolytes useful herein includes Pulmozyme®.

In another embodiment, the additional agent is a bronchodialator. Exemplary bronchodilators include albuterol, metaprotenerol sulfate, pirbuterol acetate, salmeterol, or tetrabuline sulfate.

In another embodiment, the additional agent is effective in restoring lung airway surface liquid. Such agents improve the movement of salt in and out of cells, allowing mucus in the lung airway to be more hydrated and, therefore, cleared more easily. Exemplary such agents include hypertonic saline, denufosol tetrasodium ([[[(3S,5R)-5-(4-amino-2-oxopyrimidin-1-yl)-3-hydroxyoxolan-2-yl]methoxy-hydroxyphosphoryl][[[(2R,3S,4R,5R)-5-(2,4-dioxopyrimidin-1-yl)-3,4-dihydroxyoxolan-2-yl]methoxy-hydroxyphosphoryl]oxy-hydroxyphosphoryl]hydrogen phosphate), or bronchitol (inhaled formulation of mannitol).

In another embodiment, the additional agent is an anti-inflammatory agent, i.e., an agent that can reduce the inflammation in the lungs. Exemplary such agents useful herein include ibuprofen, docosahexanoic acid (DHA), sildenafil, inhaled glutathione, pioglitazone, hydroxychloroquine, or simavastatin.

In another embodiment, the additional agent is a CFTR modulator other than Compound 1, i.e., an agent that has the effect of modulating CFTR activity. Exemplary such agents include ataluren ("PTC124®"; 3-[5-(2-fluorophenyl)-1,2,4-oxadiazol-3-yl]benzoic acid), sinapultide, lancovutide, depelestat (a human recombinant neutrophil elastase inhibitor), and cobiprostone (7-{(2R, 4aR, 5R, 7aR)-2-[(3 S)-1,1-difluoro-3-methylpentyl]-2-hydroxy-6-oxooctahydrocyclopenta[b]pyran-5-yl}heptanoic acid).

In another embodiment, the additional agent is a nutritional agent. Exemplary nutritional agents include pancrelipase (pancreating enzyme replacement), including Pancrease®, Pancreacarb®, Ultrase®, or Creon®, Liprotomase® (formerly Trizytek®), Aquadeks®, or glutathione inhalation. In one embodiment, the additional nutritional agent is pancrelipase.

In another embodiment, the additional agent is a compound selected from gentamicin, curcumin, cyclophosphamide, 4-phenylbutyrate, miglustat, felodipine, nimodipine, Philoxin B, geniestein, Apigenin, cAMP/cGMP modulators such as rolipram, sildenafil, milrinone, tadalafil, amrinone, isoproterenol, albuterol, and almeterol, deoxyspergualin, HSP 90 inhibitors, HSP 70 inhibitors, proteosome inhibitors such as epoxomicin, lactacystin, etc.

In another embodiment, the additional agent is a compound selected from 3-amino-6-(4-fluoro-phenyl)-5-trifluoromethyl-pyridine-2-carboxylic acid (3,3,3-trifluoro-2-hydroxy-2-methyl-propyl)-amide; 5-amino-6'-methyl-3-trifluoromethyl-[2,3]bipyridinyl-6-carboxylic acid (3,3,3-trifluoro-2-hydroxy-2-methyl-propyl)-amide; 3-amino-6-cyclopropyl-N-(3,3,3-trifluoro-2-hydroxy-2-methylpropyl)-5-(trifluoromethyl)picolinamide; 3-amino-6-methoxy-N-(3,3,3-trifluoro-2-hydroxy-2-(trifluoromethyl)propyl)-5-(trifluoro methyl)picolinamide; 3-amino-6-(4-fluoro-phenyl)-5-trifluoromethyl-pyridine-2-carboxylic acid ((S)-3,3,3-trifluoro-2-hydroxy-2-methyl-propyl)-amide; 3-amino-6-methoxy-5-trifluoromethyl-pyridine-2-carboxylic acid((S-3,3,3-trifluoro-2-hydroxy-2-methyl-propyl)-amide; 3-amino-6-methoxy-5-trifluoromethyl-pyridine-2-carboxylic acid ((R)-3,3,3-trifluoro-2-hydroxy-2-methyl-propyl)-amide; 3-amino-6-(2,4-dichloro-phenyl)-5-trifluoromethyl-pyridine-2-carboxylic acid ((S)-3,3,3-trifluoro-2-hydroxy-2-methyl-propyl)-amide; 3-amino-6-(2,4-dichloro-phenyl)-5-trifluoromethyl-pyridine-2-carboxylic acid ((R)-3,3,3-trifluoro-2-hydroxy-2-methyl-propyl)-amide; 3-amino-6-(4-fluoro-phenyl)-5-trifluoromethyl-pyridine-2-carboxylic acid (2-hydroxy-2-methyl-propyl)-amide; 3-amino-5,6-bis-trifluoromethyl-pyridine-2-carboxylic acid ((S)-3,3,3-trifluoro-2-hydroxy-2-methyl-propyl)-amide; 3-amino-5,6-bis-trifluoromethyl-pyridine-2-carboxylic acid ((R)-3,3,3-trifluoro-2-hydroxy-2-methyl-propyl)-amide; (S)-3-amino-6-ethoxy-N-(3,3,3-trifluoro-2-hydroxy-2-methylpropyl)-5-(trifluoro methyl)picolinamide; 3-amino-6-methoxy-5-trifluoromethyl-pyridine-2-carboxylic acid ((S)-3,3,3-trifluoro-2-hydroxy-2-methyl-propyl)-amide; 3-amino-6-methoxy-5-trifluoromethyl-pyridine-2-carboxylic acid ((R)-3,3,3-trifluoro-2-hydroxy-2-methyl-propyl)-amide; 3-amino-6-(4-fluoro-phenyl)-5-trifluoromethyl-pyridine-2-carboxylic acid (3,3,3-trifluoro-2-hydroxy-2-methyl-propyl)-amide; 3-amino-5,6-bis-trifluoromethyl-pyridine-2-carboxylic acid ((S)-3,3,3-trifluoro-2-hydroxy-2-methyl-propyl)-amide; 3-amino-5,6-bis-trifluoromethyl-pyridine-2-carboxylic acid ((R)-3,3,3-trifluoro-2-hydroxy-2-methyl-propyl)-amide, or pharmaceutically acceptable salts thereof.

In another embodiment, the additional agent is a compound disclosed in U.S. Pat. No. 8,247,436 and International PCT Publication WO 2011113894, incorporated herein in their entirety by reference.

In other embodiments, the additional agent is a compound disclosed in WO 2004028480, WO 2004110352, WO 2005094374, WO 2005120497, or WO 2006101740. In another embodiment, the additional agent is a benzo[c]quinolizinium derivative that exhibits CFTR modulation activity or a benzopyran derivative that exhibits CFTR modulation activity. In another embodiment, the additional agent is a compound disclosed in U.S. Pat. No. 7,202,262, U.S. Pat. No. 6,992,096, US20060148864, US20060148863, US20060035943, US20050164973, WO2006110483, WO2006044456, WO2006044682, WO2006044505, WO2006044503, WO2006044502, or WO2004091502. In another embodiment, the additional agent is a compound disclosed in WO2004080972, WO2004111014, WO2005035514, WO2005049018, WO2006099256, WO2006127588, or WO2007044560. In another embodiment, the additional agent is N-(5-hydroxy-2,4-ditert-butyl-phenyl)-4-oxo-1H-quinoline-3-carboxamide.

In another embodiment, the additional agent is Moli1901 (lancovutide). In another embodiment, the additional agent is P-552-02. In another embodiment, the additional agent is Aerolyitic. In another embodiment, the additional agent is QAU145. In another embodiment, the additional agent is Cayston (aztreonam for inhalation solution). In another embodiment, the additional agent is Arikace (liposomal amikacin). In another embodiment, the additional agent is Ultresa (pancrelipase). In another embodiment, the additional agent is alpha-1-antitrypsin (A1AT or AAT-1).

In one embodiment, 5 to 300 mg of Compound 1 may be administered to a subject in need thereof followed by co-administration of 100 to 300 mg of N-(5-hydroxy-2,4-ditert-butyl-phenyl)-4-oxo-1H-quinoline-3-carboxamide (Compound 2). In these embodiments, the dosage amounts may be achieved by administration of one or more tablets of the invention. Compound 2 may be administered as a pharmaceutical composition comprising Compound 2 and a pharmaceutically acceptable carrier. The duration of administration may continue until amelioration of the disease is achieved or until a subject's physician advises, e.g. duration of administration may be less than a week, 1 week, 2 weeks, 3 weeks, or a month or longer. The co-administration period may be preceded by an administration period of just Compound 1 alone. For example, there could be administration of 100 mg of Compound 1 for 2 weeks followed by co-administration of 150 mg or 250 mg of Compound 2 for 1 additional week.

In one embodiment, 10, 30, 100, or 150 mg of Compound 1 may be administered to a subject in need thereof for 1 week, 2 weeks, 3 weeks, 4 weeks (28 days), or a month or longer.

In one embodiment, 10 mg of Compound 1 may be administered to a subject once a day (QD). In one embodiment, 10 mg of Compound 1 may be administered once a day (QD) to a subject in need thereof followed by co-administration of 50 mg of Compound 2 once a day (QD). In one embodiment, 10 mg of Compound 1 may be administered once a day (QD) to a subject in need thereof followed by co-administration of 50 mg of Compound 2 twice a day (BID). In one embodiment, 10 mg of Compound 1 may be administered once a day (QD) to a subject in need thereof followed by co-administration of 100 mg of Compound 2 once a day (QD). In one embodiment, 10 mg of Compound 1 may be administered once a day (QD) to a subject in need thereof followed by co-administration of 100 mg of Compound 2 twice a day (BID). In one embodiment, 10 mg of Compound 1 may be administered once a day (QD) to a subject in need thereof followed by co-administration of 150 mg of Compound 2 once a day (QD). In one embodiment, 10 mg of Compound 1 may be administered once a day (QD) to a subject in need thereof followed by co-administration of 150 mg of Compound 2 twice a day (BID). In another embodiment, 10 mg of Compound 1 may be administered once a day (QD) to a subject in need thereof followed by co-administration of 250 mg of Compound 2 once a day (QD). In another embodiment, 10 mg of Compound 1 may be administered once a day (QD) to a subject in need thereof followed by co-administration of 250 mg of Compound 2 twice a day (BID). In these embodiments, the dosage amounts may be achieved by administration of one or more tablets of the invention. Compound 2 may be administered as a pharmaceutical composition comprising Compound 2 and a pharmaceutically acceptable carrier. The duration of administration may continue until amelioration of the disease is achieved or until a subject's physician advises, e.g. duration of administration may be less than a week, 1 week, 2 weeks, 3 weeks, or a month or longer. The co-administration period may be preceded by an administration period of just Compound 1 alone. For example, there could be administration of 10 mg of Compound 1 for 2 weeks followed by co-administration of 150 mg or 250 mg of Compound 2 for 1 additional week.

In one embodiment, 30 mg of Compound 1 may be administered to a subject once a day (QD). In one embodiment, 30 mg of Compound 1 may be administered once a day (QD) to a subject in need thereof followed by co-administration of 50 mg of Compound 2 once a day (QD). In one embodiment, 30 mg of Compound 1 may be administered once a day (QD) to a subject in need thereof followed by co-administration of 50 mg of Compound 2 twice a day (BID). In one embodiment, 30 mg of Compound 1 may be administered once a day (QD) to a subject in need thereof followed by co-administration of 100 mg of Compound 2 once a day (QD). In one embodiment, 30 mg of Compound 1 may be administered once a day (QD) to a subject in need thereof followed by co-administration of 100 mg of Compound 2 twice a day (BID). In one embodiment, 30 mg of Compound 1 may be administered once a day (QD) to a subject in need thereof followed by co-administration of 150 mg of Compound 2 once a day (QD). In one embodiment, 30 mg of Compound 1 may be administered once a day (QD) to a subject in need thereof followed by co-administration of 150 mg of Compound 2 twice a day (BID). In another embodiment, 30 mg of Compound 1 may be administered once a day (QD) to a subject in need thereof followed by co-administration of 250 mg of Compound 2 once a day (QD). In another embodiment, 30 mg of Compound 1 may be administered once a day (QD) to a subject in need thereof followed by co-administration of 250 mg of Compound 2 twice a day (BID). In these embodiments, the dosage amounts may be achieved by administration of one or more tablets of the invention. Compound 2 may be administered as a pharmaceutical composition comprising Compound 2 and a pharmaceutically acceptable carrier. The duration of administration may continue until amelioration of the disease is achieved or until a subject's physician advises, e.g. duration of administration may be less than a week, 1 week, 2 weeks, 3 weeks, or a month or longer. The co-administration period may be preceded by an administration period of just Compound 1 alone. For example, there could be administration of 30 mg of Compound 1 for 2 weeks followed by co-administration of 150 mg or 250 mg of Compound 2 for 1 additional week.

In one embodiment, 100 mg of Compound 1 may be administered to a subject once a day (QD). In one embodiment, 100 mg of Compound 1 may be administered once a day (QD) to a subject in need thereof followed by co-administration of 50 mg of Compound 2 once a day (QD). In one embodiment, 100 mg of Compound 1 may be administered once a day (QD) to a subject in need thereof followed by co-administration of 50 mg of Compound 2 twice a day (BID). In one embodiment, 100 mg of Compound 1 may be administered once a day (QD) to a subject in need thereof followed by co-administration of 100 mg of Compound 2 once a day (QD). In one embodiment, 100 mg of Compound 1 may be administered once a day (QD) to a subject in need thereof followed by co-administration of 100 mg of Compound 2 twice a day (BID). In one embodiment, 100 mg of Compound 1 may be administered once a day (QD) to a subject in need thereof followed by co-administration of 150 mg of Compound 2 once a day (QD). In one embodiment, 100 mg of Compound 1 may be administered once a day (QD) to a subject in need thereof followed by co-administration of 150 mg of Compound 2 twice a day (BID). In another embodiment, 100 mg of Compound 1 may be administered once a day (QD) to a subject in need thereof followed by co-administration of 250 mg of Compound 2 once a day (QD). In another embodiment, 100 mg of Compound 1 may be administered once a day (QD) to a subject in need thereof followed by co-administration of 250 mg of Compound 2 twice a day (BID). In these embodiments, the dosage amounts may be achieved by administration of one or more tablets of the invention. Compound 2 may be administered as a pharmaceutical composition comprising Compound 2 and a pharmaceutically acceptable carrier. The duration of administration may continue until amelioration of the disease is achieved or until a subject's physician advises, e.g. duration of administration may be less than a week, 1 week, 2 weeks, 3 weeks, or a month or longer. The co-administration period may be preceded by an administration period of just Compound 1 alone. For example, there could be administration of 100 mg of Compound 1 for 2 weeks followed by co-administration of 150 mg or 250 mg of Compound 2 for 1 additional week.

In one embodiment, 150 mg of Compound 1 may be administered to a subject once a day (QD). In one embodiment, 150 mg of Compound 1 may be administered once a day (QD) to a subject in need thereof followed by co-administration of 50 mg of Compound 2 once a day (QD). In one embodiment, 150 mg of Compound 1 may be administered once a day (QD) to a subject in need thereof followed by co-administration of 50 mg of Compound 2 twice a day (BID). In one embodiment, 150 mg of Compound 1 may be administered once a day (QD) to a subject in need thereof followed by co-administration of 100 mg of Compound 2 once a day (QD). In one embodiment, 150 mg of Compound 1 may be administered once a day (QD) to a subject in need thereof followed by co-administration of 100 mg of Compound 2 twice a day (BID). In one embodiment, 150 mg of Compound 1 may be administered once a day (QD) to a subject in need thereof followed by co-administration of 150 mg of Compound 2 once a day (QD). In one embodiment, 150 mg of Compound 1 may be administered once a day (QD) to a subject in need thereof followed by co-administration of 150 mg of Compound 2 twice a day (BID). In another embodiment, 150 mg of Compound 1 may be administered once a day (QD) to a subject in need thereof followed by co-administration of 250 mg of Compound 2 once a day (QD). In another embodiment, 150 mg of Compound 1 may be administered once a day (QD) to a subject in need thereof followed by co-administration of 250 mg of Compound 2 twice a day (BID). In these embodiments, the dosage amounts may be achieved by administration of one or more tablets of the invention. Compound 2 may be administered as a pharmaceutical composition comprising Compound 2 and a pharmaceutically acceptable carrier. The duration of administration may continue until amelioration of the disease is achieved or until a subject's physician advises, e.g. duration of administration may be less than a week, 1 week, 2 weeks, 3 weeks, or a month or longer. The co-administration period may be preceded by an administration period of just Compound 1 alone. For example, there could be administration of 100 mg of Compound 1 for 2 weeks followed by co-administration of 150 mg or 250 mg of Compound 2 for 1 additional week.

In one embodiment, 10 mg of Compound 1 may be administered once a day (QD) to a subject in need thereof followed by co-administration of 50 mg of Compound 2 every 12 hours. In one embodiment, 10 mg of Compound 1 may be administered once a day (QD) to a subject in need thereof followed by co-administration of 100 mg of Compound 2 every 12 hours. In one embodiment, 10 mg of Compound 1 may be administered once a day (QD) to a subject in need thereof followed by co-administration of 150 mg of Compound 2 every 12 hours. In another embodiment, 10 mg of Compound 1 may be administered once a day to a subject in need thereof followed by co-administration of 250 mg of Compound 2 every 12 hours.

In one embodiment, 30 mg of Compound 1 may be administered once a day (QD) to a subject in need thereof followed by co-administration of 50 mg of Compound 2 every 12 hours. In one embodiment, 30 mg of Compound 1 may be administered once a day (QD) to a subject in need thereof followed by co-administration of 100 mg of Compound 2 every 12 hours. In one embodiment, 30 mg of Compound 1 may be administered once a day (QD) to a subject in need thereof followed by co-administration of 150 mg of Compound 2 every 12 hours. In another embodiment, 30 mg of Compound 1 may be administered once a day to a subject in need thereof followed by co-administration of 250 mg of Compound 2 every 12 hours.

In one embodiment, 100 mg of Compound 1 may be administered once a day (QD) to a subject in need thereof followed by co-administration of 50 mg of Compound 2 every 12 hours. In one embodiment, 100 mg of Compound 1 may be administered once a day (QD) to a subject in need thereof followed by co-administration of 100 mg of Compound 2 every 12 hours. In one embodiment, 100 mg of Compound 1 may be administered once a day (QD) to a subject in need thereof followed by co-administration of 150 mg of Compound 2 every 12 hours. In another embodiment, 100 mg of Compound 1 may be administered once a day to a subject in need thereof followed by co-administration of 250 mg of Compound 2 every 12 hours.

In one embodiment, 150 mg of Compound 1 may be administered once a day (QD) to a subject in need thereof followed by co-administration of 50 mg of Compound 2 every 12 hours. In one embodiment, 150 mg of Compound 1 may be administered once a day (QD) to a subject in need thereof followed by co-administration of 100 mg of Compound 2 every 12 hours. In one embodiment, 150 mg of Compound 1 may be administered once a day (QD) to a subject in need thereof followed by co-administration of 150 mg of Compound 2 every 12 hours. In another embodiment, 150 mg of Compound 1 may be administered once a day to a subject in need thereof followed by co-administration of 250 mg of Compound 2 every 12 hours.

In the above embodiments, the dosage amounts may be achieved by administration of one or more tablets of the invention. Compound 2 may be administered as a pharmaceutical composition comprising Compound 2 and a pharmaceutically acceptable carrier. The duration of administration may continue until amelioration of the disease is achieved or until a subject's physician advises, e.g. duration of administration may be less than a week, 1 week, 2 weeks, 3 weeks, or a month or longer. The co-administration period may be preceded by an administration period of just Compound 1 alone. For example, there could be administration of 100 mg of Compound 1 for 2 weeks followed by co-administration of 150 mg or 250 mg of Compound 2 for 1 additional week.

In one embodiment, 50 mg of Compound 1 may be administered twice a day (BID) to a subject in need thereof followed by co-administration of 50 mg of Compound 2 twice a day (BID). In one embodiment, 50 mg of Compound 1 may be administered twice a day (BID) to a subject in need thereof followed by co-administration of 100 mg of Compound 2 twice a day (BID). In one embodiment, 50 mg of Compound 1 may be administered twice a day (BID) to a subject in need thereof followed by co-administration of 150 mg of Compound 2 twice a day (BID). In another embodiment, 50 mg of Compound 1 may be administered twice a day (BID) to a subject in need thereof followed by co-administration of 250 mg of Compound 2 twice a day (BID). In these embodiments, the dosage amounts may be achieved by administration of one or more tablets of the invention. Compound 2 may be administered as a pharmaceutical composition comprising Compound 2 and a pharmaceutically acceptable carrier. The duration of administration may continue until amelioration of the disease is achieved or until a subject's physician advises, e.g. duration of administration may be less than a week, 1 week, 2 weeks, 3 weeks, or a month or longer. The co-administration period may be preceded by an administration period of just Compound 1 alone. For example, there could be administration of 50 mg of Compound 1 for 2 weeks followed by co-administration of 50 mg or 100 mg of Compound 2 for 1 additional week.

When the CFTR mediated disease is cystic fibrosis, all of the above embodiments relating to dosage amounts and administrative schedules for Compound 1, or Compound and Compound 2, apply equally to patients who are homozygous or heterozygous.

These combinations are useful for treating the diseases described herein including cystic fibrosis. These combinations are also useful in the kits described herein.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

Therapeutic Uses for the Pharmaceutical Compositions

In one aspect, the invention also provides a method of treating, lessening the severity of, or symptomatically treating a disease in a patient, the method comprising administering an effective amount of the pharmaceutical composition or tablet of the invention to the patient, preferably a mammal, wherein the disease is selected from cystic fibrosis, asthma, smoke induced COPD, chronic bronchitis, rhinosinusitis, constipation, pancreatitis, pancreatic insufficiency, male infertility caused by congenital bilateral absence of the vas deferens (CBAVD), mild pulmonary disease, idiopathic pancreatitis, allergic bronchopulmonary aspergillosis (ABPA), liver disease, hereditary emphysema, hereditary hemochromatosis, coagulation-fibrinolysis deficiencies, such as protein C deficiency, Type 1 hereditary angioedema, lipid processing deficiencies, such as familial hypercholesterolemia, Type 1 chylomicronemia, abetalipoproteinemia, lysosomal storage diseases, such as I-cell disease/pseudo-Hurler, mucopolysaccharidoses, Sandhof/Tay-Sachs, Crigler-Najjar type II, polyendocrinopathy/hyperinsulemia, Diabetes mellitus, Laron dwarfism, myleoperoxidase deficiency, primary hypoparathyroidism, melanoma, glycanosis CDG type 1, congenital hyperthyroidism, osteogenesis imperfecta, hereditary hypofibrinogenemia, ACT deficiency, Diabetes insipidus (DI), neurophyseal DI, neprogenic DI, Charcot-Marie Tooth syndrome, Perlizaeus-Merzbacher disease, neurodegenerative diseases such as Alzheimer's disease, Parkinson's disease, amyotrophic lateral sclerosis, progressive supranuclear plasy, Pick's disease, several polyglutamine neurological disorders such as Huntington's, spinocerebullar ataxia type I, spinal and bulbar muscular atrophy, dentatorubal pallidoluysian, and myotonic dystrophy, as well as spongiform encephalopathies, such as hereditary Creutzfeldt-Jakob disease (due to prion protein processing defect), Fabry disease, Straussler-Scheinker syndrome, COPD, dry-eye disease, or Sjogren's disease, osteoporosis, osteopenia, bone healing and bone growth (including bone repair, bone regeneration, reducing bone resorption and increasing bone deposition), Gorham's Syndrome, chloride channelopathies such as myotonia congenita (Thomson and Becker forms), Bartter's syndrome type III, Dent's disease, hyperekplexia, epilepsy, lysosomal storage disease, Angelman syndrome, and Primary Ciliary Dyskinesia (PCD), a term for inherited disorders of the structure and/or function of cilia, including PCD with situs inversus (also known as Kartagener syndrome), PCD without situs inversus and ciliary aplasia.

In one aspect, the invention also provides a method of treating, lessening the severity of, or symptomatically treating a disease in a patient comprising administering an effective amount of the pharmaceutical composition or tablet of the invention to the patient, preferably a mammal, wherein the disease is selected from generalized epilepsy with febrile seizures plus (GEFS+), general epilepsy with febrile and afebrile seizures, myotonia, paramyotonia congenital, potassium-aggravated myotonia, hyperkalemic periodic paralysis, LQTS, LQTS/Brugada syndrome, autosomal-dominant LQTS with deafness, autosomal-recessive LQTS, LQTS with dysmorphic features, congenital and acquired LQTS, Timothy syndrome, persistent hyperinsulinemic hypolglycemia of infancy, dilated cardiomyopathy, autosomal-dominant LQTS, Dent disease, Osteopetrosis, Bartter syndrome type III, central core disease, malignant hyperthermia, and catecholaminergic polymorphic tachycardia.

In one aspect, the present invention is directed to a method of treating, lessening the severity of, or symptomatically treating cystic fibrosis in a patient comprising administering an effective amount of the pharmaceutical composition or tablet of the invention to the patient, preferably a mammal, wherein the patient possesses the CFTR genetic mutation N1303K, ΔI507, or R560T.

In one aspect, the present invention is directed to a method of treating, lessening the severity of, or symptomatically treating cystic fibrosis in a patient comprising administering an effective amount of the pharmaceutical composition or tablet of the invention to the patient, preferably a mammal, wherein the patient possesses the CFTR genetic mutation G551D. In another embodiment, the patient is homozygous in G551D. In another embodiment, the patient is heterozygous in G551D. In another embodiment, the patient is heterozygous in G551D, wherein the other CFTR genetic mutation is any one of ΔF508, G542X, N1303K, W1282X, R117H, R553X, 1717-1G→A, 621+1G→T, 2789+5G→A, 3849+10kbC→T, R1162X, G85E, 3120+1G→A, ΔI507, 1898+1G→A, 3659delC, R347P, R560T, R334W, A455E, 2184delA, or 711+1G→T.

In one aspect, the present invention is directed to a method of treating, lessening the severity of, or symptomatically treating cystic fibrosis in a patient comprising administering an effective amount of the pharmaceutical composition or tablet of the invention to the patient, preferably a mammal, wherein the patient possesses the CFTR genetic mutation ΔF508. In another embodiment, the patient is homozygous in ΔF508. In another embodiment, the patient is heterozygous in ΔF508. In another embodiment, the patient is heterozygous in ΔF508, wherein the other CFTR genetic mutation is any one of G551D, G542X, N1303K, W1282X, R117H, R553X, 1717-1G→A, 621+1G→T, 2789+5G→A, 3849+10kbC→T, R1162X, G85E, 3120+1G→A, ΔI507, 1898+1G→A, 3659delC, R347P, R560T, R334W, A455E, 2184delA, or 711+1G→T.

In certain embodiments, the pharmaceutically acceptable compositions comprising Compound 1 Amorphous Form and optionally an additional agent are useful for treating or lessening the severity of cystic fibrosis in patients who exhibit residual CFTR activity in the apical membrane of respiratory and non-respiratory epithelia. The presence of residual CFTR activity at the epithelial surface can be readily detected using methods known in the art, e.g., standard electrophysiological, biochemical, or histochemical techniques. Such methods identify CFTR activity using in vivo or ex vivo electrophysiological techniques, measurement of sweat or salivary Cl⁻ concentrations, or ex vivo biochemical or histochemical techniques to monitor cell surface density. Using such methods, residual CFTR activity can be readily detected in patients heterozygous or homozygous for a variety of different mutations, including patients homozygous or heterozygous for the most common mutation, ΔF508, as well as other mutations such as the G551D mutation, or the R117H mutation.

In one embodiment, Compound 1 Amorphous Form, as described herein, or pharmaceutically acceptable compositions thereof, are useful for treating or lessening the severity of cystic fibrosis in patients within certain genotypes exhibiting residual CFTR activity, e.g., class III mutations (impaired regulation or gating), class IV mutations (altered conductance), or class V mutations (reduced synthesis) (Lee R. Choo-Kang, Pamela L., Zeitlin, *Type I, II, III, IV, and V cystic fibrosis Tansmembrane Conductance Regulator Defects and Opportunities of Therapy*; Current Opinion in Pulmonary Medicine 6:521-529, 2000). Other patient genotypes that exhibit residual CFTR activity include patients homozygous for one of these classes or heterozygous with any other class of mutations, including class I mutations, class II mutations, or a mutation that lacks classification.

In one embodiment, Compound 1 Amorphous Form, as described herein, or pharmaceutically acceptable compositions thereof, are useful for treating or lessening the severity of cystic fibrosis in patients within certain clinical phenotypes, e.g., a moderate to mild clinical phenotype that typically correlates with the amount of residual CFTR activity in the apical membrane of epithelia. Such phenotypes include patients exhibiting pancreatic insufficiency or patients diagnosed with idiopathic pancreatitis and congenital bilateral absence of the vas deferens, or mild lung disease.

The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

In another aspect, the invention provides a method for treating cystic fibrosis in a patient, comprising administering a composition comprising:

a. 5 to 250 mg of (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide (Compound 1);

b. a filler;

c. a disintegrant;

d. a lubricant; and e. a glidant.

followed by co-administration of 100 to 300 mg N-(5-hydroxy-2,4-ditert-butyl-phenyl)-4-oxo-1H-quinoline-3-carboxamide (Compound 2) as a pharmaceutical composition comprising Compound 2 and a pharmaceutically acceptable carrier;

wherein the patient has a defective gene that causes a deletion of phenylalanine at position 508 of the cystic fibrosis transmembrane conductance regulator amino acid sequence, and wherein the patient is homozygous for the defective gene In one embodiment of this aspect, Compound 1 is in the form of Compound 1 Amorphous Form.

In this and other embodiments, Compound 1 or Compound 1 Amorphous Form is present in the tablet in an amount of about 10 mg.

In this and other embodiments, Compound 1 or Compound 1 Amorphous Form is present in the tablet in an amount of about 30 mg.

In this and other embodiments, Compound 1 or Compound 1 Amorphous Form is present in the tablet in an amount of about 100 mg.

In this and other embodiments, the tablet has the formulation set forth in the following table:

| Component | Function | Final Blend Composition % w/w | Tablet (mg/tablet) |
|---|---|---|---|
| 50% Compound 1/ 49.5% HPMCAS-HG/ 0.5% sodium lauryl sulfate | Active as a spray dried dispersion (SDD) | 50.00 | 10.0 SDD (5.00 Compound 1) |
| Microcrystalline cellulose | Filler | 22.62 | 4.52 |
| Lactose Monohydrate | Filler | 22.63 | 4.53 |
| Crosscarmelose Sodium | Disintegrant | 3.00 | 0.60 |
| Magnesium Stearate | Lubricant | 0.25 | 0.05 |
| Colloidal Silica Dioxide | Glidant | 1.00 | 0.20 |
| | Intragranular content | 99.5 | |
| Extragranular Blend | | | |
| Colloidal Silica Dioxide | Glidant | 0.25 | 0.05 |
| Magnesium Stearate | Lubricant | 0.25 | 0.05 |
| | Extragranular content | 0.5 | |
| | Total | 100.00 | 20.0 |

In this and other embodiments, the tablet has the formulation set forth in the following table:

| Component | Function | Final Blend Composition % w/w | Tablet (mg/tablet) |
|---|---|---|---|
| 50% Compound 1/ 49.5% HPMCAS-HG/ 0.5% sodium lauryl sulfate | Active as a spray dried dispersion (SDD) | 9.53 | 20.00 SDD (10.00 Compound 1) |
| Microcrystalline cellulose | Filler | 43.24 | 90.80 |
| Lactose Monohydrate | Filler | 43.24 | 90.80 |
| Crosscarmelose Sodium | Disintegrant | 3.00 | 6.30 |
| Magnesium Stearate | Lubricant | 0.50 | 1.05 |
| Colloidal Silica Dioxide | Glidant | 0.50 | 1.05 |
| | Total | 100.00 | 210.0 |

In this and other embodiments, the tablet has the formulation set forth in the following table:

| Component | Function | Final Blend Composition % w/w | Tablet (mg/tablet) |
|---|---|---|---|
| 50% Compound 1/ 49.5% HPMCAS-HG/ 0.5% sodium lauryl sulfate | Active as a spray dried dispersion (SDD) | 50.00 | 100.0 SDD (50.00 Compound 1) |
| Microcrystalline cellulose | Filler | 22.62 | 45.20 |
| Lactose Monohydrate | Filler | 22.63 | 45.30 |
| Crosscarmelose Sodium | Disintegrant | 3.00 | 6.0 |
| Magnesium Stearate | Lubricant | 0.25 | 0.5 |
| Colloidal Silica Dioxide | Glidant | 1.00 | 2.0 |
| | Intragranular content | 99.5 | |
| Extragranular Blend | | | |
| Colloidal Silica Dioxide | Glidant | 0.25 | 0.5 |
| Magnesium Stearate | Lubricant | 0.25 | 0.5 |
| | Extragranular content | 0.5 | |
| | Total | 100.00 | 200.0 |

In this and other embodiments, the tablet has the formulation set forth in the following table:

| Component | Function | Final Blend Composition % w/w | Tablet (mg/tablet) |
|---|---|---|---|
| 50% Compound 1/ 49.5% HPMCAS-HG/ 0.5% sodium lauryl sulfate | Active as a spray dried dispersion (SDD) | 50.00 | 200.0 SDD (100.00 Compound 1) |
| Microcrystalline cellulose | Filler | 22.63 | 90.5 |
| Lactose Monohydrate | Filler | 22.63 | 90.5 |
| Crosscarmelose Sodium | Disintegrant | 3.00 | 12.0 |
| Magnesium Stearate | Lubricant | 0.25 | 1.0 |
| Colloidal Silica Dioxide | Glidant | 1.00 | 4.0 |
| | Intragranular content | 99.5 | |
| Extragranular Blend | | | |
| Colloidal Silica Dioxide | Glidant | 0.25 | 1.0 |
| Magnesium Stearate | Lubricant | 0.25 | 1.0 |
| | Extragranular content | 0.5 | |
| | Total | 100.00 | 400.0 |

In this and other embodiments, the tablet has the formulation set forth in the following table:

| Component | Function | Final Blend Composition % w/w | Tablet (mg/tablet) |
|---|---|---|---|
| 50% Compound 1/ 49.5% HPMCAS-HG/ 0.5% SLS | Active as a spray dried dispersion (SDD) | 50.00 | 500.0 SDD (250.00 Compound 1) |
| Microcrystalline cellulose (Avicel PH101) | Filler | 22.63 | 226.3 |
| Lactose Monohydrate (Foremost 310) | Filler | 22.63 | 226.3 |
| Crosscarmelose Sodium (AcDiSol) | Disintegrant | 3.00 | 30.0 |
| Magnesium Stearate | Lubricant | 0.25 | 2.5 |
| Colloidal Silica Dioxide (Cabot M5P) | Glidant | 1.00 | 10.0 |
| | Intragranular content | 99.5 | |

| Component | Function | Final Blend Composition % w/w | Tablet (mg/tablet) |
|---|---|---|---|
| Extragranular Blend | | | |
| Colloidal Silica Dioxide (Cabot M5P) | Glidant | 0.25 | 2.5 |
| Magnesium Stearate | Lubricant | 0.25 | 2.5 |
| | Extragranular content | 0.5 | |
| | Total | 100.00 | 1000.0 |

In this and other embodiments, Compound 1 is administered once a day.

In this and other embodiments, 150 mg of Compound 2 is administered.

In this and other embodiments, 250 mg of Compound 2 is administered.

In this and other embodiments, Compound 2 is administered every 12 hours.

In this and other embodiments, the method comprises administering an additional therapeutic agent.

In this and other embodiments, the additional therapeutic agent is a mucolytic agent, bronchodialator, an antibiotic, an anti-infective agent, an anti-inflammatory agent, a CFTR modulator other than Compound 2, or a nutritional agent.

In another aspect, the invention provides a method for treating cystic fibrosis in a patient, comprising administering a composition comprising:
  a. 5 to 250 mg of (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide (Compound 1);
  b. a filler;
  c. a disintegrant;
  d. a lubricant; and
  e. a glidant.
followed by co-administration of 100 to 300 mg N-(5-hydroxy-2,4-ditert-butyl-phenyl)-4-oxo-1H-quinoline-3-carboxamide (Compound 2) as a pharmaceutical composition comprising Compound 2 and a pharmaceutically acceptable carrier;
wherein the patient has a defective gene that causes a deletion of phenylalanine at position 508 of the cystic fibrosis transmembrane conductance regulator amino acid sequence.

In this and other embodiments, Compound 2 can be administered concurrently with, prior to, or subsequent to, Compound 1.

In one embodiment of this aspect, Compound 1 is in the form of Compound 1 Amorphous Form.

In another embodiment, Compound 1 or Compound 1 Amorphous Form is present in the tablet in an amount of about 10 mg.

In another embodiment, Compound 1 or Compound 1 Amorphous Form is present in the tablet in an amount of about 30 mg.

In another embodiment, Compound 1 or Compound 1 Amorphous Form is present in the tablet in an amount of about 100 mg.

In another embodiment, the tablet has the formulation set forth in the following table:

| Component | Function | Final Blend Composition % w/w | Tablet (mg/tablet) |
|---|---|---|---|
| 50% Compound 1/ 49.5% HPMCAS-HG/ 0.5% sodium lauryl sulfate | Active as a spray dried dispersion (SSD) | 50.00 | 10.0 SDD (5.00 Compound 1) |
| Microcrystalline cellulose | Filler | 22.62 | 4.52 |
| Lactose Monohydrate | Filler | 22.63 | 4.53 |
| Crosscarmelose Sodium | Disintegrant | 3.00 | 0.60 |
| Magnesium Stearate | Lubricant | 0.25 | 0.05 |
| Colloidal Silica Dioxide | Glidant | 1.00 | 0.20 |
| | Intragranular content | 99.5 | |
| Extragranular Blend | | | |
| Colloidal Silica Dioxide | Glidant | 0.25 | 0.05 |
| Magnesium Stearate | Lubricant | 0.25 | 0.05 |
| | Extragranular content | 0.5 | |
| | Total | 100.00 | 20.0 |

In another embodiment, the tablet has the formulation set forth in the following table:

| Component | Function | Final Blend Composition % w/w | Tablet (mg/tablet) |
|---|---|---|---|
| 50% Compound 1/ 49.5% HPMCAS-HG/ 0.5% sodium lauryl sulfate | Active as a spray dried dispersion (SSD) | 9.53 | 20.00 SDD (10.00 Compound 1) |
| Microcrystalline cellulose | Filler | 43.24 | 90.80 |
| Lactose Monohydrate | Filler | 43.24 | 90.80 |
| Crosscarmelose Sodium | Disintegrant | 3.00 | 6.30 |
| Magnesium Stearate | Lubricant | 0.50 | 1.05 |
| Colloidal Silica Dioxide | Glidant | 0.50 | 1.05 |
| | Total | 100.00 | 210.0 |

In another embodiment, the tablet has the formulation set forth in the following table:

| Component | Function | Final Blend Composition % w/w | Tablet (mg/tablet) |
|---|---|---|---|
| 50% Compound 1/ 49.5% HPMCAS-HG/ 0.5% sodium lauryl sulfate | Active as a spray dried dispersion (SSD) | 50.00 | 100.0 SDD (50.00 Compound 1) |
| Microcrystalline cellulose | Filler | 22.62 | 45.20 |
| Lactose Monohydrate | Filler | 22.63 | 45.30 |
| Crosscarmelose Sodium | Disintegrant | 3.00 | 6.0 |
| Magnesium Stearate | Lubricant | 0.25 | 0.5 |
| Colloidal Silica Dioxide | Glidant | 1.00 | 2.0 |
| | Intragranular content | 99.5 | |

-continued

| Component | Function | Final Blend Composition % w/w | Tablet (mg/tablet) |
|---|---|---|---|
| Extragranular Blend | | | |
| Colloidal Silica Dioxide | Glidant | 0.25 | 0.5 |
| Magnesium Stearate | Lubricant | 0.25 | 0.5 |
| | Extragranular content | 0.5 | |
| | Total | 100.00 | 200.0 |

In another embodiment, the tablet has the formulation set forth in the following table:

| Component | Function | Final Blend Composition % w/w | Tablet (mg/tablet) |
|---|---|---|---|
| 50% Compound 1/ 49.5% HPMCAS-HG/ 0.5% sodium lauryl sulfate | Active as a spray dried dispersion (SSD) | 50.00 | 200.0 SDD (100.00 Compound 1) |
| Microcrystalline cellulose | Filler | 22.63 | 90.5 |
| Lactose Monohydrate | Filler | 22.63 | 90.5 |
| Crosscarmelose Sodium | Disintegrant | 3.00 | 12.0 |
| Magnesium Stearate | Lubricant | 0.25 | 1.0 |
| Colloidal Silica Dioxide | Glidant | 1.00 | 4.0 |
| | Intragranular content | 99.5 | |
| Extragranular Blend | | | |
| Colloidal Silica Dioxide | Glidant | 0.25 | 1.0 |
| Magnesium Stearate | Lubricant | 0.25 | 1.0 |
| | Extragranular content | 0.5 | |
| | Total | 100.00 | 400.0 |

In another embodiment, the tablet has the formulation set forth in the following table:

| Component | Function | Final Blend Composition % w/w | Tablet (mg/tablet) |
|---|---|---|---|
| 50% Compound 1/ 49.5% HPMCAS-HG/ 0.5% SLS | Active as a spray dried dispersion (SSD) | 50.00 | 500.0 SDD (250.00 Compound 1) |
| Microcrystalline cellulose (Avicel PH101) | Filler | 22.63 | 226.3 |
| Lactose Monohydrate (Foremost 310) | Filler | 22.63 | 226.3 |
| Crosscarmelose Sodium (AcDiSol) | Disintegrant | 3.00 | 30.0 |
| Magnesium Stearate | Lubricant | 0.25 | 2.5 |
| Colloidal Silica Dioxide (Cabot M5P) | Glidant | 1.00 | 10.0 |
| | Intragranular content | 99.5 | |
| Extragranular Blend | | | |
| Colloidal Silica Dioxide (Cabot M5P) | Glidant | 0.25 | 2.5 |
| Magnesium Stearate | Lubricant | 0.25 | 2.5 |
| | Extragranular content | 0.5 | |
| | Total | 100.00 | 1000.0 |

In another embodiment, Compound 1 is administered once a day.

In another embodiment, 150 mg of Compound 2 is administered.

In another embodiment, 250 mg of Compound 2 is administered.

In another embodiment, Compound 2 is administered every 12 hours.

In these and other embodiments, the patient is homozygous for the defective gene.

In another embodiment, the method comprises administering an additional therapeutic agent.

In another embodiment, the additional therapeutic agent is a mucolytic agent, bronchodialator, an antibiotic, an anti-infective agent, an anti-inflammatory agent, a CFTR modulator other than Compound 2, or a nutritional agent.

EXAMPLES

Methods & Materials

Modulated Differential Scanning Calorimetry (MDSC) and Differential Scanning Calorimetry (DSC)

The modulated differential scanning calorimetry (MDSC) was used for testing the glass transition temperature of the amorphous form and spray dried dispersion of a compound. Differential scanning calorimetry (DSC) was used to determine the melting point of crystalline materials and to discriminate between different polymorphs. The data were collected using a TA DSC Q2000 differential scanning calorimeter (TA Instruments, New Castle, Del.). The instrument was calibrated with indium. Samples of approximately 1-5 mg were weighed into aluminum hermetic pans that were crimped using lids with one hole. For MDSC the samples were scanned from −20° C. to 220° C. at 2° C./minute heating rate with +/−1° C. modulation every 60 seconds. For DSC the samples were scanned from 25° C. to 220° C. at a heating rate of 10° C./min. Data were collected by Thermal Advantage Q Series™ software (version: 2.7.0.380) and analyzed by Universal Analysis software (version: 4.4A, build: 4.4.0.5) (TA Instruments, New Castle, Del.).

XRPD (X-Ray Powder Diffraction)

X-ray Powder Diffraction was used to characterize the physical form of the lots produced to date and to characterize different polymorphs identified. The XRPD data of a compound were collected on a PANalytical X'pert Pro Powder X-ray Diffractometer (Almelo, the Netherlands). The XRPD pattern was recorded at room temperature with copper radiation (1.54060 A). The X-ray was generated using Cu sealed tube at 45 kV, 40 mA with a Nickel Kβ suppression filter. The incident beam optic was comprised of a variable divergence slit to ensure a constant illuminated length on the sample and on the diffracted beam side; a fast linear solid state detector was used with an active length of 2.12 degrees 2 theta measured in a scanning mode. The powder sample was packed on the indented area of a zero background silicon holder and spinning was performed to achieve better statistics. A symmetrical scan was measured from 4-40 degrees 2 theta with a step size of 0.017 degrees and a scan step time of 15.5 seconds. The data collection software is X'pert Data Collector (version 2.2e). The data analysis software is either X'pert Data Viewer (version 1.2d) or X'pert Highscore (version: 2.2c).

Thermogravimetric Analysis (TGA)

TGA was used to investigate the presence of residual solvents in the lots characterized, and identify the temperature at which decomposition of the sample occurs. TGA data were collected on a TA Q500 Thermogravimetric Analyzer (TA Instruments, New Castle, Del.). A sample with weight of approximately 2-5 mg was scanned from 25° C. to 300° C. at a heating rate of 10° C./min. Data were collected by Thermal Advantage Q Series™ software (version 2.5.0.255) and analyzed by Universal Analysis software (version 4.4A, build 4.4.0.5) (TA Instruments, New Castle, Del.).

Compound 1 Form A Single Crystal Structure Determination

Diffraction data were acquired on Bruker Apex II diffractometer equipped with sealed tube Cu Kα source and an Apex II CCD detector. The structure was solved and refined using SHELX program (Sheldrick, G. M., Acta Cryst., (2008) A64, 112-122). Based on intensities statistics and systematic absences the structure was solved and refined in C2 space group. The absolute configuration was determined using anomalous diffraction. Flack parameter refined to 0.00 (18) indicating that the model represent the correct enantiomer [(R)].

Solid State NMR

Solid state NMR was conducted on a Bruker-Biospin 400 MHz wide-bore spectrometer equipped with a Bruker-Biospin 4 mm HFX probe. Samples were packed into 4 mm $ZrO_2$ rotors and spun under Magic Angle Spinning (MAS) condition with spinning speed of 12.5 kHz. The proton relaxation time was first measured using $^1H$ MAS $T_1$ saturation recovery relaxation experiment in order to set up proper recycle delay of the $^{13}C$ cross-polarization (CP) MAS experiment. The CP contact time of carbon CPMAS experiment was set to 2 ms. A CP proton pulse with linear ramp (from 50% to 100%) was employed. The Hartmann-Hahn match was optimized on external reference sample (glycine). The fluorine MAS spectrum was recorded with proton decoupling. TPPM15 decoupling sequence was used with the field strength of approximately 100 kHz for both $^{13}C$ and $^{19}F$ acquisitions.

Reagents and Compounds

Vitride® (sodium bis(2-methoxyethoxy)aluminum hydride [or $NaAlH_2(OCH_2CH_2OCH_3)_2$], 65 wgt % solution in toluene) was purchased from Aldrich Chemicals. 3-Fluoro-4-nitroaniline was purchased from Capot Chemicals. 5-Bromo-2,2-difluoro-1,3-benzodioxole was purchased from Alfa Aesar. 2,2-Difluoro-1,3-benzodioxole-5-carboxylic acid was purchased from Saltigo (an affiliate of the Lanxess Corporation).

Anywhere in the present application where a name of a compound may not correctly describe the structure of the compound, the structure supersedes the name and governs.

Synthesis of Compound 1

Acid Chloride Moiety

Synthesis of (2,2-difluoro-1,3-benzodioxol-5-yl)-1-ethylacetate-acetonitrile

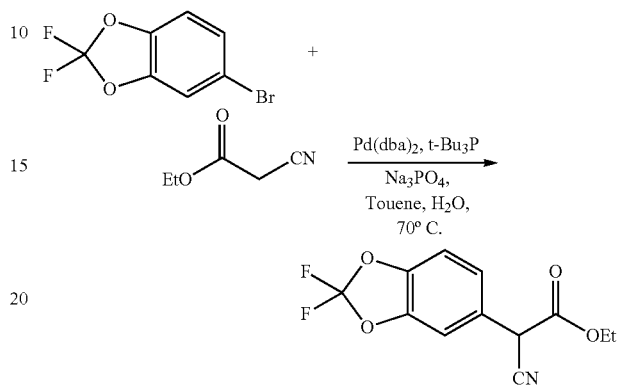

A reactor was purged with nitrogen and charged with 900 mL of toluene. The solvent was degassed via nitrogen sparge for no less than 16 h. To the reactor was then charged $Na_3PO_4$ (155.7 g, 949.5 mmol), followed by bis(dibenzylideneacetone) palladium (0) (7.28 g, 12.66 mmol). A 10% w/w solution of tert-butylphosphine in hexanes (51.23 g, 25.32 mmol) was charged over 10 min at 23° C. from a nitrogen purged addition funnel. The mixture was allowed to stir for 50 min, at which time 5-bromo-2,2-difluoro-1,3-benzodioxole (75 g, 316.5 mmol) was added over 1 min. After stirring for an additional 50 min, the mixture was charged with ethyl cyanoacetate (71.6 g, 633.0 mmol) over 5 min followed by water (4.5 mL) in one portion. The mixture was heated to 70° C. over 40 min and analyzed by HPLC every 1-2 h for the percent conversion of the reactant to the product. After complete conversion was observed (typically 100% conversion after 5-8 h), the mixture was cooled to 20-25° C. and filtered through a celite pad. The celite pad was rinsed with toluene (2×450 mL) and the combined organics were concentrated to 300 mL under vacuum at 60-65° C. The concentrate was charged with 225 mL DMSO and concentrated under vacuum at 70-80° C. until active distillation of the solvent ceased. The solution was cooled to 20-25° C. and diluted to 900 mL with DMSO in preparation for Step 2. $^1H$ NMR (500 MHz, $CDCl_3$) δ 7.16-7.10 (m, 2H), 7.03 (d, J=8.2 Hz, 1H), 4.63 (s, 1H), 4.19 (m, 2H), 1.23 (t, J=7.1 Hz, 3H).

Synthesis of (2,2-difluoro-1,3-benzodioxol-5-yl)-acetonitrile

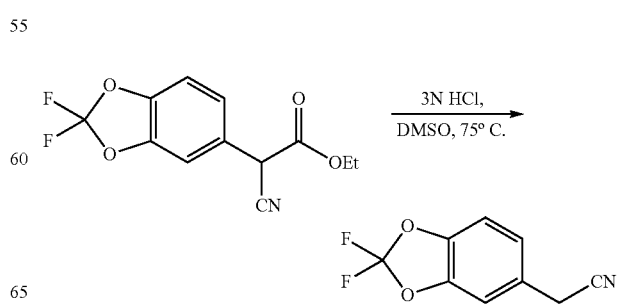

The DMSO solution of (2,2-difluoro-1,3-benzodioxol-5-yl)-1-ethylacetate-acetonitrile from above was charged with 3 N HCl (617.3 mL, 1.85 mol) over 20 min while maintaining an internal temperature <40° C. The mixture was then heated to 75° C. over 1 h and analyzed by HPLC every 1-2 h for % conversion. When a conversion of >99% was observed (typically after 5-6 h), the reaction was cooled to 20-25° C. and extracted with MTBE (2×525 mL), with sufficient time to allow for complete phase separation during the extractions. The combined organic extracts were washed with 5% NaCl (2×375 mL). The solution was then transferred to equipment appropriate for a 1.5-2.5 Torr vacuum distillation that was equipped with a cooled receiver flask. The solution was concentrated under vacuum at <60° C. to remove the solvents. (2,2-Difluoro-1,3-benzodioxol-5-yl)-acetonitrile was then distilled from the resulting oil at 125-130° C. (oven temperature) and 1.5-2.0 Torr. (2,2-Difluoro-1,3-benzodioxol-5-yl)-acetonitrile was isolated as a clear oil in 66% yield from 5-bromo-2,2-difluoro-1,3-benzodioxole (2 steps) and with an HPLC purity of 91.5% AUC (corresponds to a w/w assay of 95%). $^1$H NMR (500 MHz, DMSO) δ 7.44 (br s, 1H), 7.43 (d, J=8.4 Hz, 1H), 7.22 (dd, J=8.2, 1.8 Hz, 1H), 4.07 (s, 2H).

Synthesis of (2,2-difluoro-1,3-benzodioxol-5-yl)-cyclopropanecarbonitrile

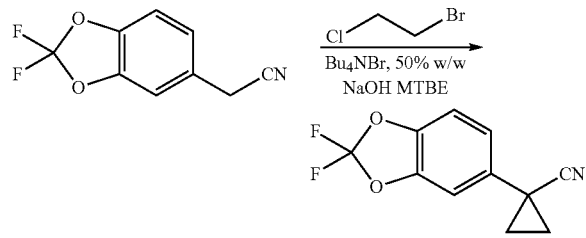

A stock solution of 50% w/w NaOH was degassed via nitrogen sparge for no less than 16 h. An appropriate amount of MTBE was similarly degassed for several hours. To a reactor purged with nitrogen was charged degassed MTBE (143 mL) followed by (2,2-difluoro-1,3-benzodioxol-5-yl)-acetonitrile (40.95 g, 207.7 mmol) and tetrabutylammonium bromide (2.25 g, 10.38 mmol). The volume of the mixture was noted and the mixture was degassed via nitrogen sparge for 30 min. Enough degassed MTBE is charged to return the mixture to the original volume prior to degassing. To the stirring mixture at 23.0° C. was charged degassed 50% w/w NaOH (143 mL) over 10 min followed by 1-bromo-2-chloroethane (44.7 g, 311.6 mmol) over 30 min. The reaction was analyzed by HPLC in 1 h intervals for % conversion. Before sampling, stirring was stopped and the phases allowed to separate. The top organic phase was sampled for analysis. When a % conversion >99% was observed (typically after 2.5-3 h), the reaction mixture was cooled to 10° C. and was charged with water (461 mL) at such a rate as to maintain a temperature <25° C. The temperature was adjusted to 20-25° C. and the phases separated. Note: sufficient time should be allowed for complete phase separation. The aqueous phase was extracted with MTBE (123 mL), and the combined organic phase was washed with 1 N HCl (163 mL) and 5% NaCl (163 mL). The solution of (2,2-difluoro-1,3-benzodioxol-5-yl)-cyclopropanecarbonitrile in MTBE was concentrated to 164 mL under vacuum at 40-50° C. The solution was charged with ethanol (256 mL) and again concentrated to 164 mL under vacuum at 50-60° C. Ethanol (256 mL) was charged and the mixture concentrated to 164 mL under vacuum at 50-60° C. The resulting mixture was cooled to 20-25° C. and diluted with ethanol to 266 mL in preparation for the next step. $^1$H NMR (500 MHz, DMSO) δ 7.43 (d, J=8.4 Hz, 1H), 7.40 (d, J=1.9 Hz, 1H), 7.30 (dd, J=8.4, 1.9 Hz, 1H), 1.75 (m, 2H), 1.53 (m, 2H).

Synthesis of 1-(2,2-difluoro-1,3-benzodioxol-5-yl)-cyclopropanecarboxylic Acid

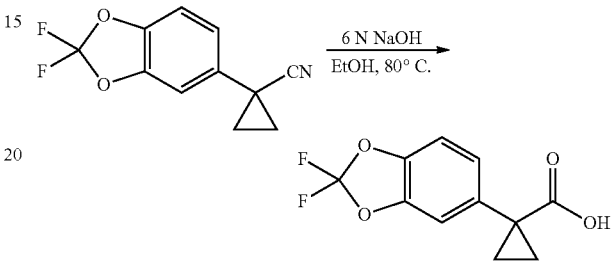

The solution of (2,2-difluoro-1,3-benzodioxol-5-yl)-cyclopropanecarbonitrile in ethanol from the previous step was charged with 6 N NaOH (277 mL) over 20 min and heated to an internal temperature of 77-78° C. over 45 min. The reaction progress was monitored by HPLC after 16 h. Note: the consumption of both (2,2-difluoro-1,3-benzodioxol-5-yl)-cyclopropanecarbonitrile and the primary amide resulting from partial hydrolysis of (2,2-difluoro-1,3-benzodioxol-5-yl)-cyclopropanecarbonitrile were monitored. When a % conversion >99% was observed (typically 100% conversion after 16 h), the reaction mixture was cooled to 25° C. and charged with ethanol (41 mL) and DCM (164 mL). The solution was cooled to 10° C. and charged with 6 N HCl (290 mL) at such a rate as to maintain a temperature <25° C. After warming to 20-25° C., the phases were allowed to separate. The bottom organic phase was collected and the top aqueous phase was back extracted with DCM (164 mL). Note: the aqueous phase was somewhat cloudy before and after the extraction due to a high concentration of inorganic salts. The organics were combined and concentrated under vacuum to 164 mL. Toluene (328 mL) was charged and the mixture condensed to 164 mL at 70-75° C. The mixture was cooled to 45° C., charged with MTBE (364 mL) and stirred at 60° C. for 20 min. The solution was cooled to 25° C. and polish filtered to remove residual inorganic salts. MTBE (123 mL) was used to rinse the reactor and the collected solids. The combined organics were transferred to a clean reactor in preparation for the next step.

Isolation of 1-(2,2-difluoro-1,3-benzodioxol-5-yl)-cyclopropanecarboxylic Acid

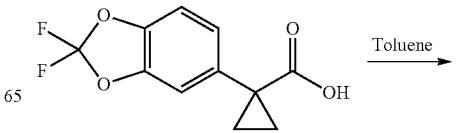

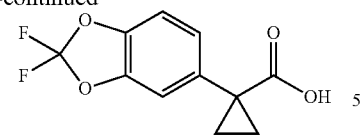

The solution of 1-(2,2-difluoro-1,3-benzodioxol-5-yl)-cyclopropanecarboxylic acid from the previous step is concentrated under vacuum to 164 mL, charged with toluene (328 mL) and concentrated to 164 mL at 70-75° C. The mixture was then heated to 100-105° C. to give a homogeneous solution. After stirring at that temperature for 30 min, the solution was cooled to 5° C. over 2 hours and maintained at 5° C. for 3 hours. The mixture was then filtered and the reactor and collected solid washed with cold 1:1 toluene/n-heptane (2×123 mL). The material was dried under vacuum at 55° C. for 17 hours to provide 1-(2,2-difluoro-1,3-benzodioxol-5-yl)-cyclopropanecarboxylic acid as an off-white crystalline solid. 1-(2,2-difluoro-1,3-benzodioxol-5-yl)-cyclopropanecarboxylic acid was isolated in 79% yield from (2,2-difluoro-1,3-benzodioxol-5-yl)-acetonitrile (3 steps including isolation) and with an HPLC purity of 99.0% AUC. ESI-MS m/z calc. 242.04, found 241.58 (M+1)+; 1H NMR (500 MHz, DMSO) δ 12.40 (s, 1H), 7.40 (d, J=1.6 Hz, 1H), 7.30 (d, J=8.3 Hz, 1H), 7.17 (dd, J=8.3, 1.7 Hz, 1H), 1.46 (m, 2H), 1.17 (m, 2H).

Alternative Synthesis of the Acid Chloride Moiety

Synthesis of
(2,2-difluoro-1,3-benzodioxol-5-yl)-methanol

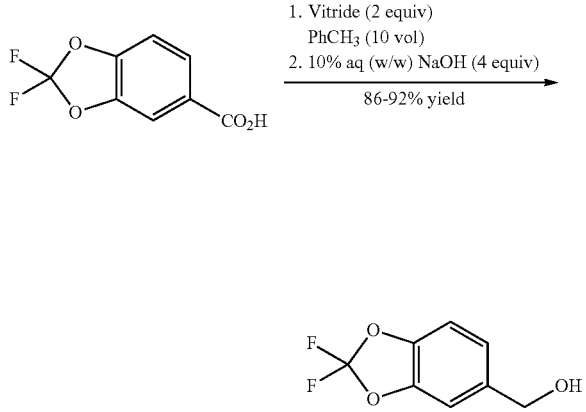

Commercially available 2,2-difluoro-1,3-benzodioxole-5-carboxylic acid (1.0 eq) is slurried in toluene (10 vol). Vitride® (2 eq) is added via addition funnel at a rate to maintain the temperature at 15-25° C. At the end of addition the temperature is increased to 40° C. for 2 h then 10% (w/w) aq. NaOH (4.0 eq) is carefully added via addition funnel maintaining the temperature at 40-50° C. After stirring for an additional 30 minutes, the layers are allowed to separate at 40° C. The organic phase is cooled to 20° C. then washed with water (2×1.5 vol), dried (Na2SO4), filtered, and concentrated to afford crude (2,2-difluoro-1,3-benzodioxol-5-yl)-methanol that is used directly in the next step.

Synthesis of
5-chloromethyl-2,2-difluoro-1,3-benzodioxole

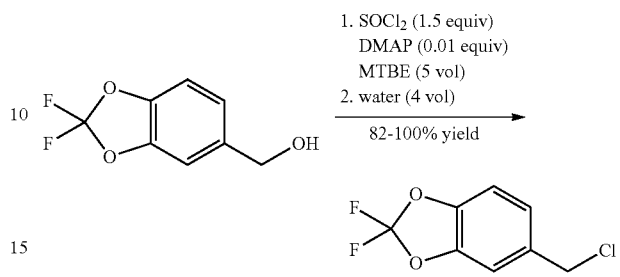

(2,2-difluoro-1,3-benzodioxol-5-yl)-methanol (1.0 eq) is dissolved in MTBE (5 vol). A catalytic amount of DMAP (1 mol %) is added and SOCl2 (1.2 eq) is added via addition funnel. The SOCl2 is added at a rate to maintain the temperature in the reactor at 15-25° C. The temperature is increased to 30° C. for 1 hour then cooled to 20° C. then water (4 vol) is added via addition funnel maintaining the temperature at less than 30° C. After stirring for an additional 30 minutes, the layers are allowed to separate. The organic layer is stirred and 10% (w/v) aq. NaOH (4.4 vol) is added. After stirring for 15 to 20 minutes, the layers are allowed to separate. The organic phase is then dried (Na2SO4), filtered, and concentrated to afford crude 5-chloromethyl-2,2-difluoro-1,3-benzodioxole that is used directly in the next step.

Synthesis of
(2,2-difluoro-1,3-benzodioxol-5-yl)-acetonitrile

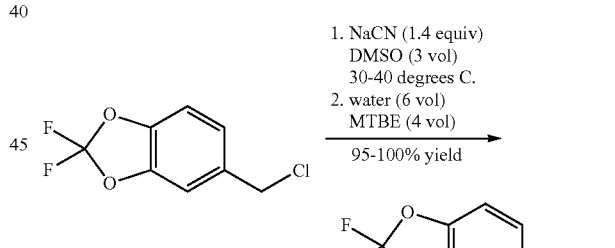

A solution of 5-chloromethyl-2,2-difluoro-1,3-benzodioxole (1 eq) in DMSO (1.25 vol) is added to a slurry of NaCN (1.4 eq) in DMSO (3 vol) maintaining the temperature between 30-40° C. The mixture is stirred for 1 hour then water (6 vol) is added followed by MTBE (4 vol). After stirring for 30 min, the layers are separated. The aqueous layer is extracted with MTBE (1.8 vol). The combined organic layers are washed with water (1.8 vol), dried (Na2SO4), filtered, and concentrated to afford crude (2,2-difluoro-1,3-benzodioxol-5-yl)-acetonitrile (95%) that is used directly in the next step.

The remaining steps are the same as described above for the synthesis of the acid moiety.

Amine Moiety

Synthesis of 2-bromo-5-fluoro-4-ntroaniline

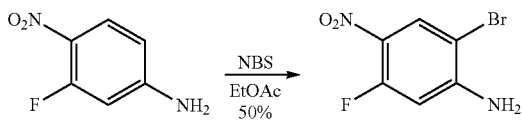

A flask was charged with 3-fluoro-4-nitroaniline (1.0 equiv) followed by ethyl acetate (10 vol) and stirred to dissolve all solids. N-Bromosuccinimide (1.0 equiv) was added as a portion-wise as to maintain internal temperature of 22° C. At the end of the reaction, the reaction mixture was concentrated in vacuo on a rotavap. The residue was slurried in distilled water (5 vol) to dissolve and remove succinimide. (The succinimide can also be removed by water workup procedure.) The water was decanted and the solid was slurried in 2-propanol (5 vol) overnight. The resulting slurry was filtered and the wetcake was washed with 2-propanol, dried in vacuum oven at 50° C. overnight with $N_2$ bleed until constant weight was achieved. A yellowish tan solid was isolated (50% yield, 97.5% AUC). Other impurities were a bromo-regioisomer (1.4% AUC) and a di-bromo adduct (1.1% AUC). $^1$H NMR (500 MHz, DMSO) δ 8.19 (1H, d, J=8.1 Hz), 7.06 (br. s, 2H), 6.64 (d, 1H, J=14.3 Hz).

Synthesis of benzylglycolated-4-ammonium-2-bromo-5-fluoroaniline Tosylate Salt

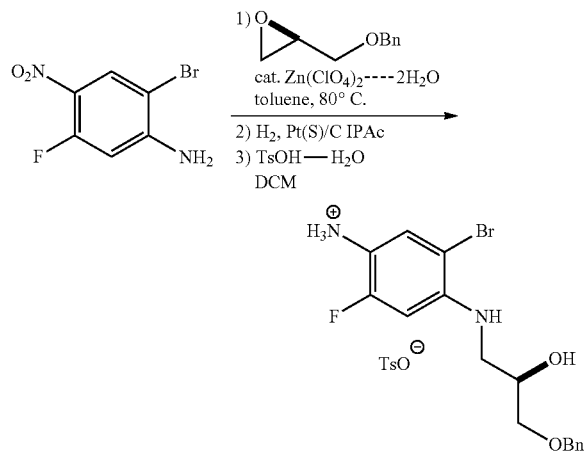

A thoroughly dried flask under $N_2$ was charged with the following: Activated powdered 4A molecular sieves (50 wt % based on 2-bromo-5-fluoro-4-nitroaniline), 2-Bromo-5-fluoro-4-nitroaniline (1.0 equiv), zinc perchlorate dihydrate (20 mol %), and toluene (8 vol). The mixture was stirred at room temperature for NMT 30 min. Lastly, (R)-benzyl glycidyl ether (2.0 equiv) in toluene (2 vol) was added in a steady stream. The reaction was heated to 80° C. (internal temperature) and stirred for approximately 7 hours or until 2-Bromo-5-fluoro-4-nitroaniline was <5% AUC.

The reaction was cooled to room temperature and Celite (50 wt %) was added, followed by ethyl acetate (10 vol). The resulting mixture was filtered to remove Celite and sieves and washed with ethyl acetate (2 vol). The filtrate was washed with ammonium chloride solution (4 vol, 20% w/v). The organic layer was washed with sodium bicarbonate solution (4 vol×2.5% w/v). The organic layer was concentrated in vacuo on a rotavap. The resulting slurry was dissolved in isopropyl acetate (10 vol) and this solution was transferred to a Buchi hydrogenator.

The hydrogenator was charged with 5 wt % Pt(S)/C (1.5 mol %) and the mixture was stirred under $N_2$ at 30° C. (internal temperature). The reaction was flushed with $N_2$ followed by hydrogen. The hydrogenator pressure was adjusted to 1 Bar of hydrogen and the mixture was stirred rapidly (>1200 rpm). At the end of the reaction, the catalyst was filtered through a pad of Celite and washed with dichloromethane (10 vol). The filtrate was concentrated in vacuo. Any remaining isopropyl acetate was chased with dichloromethane (2 vol) and concentrated on a rotavap to dryness.

The resulting residue was dissolved in dichloromethane (10 vol). p-Toluenesulfonic acid monohydrate (1.2 equiv) was added and stirred overnight. The product was filtered and washed with dichloromethane (2 vol) and suction dried. The wetcake was transferred to drying trays and into a vacuum oven and dried at 45° C. with $N_2$ bleed until constant weight was achieved. Benzylglycolated-4-ammonium-2-bromo-5-fluoroaniline tosylate salt was isolated as an off-white solid.

Chiral purity was determined to be >97% ee.

Synthesis of (3-Chloro-3-methylbut-1-ynyl)trimethylsilane

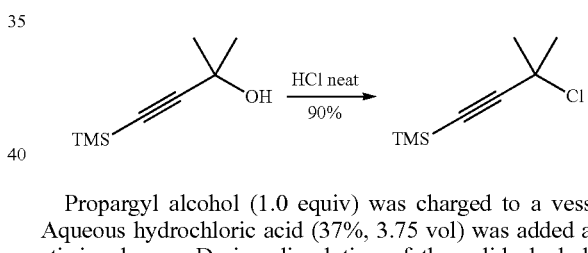

Propargyl alcohol (1.0 equiv) was charged to a vessel. Aqueous hydrochloric acid (37%, 3.75 vol) was added and stirring begun. During dissolution of the solid alcohol, a modest endotherm (5-6° C.) is observed. The resulting mixture was stirred overnight (16 h), slowly becoming dark red. A 30 L jacketed vessel is charged with water (5 vol) which is then cooled to 10° C. The reaction mixture is transferred slowly into the water by vacuum, maintaining the internal temperature of the mixture below 25° C. Hexanes (3 vol) is added and the resulting mixture is stirred for 0.5 h. The phases were settled and the aqueous phase (pH<1) was drained off and discarded. The organic phase was concentrated in vacuo using a rotary evaporator, furnishing the product as red oil.

Synthesis of (4-(Benzyloxy)-3,3-dimethylbut-1-ynyl)trimethylsilane

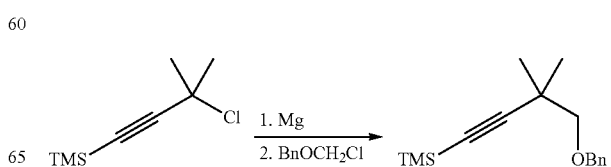

Method A

All equivalent and volume descriptors in this part are based on a 250 g reaction. Magnesium turnings (69.5 g, 2.86 mol, 2.0 equiv) were charged to a 3 L 4-neck reactor and stirred with a magnetic stirrer under nitrogen for 0.5 h. The reactor was immersed in an ice-water bath. A solution of the propargyl chloride (250 g, 1.43 mol, 1.0 equiv) in THF (1.8 L, 7.2 vol) was added slowly to the reactor, with stirring, until an initial exotherm (~10° C.) was observed. The Grignard reagent formation was confirmed by IPC using $^1$H-NMR spectroscopy. Once the exotherm subsided, the remainder of the solution was added slowly, maintaining the batch temperature <15° C. The addition required ~3.5 h. The resulting dark green mixture was decanted into a 2 L capped bottle.

All equivalent and volume descriptors in this part are based on a 500 g reaction. A 22 L reactor was charged with a solution of benzyl chloromethyl ether (95%, 375 g, 2.31 mol, 0.8 equiv) in THF (1.5 L, 3 vol). The reactor was cooled in an ice-water bath. Two Grignard reagent batches prepared as described above were combined and then added slowly to the benzyl chloromethyl ether solution via an addition funnel, maintaining the batch temperature below 25° C. The addition required 1.5 h. The reaction mixture was stirred overnight (16 h).

All equivalent and volume descriptors in this part are based on a 1 kg reaction. A solution of 15% ammonium chloride was prepared in a 30 L jacketed reactor (1.5 kg in 8.5 kg of water, 10 vol). The solution was cooled to 5° C. Two Grignard reaction mixtures prepared as described above were combined and then transferred into the ammonium chloride solution via a header vessel. An exotherm was observed in this quench, which was carried out at a rate such as to keep the internal temperature below 25° C. Once the transfer was complete, the vessel jacket temperature was set to 25° C. Hexanes (8 L, 8 vol) was added and the mixture was stirred for 0.5 h. After settling the phases, the aqueous phase (pH 9) was drained off and discarded. The remaining organic phase was washed with water (2 L, 2 vol). The organic phase was concentrated in vacuo using a 22 L rotary evaporator, providing the crude product as an orange oil.

Method B

Magnesium turnings (106 g, 4.35 mol, 1.0 eq) were charged to a 22 L reactor and then suspended in THF (760 mL, 1 vol). The vessel was cooled in an ice-water bath such that the batch temperature reached 2° C. A solution of the propargyl chloride (760 g, 4.35 mol, 1.0 equiv) in THF (4.5 L, 6 vol) was added slowly to the reactor. After 100 mL was added, the addition was stopped and the mixture stirred until a 13° C. exotherm was observed, indicating the Grignard reagent initiation. Once the exotherm subsided, another 500 mL of the propargyl chloride solution was added slowly, maintaining the batch temperature <20° C. The Grignard reagent formation was confirmed by IPC using $^1$H-NMR spectroscopy. The remainder of the propargyl chloride solution was added slowly, maintaining the batch temperature <20° C. The addition required ~1.5 h. The resulting dark green solution was stirred for 0.5 h. The Grignard reagent formation was confirmed by IPC using $^1$H-NMR spectroscopy. Neat benzyl chloromethyl ether was charged to the reactor addition funnel and then added dropwise into the reactor, maintaining the batch temperature below 25° C. The addition required 1.0 h. The reaction mixture was stirred overnight. The aqueous work-up and concentration was carried out using the same procedure and relative amounts of materials as in Method A to give the product as an orange oil.

Synthesis of 4-Benzyloxy-3,3-dimethylbut-1-yne

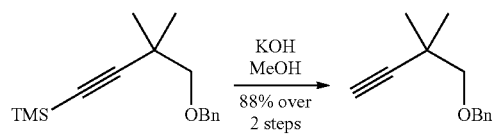 [SMILES: CC(C)(C#C[Si](C)(C)C)COCc1ccccc1 ; C#CC(C)(C)COCc1ccccc1]

A 30 L jacketed reactor was charged with methanol (6 vol) which was then cooled to 5° C. Potassium hydroxide (85%, 1.3 equiv) was added to the reactor. A 15-20° C. exotherm was observed as the potassium hydroxide dissolved. The jacket temperature was set to 25° C. A solution of 4-benzyloxy-3,3-dimethyl-1-trimethylsilylbut-1-yne (1.0 equiv) in methanol (2 vol) was added and the resulting mixture was stirred until reaction completion, as monitored by HPLC. Typical reaction time at 25° C. is 3-4 h. The reaction mixture is diluted with water (8 vol) and then stirred for 0.5 h. Hexanes (6 vol) was added and the resulting mixture was stirred for 0.5 h. The phases were allowed to settle and then the aqueous phase (pH 10-11) was drained off and discarded. The organic phase was washed with a solution of KOH (85%, 0.4 equiv) in water (8 vol) followed by water (8 vol). The organic phase was then concentrated down using a rotary evaporator, yielding the title material as a yellow-orange oil. Typical purity of this material is in the 80% range with primarily a single impurity present. $^1$H NMR (400 MHz, C$_6$D$_6$) δ 7.28 (d, 2H, J=7.4 Hz), 7.18 (t, 2H, J=7.2 Hz), 7.10 (d, 1H, J=7.2 Hz), 4.35 (s, 2H), 3.24 (s, 2H), 1.91 (s, 1H), 1.25 (s, 6H).

Synthesis of N-benzylglycolated-5-amino-2-(2-benzyloxy-1,1-dimethylethyl)-6-fluoroindole

Method A

Synthesis of Benzylglycolated 4-Amino-2-(4-benzyloxy-3,3-dimethylbut-1-ynyl)-5-fluoroaniline

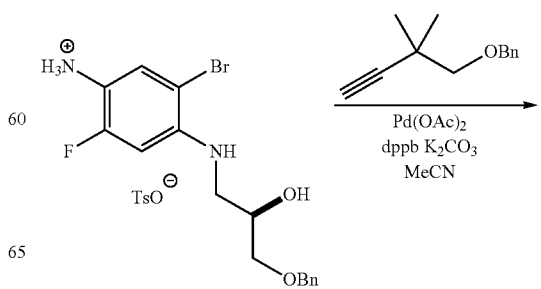

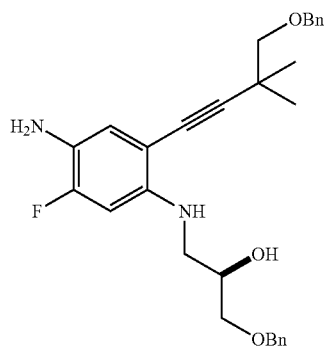

Benzylglycolated 4-ammonium-2-bromo-5-flouroaniline tosylate salt was freebased by stirring the solid in EtOAc (5 vol) and saturated NaHCO₃ solution (5 vol) until clear organic layer was achieved. The resulting layers were separated and the organic layer was washed with saturated NaHCO₃ solution (5 vol) followed by brine and concentrated in vacuo to obtain benzylglocolated 4-ammonium-2-bromo-5-flouroaniline tosylate salt as an oil.

Then, a flask was charged with benzylglycolated 4-ammonium-2-bromo-5-flouroaniline tosylate salt (freebase, 1.0 equiv), Pd(OAc) (4.0 mol %), dppb (6.0 mol %) and powdered K₂CO₃ (3.0 equiv) and stirred with acetonitrile (6 vol) at room temperature. The resulting reaction mixture was degassed for approximately 30 min by bubbling in N₂ with vent. Then 4-benzyloxy-3,3-dimethylbut-1-yne (1.1 equiv) dissolved in acetonitrile (2 vol) was added in a fast stream and heated to 80° C. and stirred until complete consumption of 4-ammonium-2-bromo-5-flouroaniline tosylate salt was achieved. The reaction slurry was cooled to room temperature and filtered through a pad of Celite and washed with acetonitrile (2 vol). Filtrate was concentrated in vacuo and the residue was redissolved in EtOAc (6 vol). The organic layer was washed twice with NH₄Cl solution (20% w/v, 4 vol) and brine (6 vol). The resulting organic layer was concentrated to yield brown oil and used as is in the next reaction.

Synthesis of N-benzylglycolated-5-amino-2-(2-benzyloxy-1,1-dimethylethyl)-6-fluoroindole

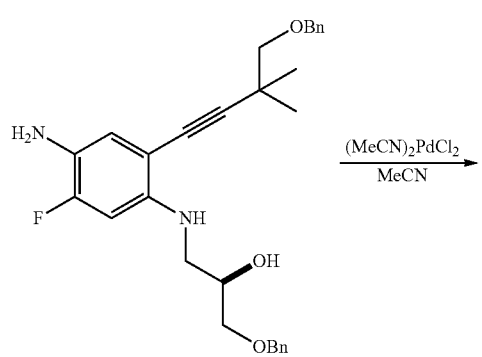

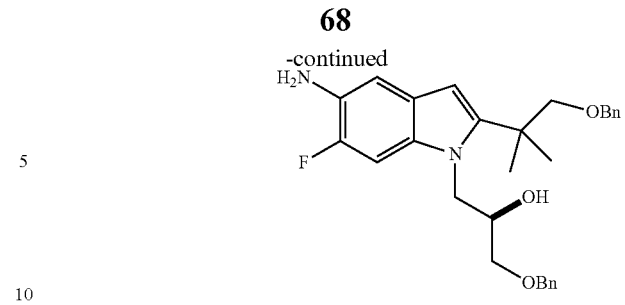

Crude oil of benzylglycolated 4-amino-2-(4-benzyloxy-3,3-dimethylbut-1-ynyl)-5-fluoroaniline was dissolved in acetonitrile (6 vol) and added (MeCN)₂PdCl₂ (15 mol %) at room temperature. The resulting mixture was degassed using N₂ with vent for approximately 30 min. Then the reaction mixture was stirred at 80° C. under N₂ blanket overnight. The reaction mixture was cooled to room temperature and filtered through a pad of Celite and washed the cake with acetonitrile (1 vol). The resulting filtrate was concentrated in vacuo and redissolved in EtOAc (5 vol). Deloxane-II THP (5 wt % based on the theoretical yield of N-benzylglycolated-5-amino-2-(2-benzyloxy-1,1-dimethylethyl)-6-fluoroindole) was added and stirred at room temperature overnight. The mixture was then filtered through a pad of silica (2.5 inch depth, 6 inch diameter filter) and washed with EtOAc (4 vol). The filtrate was concentrated down to a dark brown residue, and used as is in the next reaction.

Repurification of Crude N-benzylglycolated-5-amino-2-(2-benzyloxy-1,1-dimethylethyl)-6-fluoroindole The crude N-benzylglycolated-5-amino-2-(2-benzyloxy-1,1-dimethylethyl)-6-fluoroindole was dissolved in dichloromethane (~1.5 vol) and filtered through a pad of silica initially using 30% EtOAc/heptane where impurities were discarded. Then the silica pad was washed with 50% EtOAc/heptane to isolate N-benzylglycolated-5-amino-2-(2-benzyloxy-1,1-dimethylethyl)-6-fluoroindole until faint color was observed in the filtrate. This filtrate was concentrated in vacuo to afford brown oil which crystallized on standing at room temperature. ¹H NMR (400 MHz, DMSO) δ 7.38-7.34 (m, 4H), 7.32-7.23 (m, 6H), 7.21 (d, 1H, J=12.8 Hz), 6.77 (d, 1H, J=9.0 Hz), 6.06 (s, 1H), 5.13 (d, 1H, J=4.9 Hz), 4.54 (s, 2H), 4.46 (br. s, 2H), 4.45 (s, 2H), 4.33 (d, 1H, J=12.4 Hz), 4.09-4.04 (m, 2H), 3.63 (d, 1H, J=9.2 Hz), 3.56 (d, 1H, J=9.2 Hz), 3.49 (dd, 1H, J=9.8, 4.4 Hz), 3.43 (dd, 1H, J=9.8, 5.7 Hz), 1.40 (s, 6H).

Synthesis of N-benzylglycolated-5-amino-2-(2-benzyloxy-1,1-dimethylethyl)-6-fluoroindole Method B

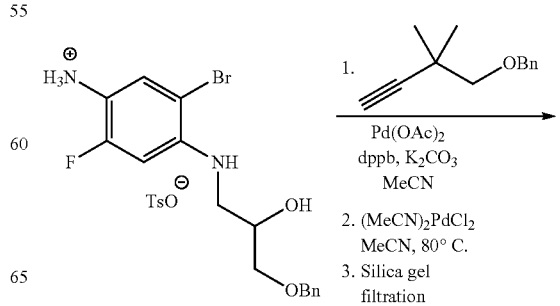

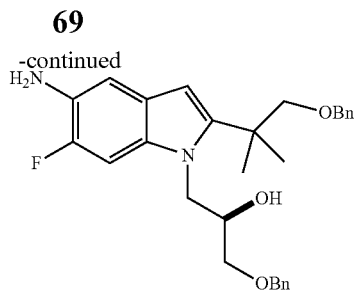

Palladium acetate (33 g, 0.04 eq), dppb (94 g, 0.06 eq), and potassium carbonate (1.5 kg, 3.0 eq) are charged to a reactor. The free based oil benzylglocolated 4-ammonium-2-bromo-5-flouroaniline (1.5 kg, 1.0 eq) was dissolved in acetonitrile (8.2 L, 4.1 vol) and then added to the reactor. The mixture was sparged with nitrogen gas for NLT 1 h. A solution of 4-benzyloxy-3,3-dimethylbut-1-yne (70%, 1.1 kg, 1.05 eq) in acetonitrile was added to the mixture which was then sparged with nitrogen gas for NLT 1 h. The mixture was heated to 80° C. and then stirred overnight. IPC by HPLC is carried out and the reaction is determined to be complete after 16 h. The mixture was cooled to ambient temperature and then filtered through a pad of Celite (228 g). The reactor and Celite pad were washed with acetonitrile (2×2 L, 2 vol). The combined phases are concentrated on a 22 L rotary evaporator until 8 L of solvent have been collected, leaving the crude product in 7 L (3.5 vol) of acetonitrile.

Bis-acetonitriledichloropalladium (144 g, 0.15 eq) was charged to the reactor. The crude solution was transferred back into the reactor and the roto-vap bulb was washed with acetonitrile (4 L, 2 vol). The combined solutions were sparged with nitrogen gas for NLT 1 h. The reaction mixture was heated to 80° C. for NLT 16 h. In process control by HPLC shows complete consumption of starting material. The reaction mixture was filtered through Celite (300 g). The reactor and filter cake were washed with acetonitrile (3 L, 1.5 vol). The combined filtrates were concentrated to an oil by rotary evaporation. The oil was dissolved in ethyl acetate (8.8 L, 4.4 vol). The solution was washed with 20% ammonium chloride (5 L, 2.5 vol) followed by 5% brine (5 L, 2.5 vol). Silica gel (3.5 kg, 1.8 wt. eq.) of silica gel was added to the organic phase, which was stirred overnight. Deloxan THP II metal scavenger (358 g) and heptane (17.6 L) were added and the resulting mixture was stirred for NLT 3 h. The mixture was filtered through a sintered glass funnel. The filter cake was washed with 30% ethyl acetate in heptane (25 L). The combined filtrates were concentrated under reduced pressure to give N-benzylglycolated-5-amino-2-(2-benzyloxy-1,1-dimethyl ethyl)-6-fluoroindole as a brown paste (1.4 kg).

Synthesis of Compound 1

Synthesis of Benzyl Protected Compound 1

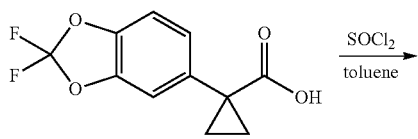

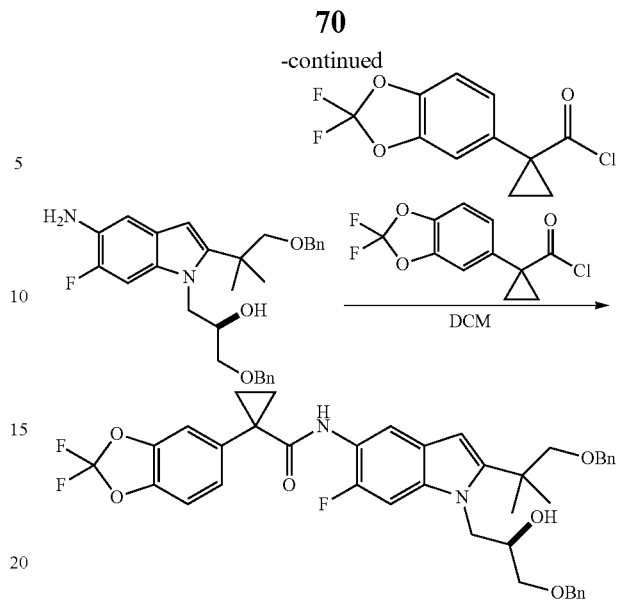

1-(2,2-difluoro-1,3-benzodioxol-5-yl)-cyclopropanecarboxylic acid (1.3 equiv) was slurried in toluene (2.5 vol, based on 1-(2,2-difluoro-1,3-benzodioxol-5-yl)-cyclopropanecarboxylic acid) and the mixture was heated to 60° C. SOCl₂ (1.7 equiv) was added via addition funnel. The resulting mixture was stirred for 2 hr. The toluene and the excess SOCl₂ were distilled off using rotavop. Additional toluene (2.5 vol, based on 1-(2,2-difluoro-1,3-benzodioxol-5-yl)-cyclopropanecarboxylic acid) was added and distilled again. The crude acid chloride was dissolved in dichloromethane (2 vol) and added via addition funnel to a mixture of N-benzylglycolated-5-amino-2-(2-benzyloxy-1,1-dimethylethyl)-6-fluoroindole (1.0 equiv), and triethylamine (2.0 equiv) in dichloromethane (7 vol) while maintaining 0-3° C. (internal temperature). The resulting mixture was stirred at 0° C. for 4 hrs and then warmed to room temperature overnight. Distilled water (5 vol) was added to the reaction mixture and stirred for NLT 30 min and the layers were separated. The organic phase was washed with 20 wt % K₂CO₃ (4 vol×2) followed by a brine wash (4 vol) and concentrated to afford crude benzyl protected Compound 1 as a thick brown oil, which was purified further using silica pad filtration.

Silica Gel Pad Filtration:

Crude benzyl protected Compound 1 was dissolved in ethyl acetate (3 vol) in the presence of activated carbon Darco-G (10 wt %, based on theoretical yield of benzyl protected Compound 1) and stirred at room temperature overnight. To this mixture was added heptane (3 vol) and filtered through a pad of silica gel (2× weight of crude benzyl protected Compound 1). The silica pad was washed with ethyl acetate/heptane (1:1, 6 vol) or until little color was detected in the filtrate. The filtrate was concentrated in vacuo to afford benzyl protected Compound 1 as viscous reddish brown oil, and used directly in the next step.

Repurification:

Benzyl protected Compound 1 was redissolved in dichloromethane (1 vol, based on theoretical yield of benzyl protected Compound 1) and loaded onto a silica gel pad (2× weight of crude benzyl protected Compound 1). The silica pad was washed with dichloromethane (2 vol, based on theoretical yield of benzyl protected Compound 1) and the filtrate was discarded. The silica pad was washed with 30% ethyl acetate/heptane (5 vol) and the filtrate was concentrated in vacuo to afford benzyl protected Compound 1 as viscous reddish orange oil, and used directly in the next step.

Synthesis of Compound 1

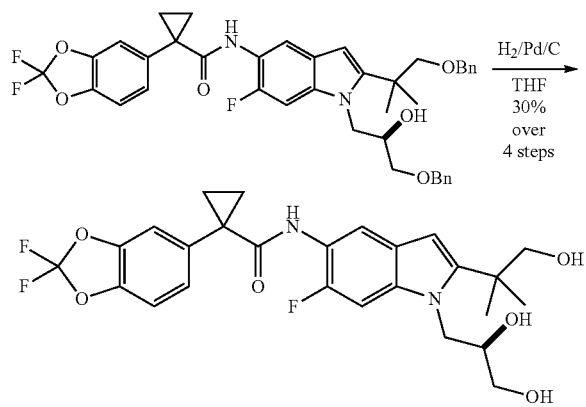

Method A

A 20 L autoclave was flushed three times with nitrogen gas and then charged with palladium on carbon (Evonik E 101 NN/W, 5% Pd, 60% wet, 200 g, 0.075 mol, 0.04 equiv). The autoclave was then flushed with nitrogen three times. A solution of crude benzyl protected Compound 1 (1.3 kg, ~1.9 mol) in THF (8 L, 6 vol) was added to the autoclave via suction. The vessel was capped and then flushed three times with nitrogen gas. With gentle stirring, the vessel was flushed three times with hydrogen gas, evacuating to atmosphere by diluting with nitrogen. The autoclave was pressurized to 3 Bar with hydrogen and the agitation rate was increased to 800 rpm. Rapid hydrogen uptake was observed (dissolution). Once uptake subsided, the vessel was heated to 50° C.

For safety purposes, the thermostat was shut off at the end of every work-day. The vessel was pressurized to 4 Bar with hydrogen and then isolated from the hydrogen tank.

After 2 full days of reaction, more Pd/C (60 g, 0.023 mol, 0.01 equiv) was added to the mixture. This was done by flushing three times with nitrogen gas and then adding the catalyst through the solids addition port. Resuming the reaction was done as before. After 4 full days, the reaction was deemed complete by HPLC by the disappearance of not only the starting material but also of the peak corresponding to a mono-benzylated intermediate.

The reaction mixture was filtered through a Celite pad. The vessel and filter cake were washed with THF (2 L, 1.5 vol). The Celite pad was then wetted with water and the cake discarded appropriately. The combined filtrate and THF wash were concentrated using a rotary evaporator yielding the crude product as a black oil, 1 kg.

The equivalents and volumes in the following purification are based on 1 kg of crude material. The crude black oil was dissolved in 1:1 ethyl acetate-heptane. The mixture was charged to a pad of silica gel (1.5 kg, 1.5 wt. equiv) in a fritted funnel that had been saturated with 1:1 ethyl acetate-heptane. The silica pad was flushed first with 1:1 ethyl acetate-heptane (6 L, 6 vol) and then with pure ethyl acetate (14 L, 14 vol). The eluent was collected in 4 fractions which were analyzed by HPLC.

The equivalents and volumes in the following purification are based on 0.6 kg of crude material. Fraction 3 was concentrated by rotary evaporation to give a brown foam (600 g) and then redissolved in MTBE (1.8 L, 3 vol). The dark brown solution was stirred overnight at ambient temperature, during which time, crystallization occurred. Heptane (55 mL, 0.1 vol) was added and the mixture was stirred overnight. The mixture was filtered using a Buchner funnel and the filter cake was washed with 3:1 MTBE-heptane (900 mL, 1.5 vol). The filter cake was air-dried for 1 h and then vacuum dried at ambient temperature for 16 h, furnishing 253 g of Compound 1 as an off-white solid.

The equivalents and volumes for the following purification are based on 1.4 kg of crude material. Fractions 2 and 3 from the above silica gel filtration as well as material from a previous reaction were combined and concentrated to give 1.4 kg of a black oil. The mixture was resubmitted to the silica gel filtration (1.5 kg of silica gel, eluted with 3.5 L, 2.3 vol of 1:1 ethyl acetate-heptane then 9 L, 6 vol of pure ethyl acetate) described above, which upon concentration gave a tan foamy solid (390 g).

The equivalents and volumes for the following purification are based on 390 g of crude material. The tan solid was insoluble in MTBE, so was dissolved in methanol (1.2 L, 3 vol). Using a 4 L Morton reactor equipped with a long-path distillation head, the mixture was distilled down to 2 vol. MTBE (1.2 L, 3 vol) was added and the mixture was distilled back down to 2 vol. A second portion of MTBE (1.6 L, 4 vol) was added and the mixture was distilled back down to 2 vol. A third portion of MTBE (1.2 L, 3 vol) was added and the mixture was distilled back down to 3 vol. Analysis of the distillate by GC revealed it to consist of ~6% methanol. The thermostat was set to 48° C. (below the boiling temp of the MTBE-methanol azeotrope, which is 52° C.). The mixture was cooled to 20° C. over 2 h, during which time a relatively fast crystallization occurred. After stirring the mixture for 2 h, heptane (20 mL, 0.05 vol) was added and the mixture was stirred overnight (16 h). The mixture was filtered using a Buchner funnel and the filter cake was washed with 3:1 MTBE-heptane (800 mL, 2 vol). The filter cake was air-dried for 1 h and then vacuum dried at ambient temperature for 16 h, furnishing 130 g of Compound 1 as an off-white solid.

Method B

Benzyl protected Compound 1 was dissolved in THF (3 vol) and then stripped to dryness to remove any residual solvent. Benzyl protected Compound 1 was redissolved in THF (4 vol) and added to the hydrogenator containing 5 wt % Pd/C (2.5 mol %, 60% wet, Degussa E5 E101 NN/W). The internal temperature of the reaction was adjusted to 50° C., and flushed with $N_2$ (×5) followed by hydrogen (×3). The hydrogenator pressure was adjusted to 3 Bar of hydrogen and the mixture was stirred rapidly (>1100 rpm). At the end of the reaction, the catalyst was filtered through a pad of Celite and washed with THF (1 vol). The filtrate was concentrated in vacuo to obtain a brown foamy residue. The resulting residue was dissolved in MTBE (5 vol) and 0.5N HCl solution (2 vol) and distilled water (1 vol) were added. The mixture was stirred for NLT 30 min and the resulting layers were separated. The organic phase was washed with 10 wt % $K_2CO_3$ solution (2 vol×2) followed by a brine wash. The organic layer was added to a flask containing silica gel (25 wt %), Deloxan-THP II (5 wt %, 75% wet), and $Na_2SO_4$ and stirred overnight. The resulting mixture was filtered through a pad of Celite and washed with 10% THF/MTBE (3 vol). The filtrate was concentrated in vacuo to afford crude Compound 1 as pale tan foam.

Compound 1 Recovery from the Mother Liquor: Option A.

Silica gel pad filtration: The mother liquor was concentrated in vacuo to obtain a brown foam, dissolved in dichloromethane (2 vol), and filtered through a pad of silica (3× weight of the crude Compound 1). The silica pad was washed with ethyl acetate/heptane (1:1, 13 vol) and the filtrate was discarded. The silica pad was washed with 10% THF/ethyl acetate (10 vol) and the filtrate was concentrated in vacuo to afford Compound 1 as pale tan foam. The above crystallization procedure was followed to isolate the remaining Compound 1.

Compound 1 Recovery from the Mother Liquor: Option B.

Silica gel column chromatography: After chromatography on silica gel (50% ethyl acetate/hexanes to 100% ethyl acetate), the desired compound was isolated as pale tan foam. The above crystallization procedure was followed to isolate the remaining Compound 1.

Additional Recrystallization of Compound 1

Solid Compound 1 (1.35 kg) was suspended in IPA (5.4 L, 4 vol) and then heated to 82° C. Upon complete dissolution (visual), heptane (540 mL, 0.4 vol) was added slowly. The mixture was cooled to 58° C. The mixture was then cooled slowly to 51° C., during which time crystallization occurs. The heat source was shut down and the recrystallization mixture was allowed to cool naturally overnight. The mixture was filtered using a benchtop Buchner funnel and the filter cake was washed with IPA (2.7 L, 2 vol). The filter cake was dried in the funnel under air flow for 8 h and then was oven-dried in vacuo at 45-50° C. overnight to give 1.02 kg of recrystallized Compound 1.

Compound 1 may also be prepared by one of several synthetic routes disclosed in US published patent application US20090131492, incorporated herein by reference.

Table 6 below recites analytical data for Compound 1.

TABLE 6

| Cmpd. No. | LC/MS M + 1 | LC/RT min | NMR |
|---|---|---|---|
| 1 | 521.5 | 1.69 | 1H NMR (400.0 MHz, CD$_3$CN) d 7.69 (d, J = 7.7 Hz, 1H), 7.44 (d, J = 1.6 Hz, 1H), 7.39 (dd, J = 1.7, 8.3 Hz, 1H), 7.31 (s, 1H), 7.27 (d, J = 8.3 Hz, 1H), 7.20 (d, J = 12.0 Hz, 1H), 6.34 (s, 1H), 4.32 (d, J = 6.8 Hz, 2H), 4.15-4.09 (m, 1H), 3.89 (dd, J = 6.0, 11.5 Hz, 1H), 3.63-3.52 (m, 3H), 3.42 (d, J = 4.6 Hz, 1H), 3.21 (dd, J = 6.2, 7.2 Hz, 1H), 3.04 (t, J = 5.8 Hz, 1H), 1.59 (dd, J = 3.8, 6.8 Hz, 2H), 1.44 (s, 3H), 1.33 (s, 3H) and 1.18 (dd, J = 3.7, 6.8 Hz, 2H) ppm. |

Synthesis of Compound 1 Amorphous Form

Spray-Dried Method 9.95 g of Hydroxypropylmethylcellulose acetate succinate HG grade (HPMCAS-HG) was weighed into a 500 ml beaker, along with 50 mg of sodium lauryl sulfate (SLS). MeOH (200 ml) was mixed with the solid. The material was allowed to stir for 4 h. To insure maximum dissolution, after 2 h of stirring the solution was sonicated for 5 mins, then allowed to continue stirring for the remaining 2 h. A very fin suspension of HPMCAS remained in solution. However, visual observation determined that no gummy portions remained on the walls of the vessel or stuck to the bottom after tilting the vessel.

Compound 1 (10 g) was poured into the 500 ml beaker, and the system was allowed to continue stirring. The solution was spray dried using the following parameters:

| Formulation Description: Compound 1 Form A/HPMCAS/SLS (50/49.5/0.5) Buchi Mini Spray Dryer | |
|---|---|
| T inlet (setpoint) | 145° C. |
| T outlet (start) | 75° C. |
| T outlet (end) | 55° C. |
| Nitrogen Pressure | 75 psi |
| Aspirator | 100% |
| Pump | 35% |
| Rotometer | 40 mm |
| Filter Pressure | 65 mbar |
| Condenser Temp | −3° C. |
| Run Time | 1 h |

Figure 2:
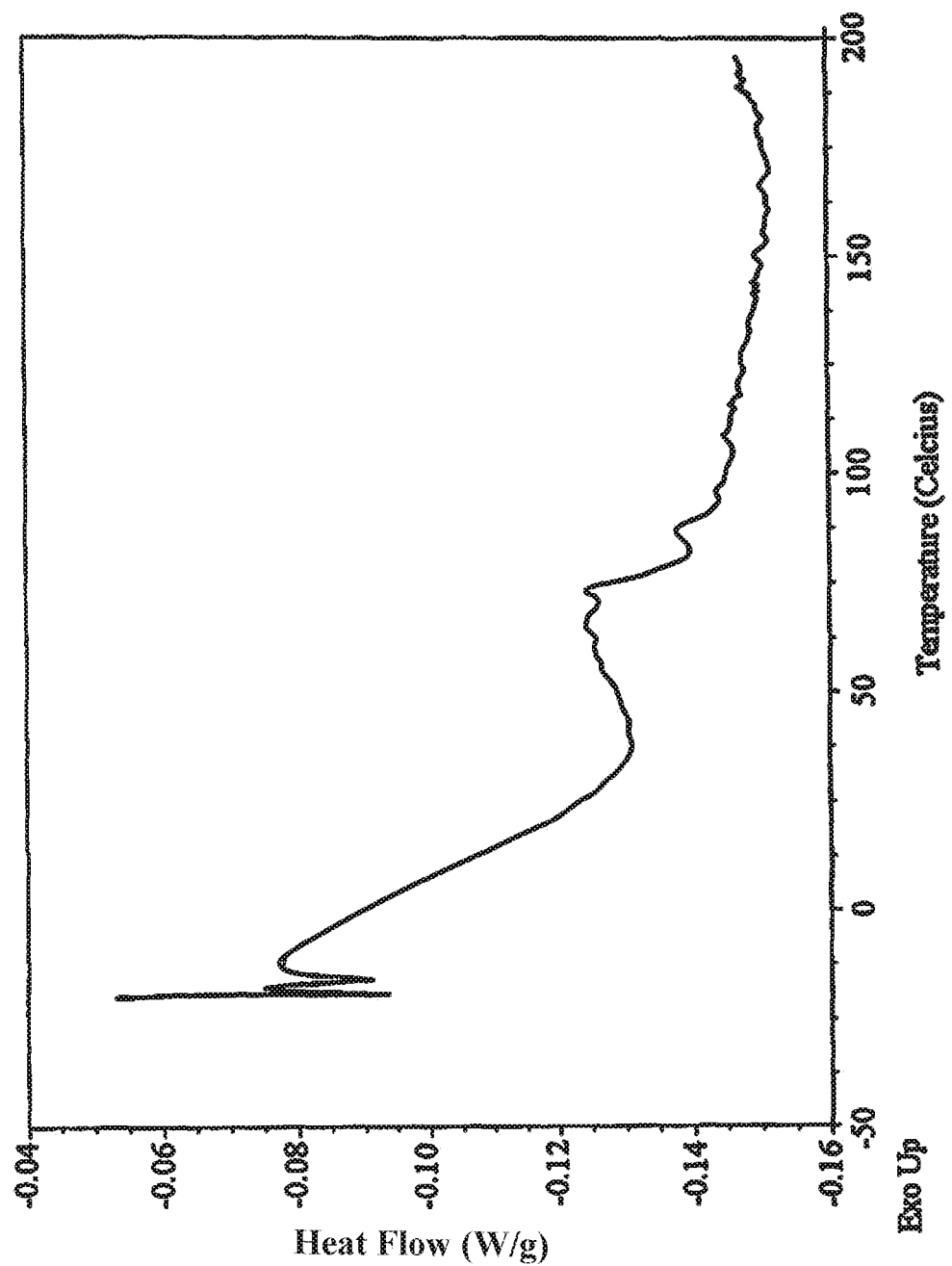
FIG. 2 is a modulated differential scanning calorimetry (MDSC) trace of Compound 1 Amorphous Form prepared by spray dried methods.

Approximately 16 g of Compound 1 Amorphous Form (80% yield) was recovered. Compound 1 Amorphous Form was confirmed by XRPD (FIG. 1) and DSC (FIG. 2).

Figure 3:
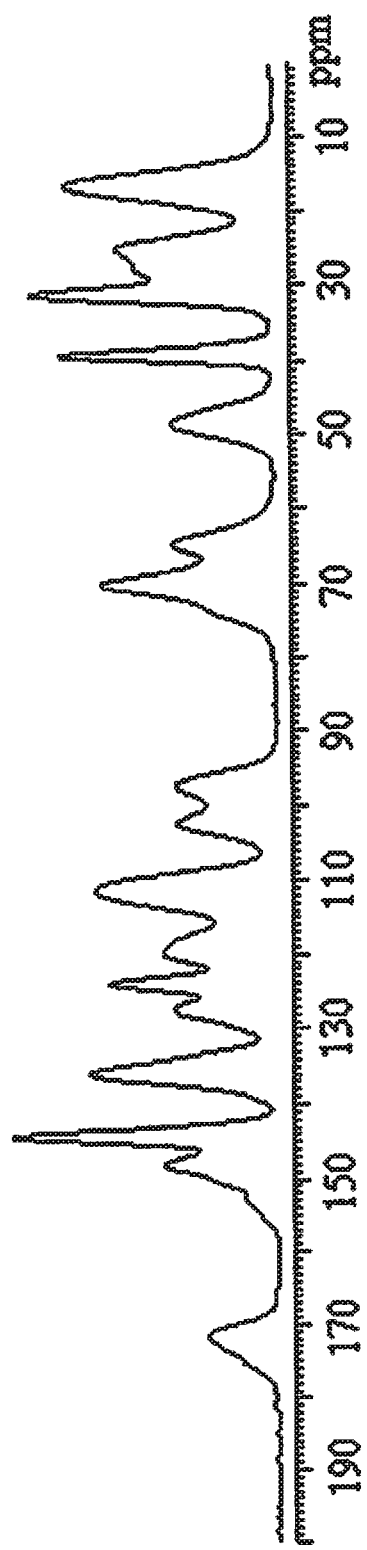
FIG. 3 is a solid state $^{13}$C NMR spectrum (15.0 kHz spinning) of Compound 1 Amorphous Form.

A solid state $^{13}$C NMR spectrum of Compound 1 Amorphous Form is shown in FIG. 3. Table 7 provides chemical shifts of the relevant peaks.

TABLE 7

| | Compound 1 Amorphous Form $^{13}$C Chem. Shifts | |
|---|---|---|
| Peak # | F1 [ppm] | Intensity |
| 1 | 171.6 | 26.33 |
| 2 | 147.9 | 41.9 |
| 3 | 144.0 | 100 |
| 4 | 135.8 | 70.41 |
| 5 | 127.3 | 38.04 |
| 6 | 123.8 | 62.66 |
| 7 | 119.8 | 42.09 |
| 8 | 111.2 | 68.11 |

TABLE 7-continued

| | Compound 1 Amorphous Form $^{13}$C Chem. Shifts | |
|---|---|---|
| Peak # | F1 [ppm] | Intensity |
| 9 | 102.4 | 37.01 |
| 10 | 97.5 | 37.47 |
| 11 | 70.0 | 65.02 |
| 12 | 64.7 | 37.94 |
| 13 | 48.3 | 38.16 |
| 14 | 39.1 | 80.54 |
| 15 | 31.1 | 92.01 |
| 16 | 25.1 | 58.68 |
| 17 | 16.5 | 78.97 |

Figure 4:
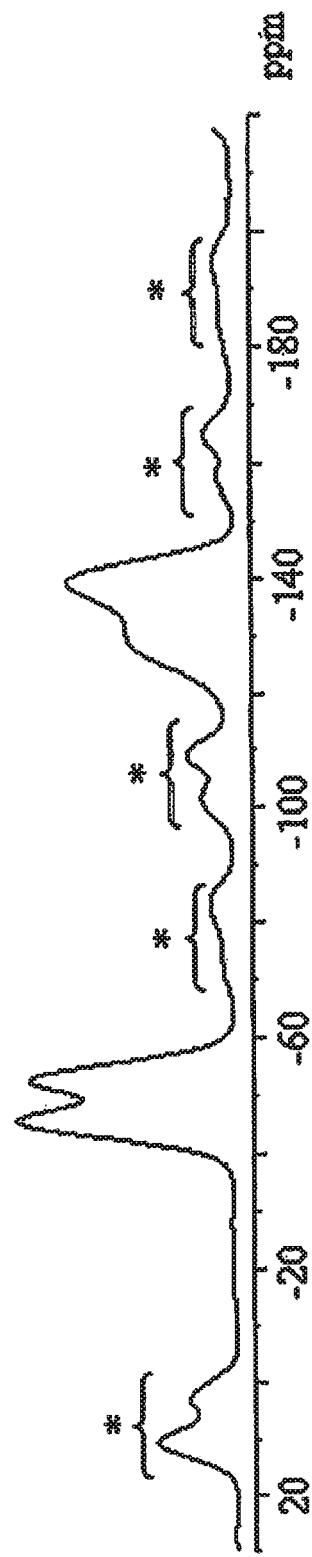
FIG. 4 is a solid state $^{19}$F NMR spectrum (12.5 kHz spinning) of Compound 1 Amorphous Form.

A solid state $^{19}$F NMR spectrum of Compound 1 Amorphous Form is shown in FIG. 4. Peaks with an asterisk denote spinning side bands. Table 8 provides chemical shifts of the relevant peaks.

TABLE 8

| | Compound 1 Amorphous Form $^{19}$F Chem. Shifts | |
|---|---|---|
| Peak # | F1 [ppm] | Intensity |
| 1 | −46.1 | 100 |
| 2 | −53.1 | 94.9 |
| 3 | −139.4 | 76.05 |

Rotary Evaporation Method

Figure 5:
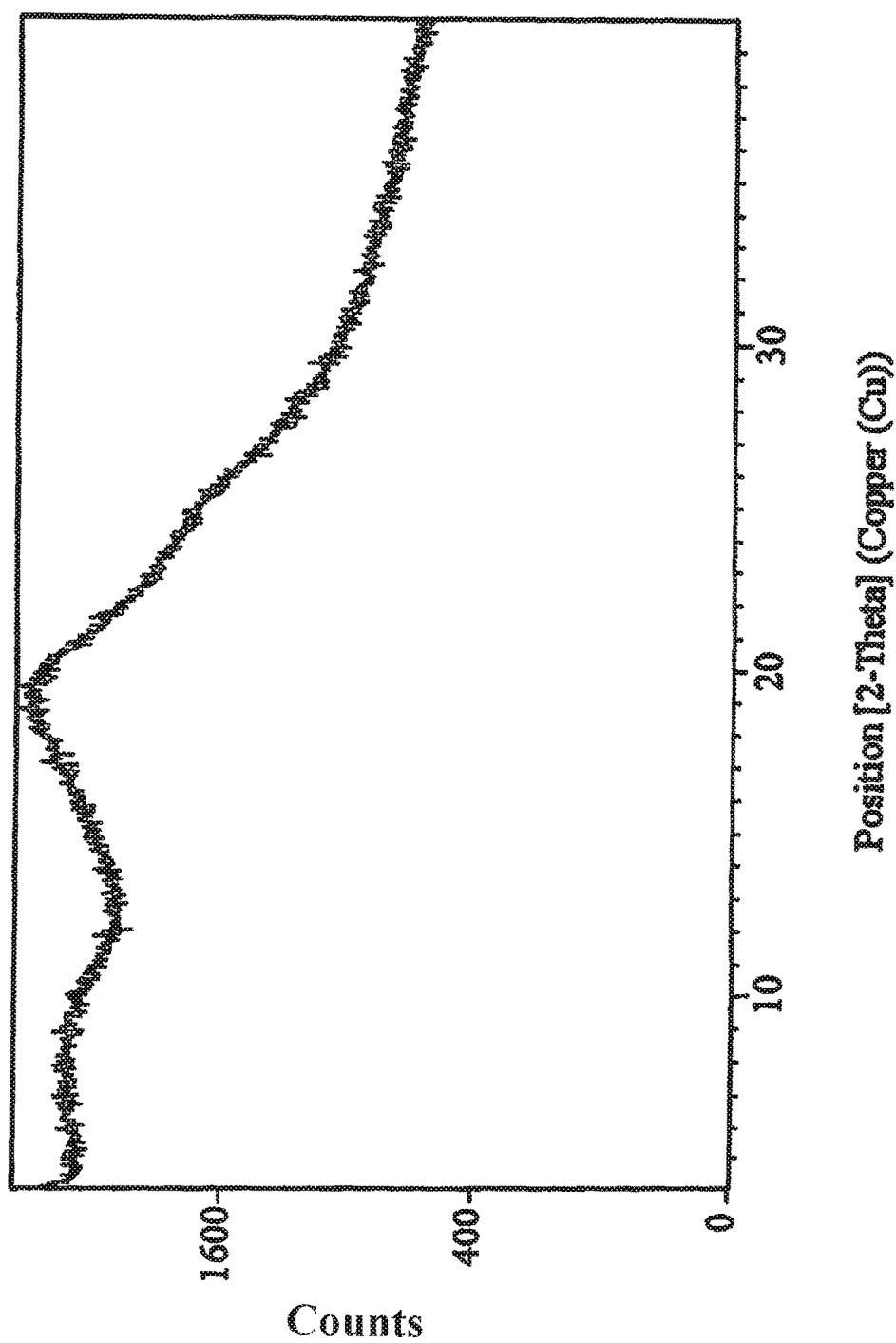
FIG. 5 is an X-ray powder diffraction pattern of Compound 1 Amorphous Form prepared by rotary evaporation methods.
Figure 6:
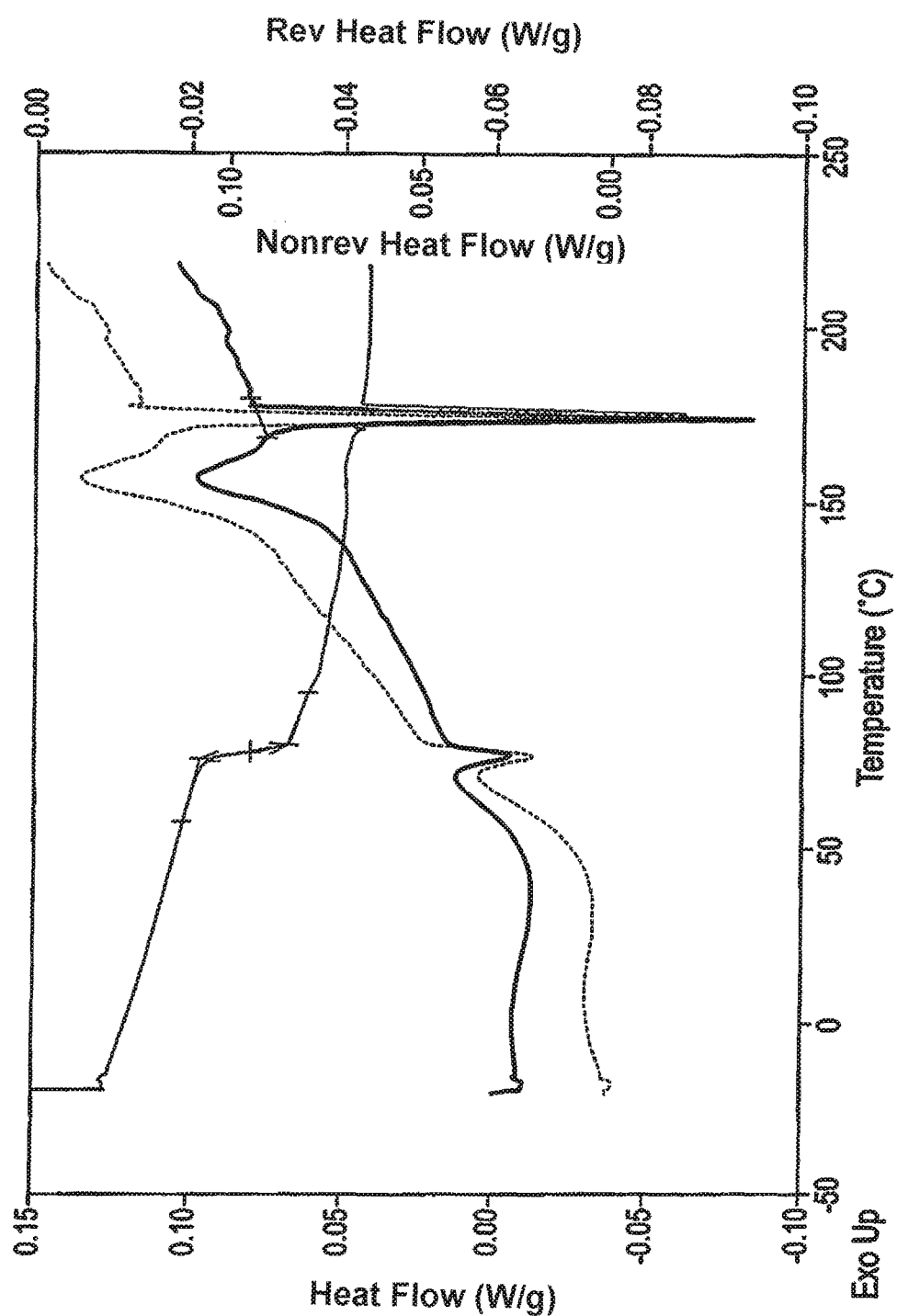
FIG. 6 is a modulated differential scanning calorimetry (MDSC) trace of Compound 1 Amorphous Form prepared by rotary evaporation methods.

Compound 1 (approximately 10 g) was dissolved in 180 ml of MeOH and rotary evaporated in a 50° C. bath to a foam. XRPD (FIG. 5) and DSC (FIG. 6) confirmed amorphous form of Compound 1.

Synthesis of Compound 1 Form A

Slurry Method

Figure 7:
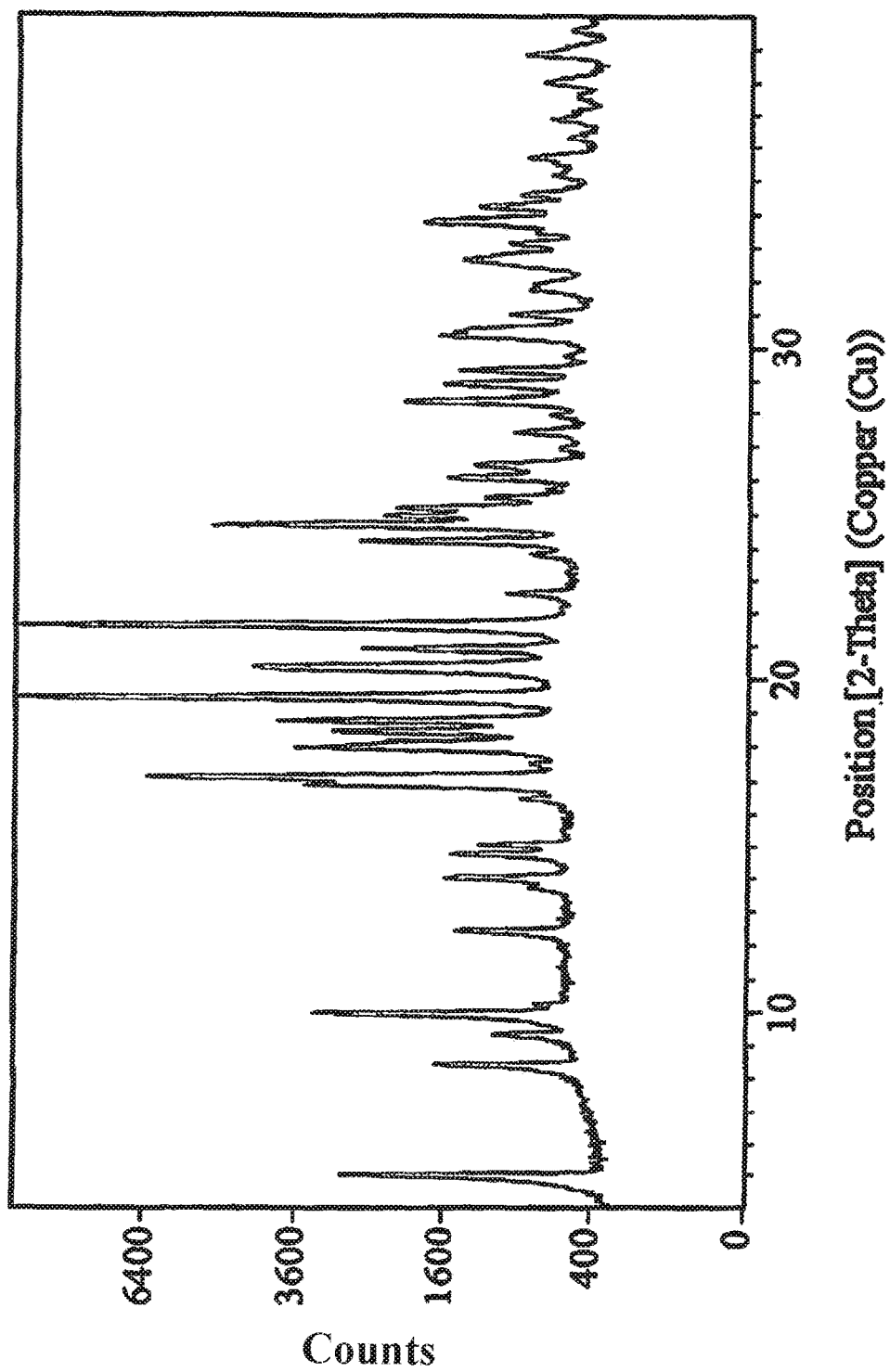
FIG. 7 is an actual X-ray powder diffraction pattern of Compound 1 Form A prepared by the slurry technique (2 weeks) with DCM as the solvent.

For EtOAc, MTBE, Isopropyl acetate, or DCM, approximately 40 mg of Compound 1 was added to a vial along with 1-2 ml of any one of the above solvents. The slurry was stirred at room temperature for 24 h to 2 weeks and Compound 1 Form A was collected by centrifuging the suspension (with filter). FIG. 7 discloses an actual XRPD pattern of Compound 1 Form A obtained by this method with DCM as the solvent. Table 9 lists the peaks for FIG. 7.

TABLE 9

| Peak Rank | 2θ Angle [degrees] | Relative Intensity [%] |
|---|---|---|
| 1 | 19.5 | 100.0 |
| 2 | 21.7 | 88.2 |
| 3 | 17.1 | 85.1 |
| 4 | 20.4 | 80.9 |
| 5 | 18.8 | 51.0 |
| 6 | 24.7 | 40.8 |
| 7 | 10.0 | 40.7 |
| 8 | 5.0 | 39.0 |
| 9 | 24.2 | 35.4 |
| 10 | 18.5 | 35.0 |
| 11 | 18.0 | 29.0 |
| 12 | 20.9 | 27.0 |
| 13 | 14.8 | 19.9 |
| 14 | 14.1 | 19.2 |
| 15 | 12.4 | 18.2 |
| 16 | 8.4 | 14.1 |

Figure 8:
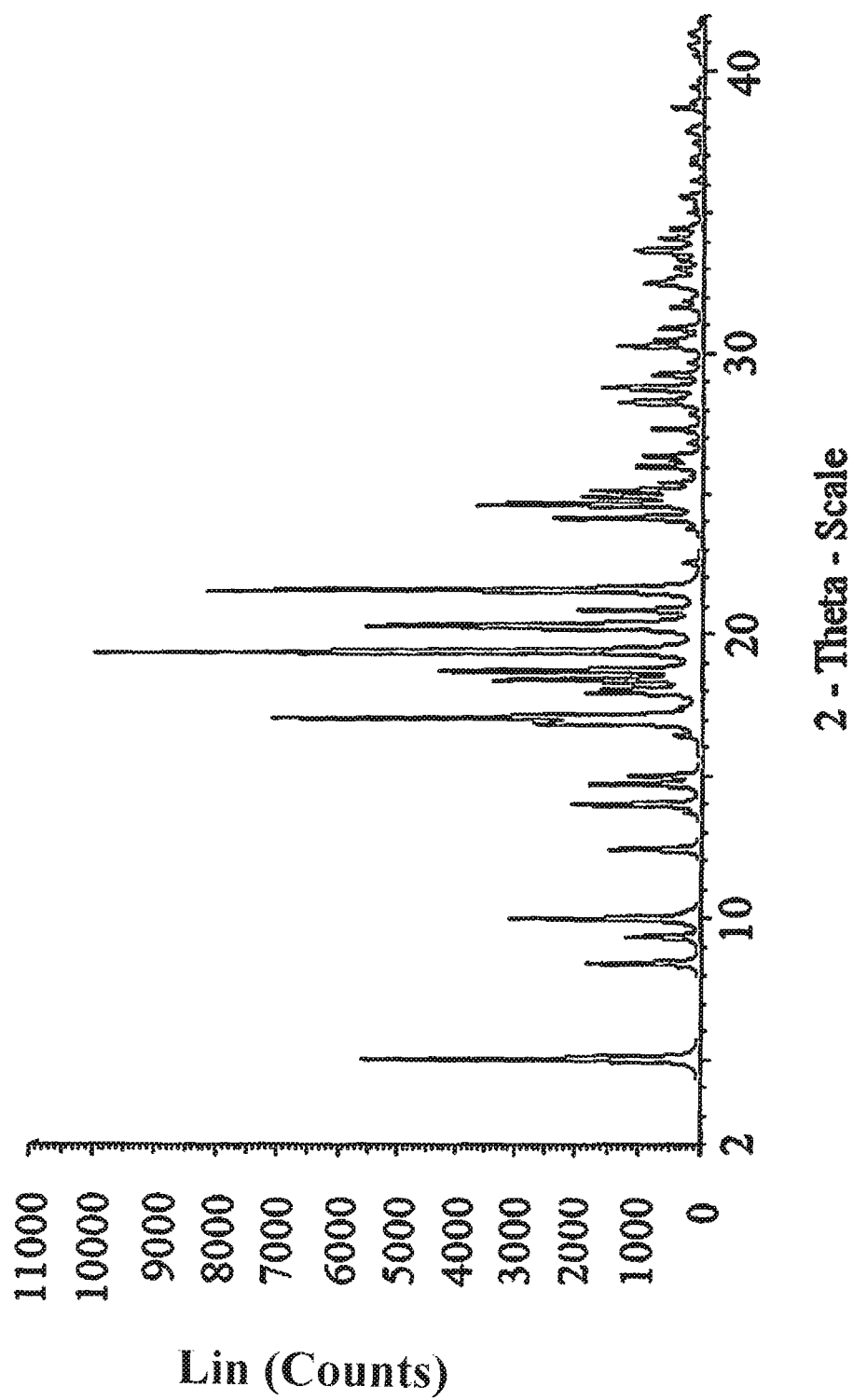
FIG. 8 is an X-ray powder diffraction pattern calculated from a single crystal of Compound 1 Form A.

An X-ray diffraction pattern calculated from a single crystal structure of Compound 1 Form A is shown in FIG. 8. Table 10 lists the calculated peaks for FIG. 8.

TABLE 10

| Peak Rank | 2θ Angle [degrees] | Relative Intensity [%] |
|---|---|---|
| 1 | 19.4 | 100.0 |
| 2 | 21.6 | 81.9 |
| 3 | 17.1 | 71.4 |
| 4 | 5.0 | 56.1 |
| 5 | 20.3 | 49.6 |
| 6 | 18.8 | 43.4 |
| 7 | 24.7 | 36.6 |
| 8 | 18.4 | 33.9 |

TABLE 10-continued

| Peak Rank | 2θ Angle [degrees] | Relative Intensity [%] |
|---|---|---|
| 9 | 10.0 | 31.2 |
| 10 | 24.2 | 24.0 |
| 11 | 14.0 | 20.7 |
| 12 | 20.9 | 19.9 |
| 13 | 8.4 | 18.4 |
| 14 | 14.7 | 18.2 |
| 15 | 18.0 | 16.0 |
| 16 | 12.4 | 14.9 |

Figure 9:
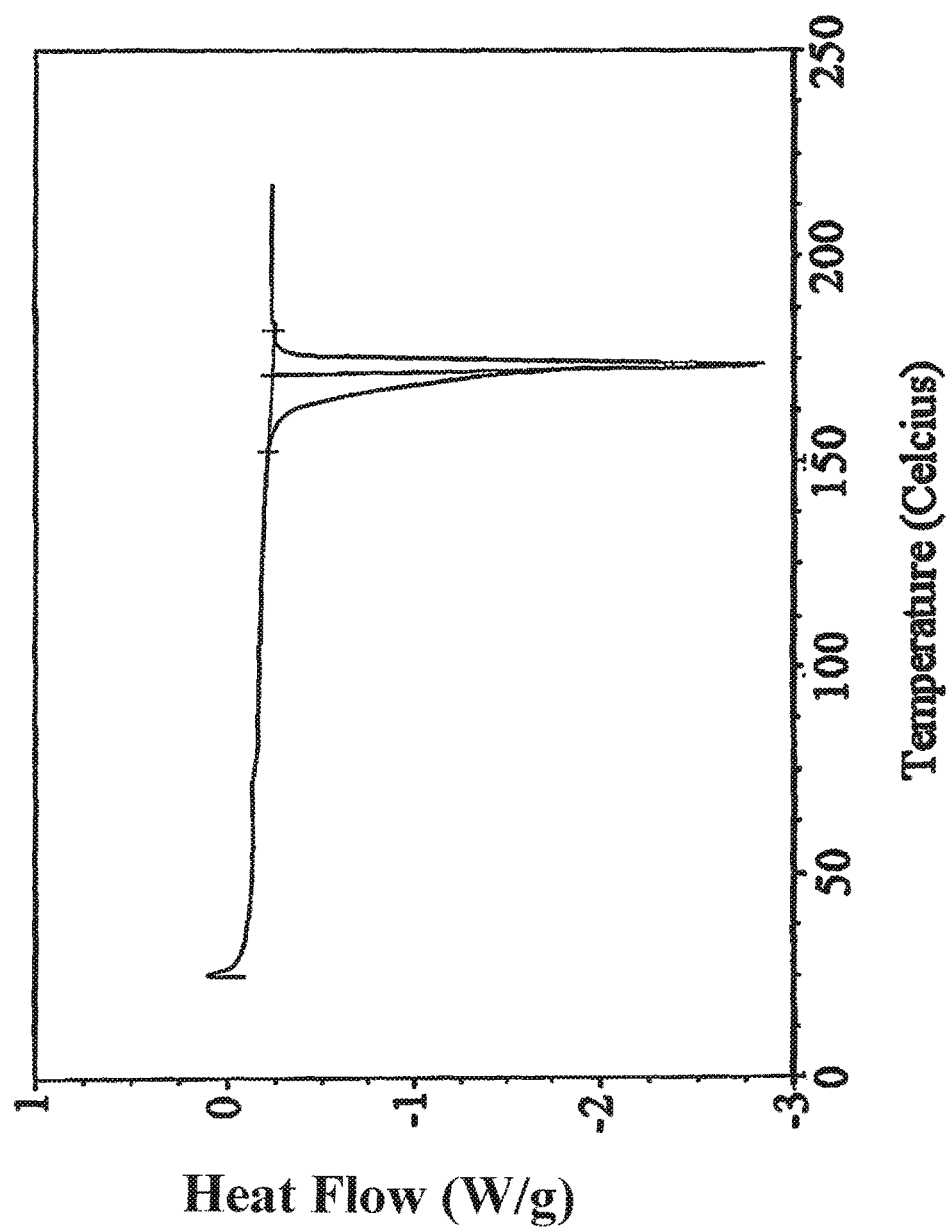
FIG. 9 is a differential scanning calorimetry (DSC) trace of Compound 1 Form A.

The DSC trace of Compound 1 Form A is shown in FIG. 9. Melting point for Compound 1 Form A occurs at about 172-178° C.

For EtOH/water solutions, approximately 40 mg of Compound 1 was added to three separate vials. In the first vial, 1.35 ml of EtOH and 0.15 ml of water were added. In the second vial, 0.75 ml of EtOH and 0.75 ml of water were added. In the third vial, 0.15 ml of EtOH and 1.35 ml of water were added. All three vials were stirred at room temperature for 24 h. Each suspension was then centrifuged separately (with filter) to collect Compound 1 Form A.

For isopropyl alcohol/water solutions, approximately 40 mg of Compound 1 was added to three separate vials. In the first vial, 1.35 ml of isopropyl alcohol and 0.15 ml of water were added. In the second vial, 0.75 ml of isopropyl alcohol and 0.75 ml of water were added. In the third vial, 0.15 ml of isopropyl alcohol and 1.35 ml of water were added. All three vials were stirred at room temperature for 24 h. Each suspension was then centrifuged separately (with filter) to collect Compound 1 Form A.

For methanol/water solutions, approximately 40 mg of Compound 1 was added to a vial. 0.5 ml of methanol and 1 ml of water were added and the suspension was stirred at room temperature for 24 h. The suspension was centrifuged (with filter) to collect Compound 1 Form A.

For acetonitrile, approximately 50 mg of Compound 1 was added to a vial along with 2.0 ml of acetonitrile. The suspension was stirred at room temperature for 24 h and Compound 1 Form A was collected by centrifuge (with filter).

For acetonitrile/water solutions, approximately 50 mg of Compound 1 was dissolved in 2.5 ml of acetonitrile to give a clear solution after sonication. The solution was filtered and 1 ml withdrawn to a vial. 2.25 ml of water was added to give a cloudy suspension. The suspension was stirred at room temperature for 24 h and Compound 1 Form A was collected by centrifuge (with filter).

Slow Evaporation Method

Approximately 55 mg of Compound 1 was dissolved in 0.5 ml of acetone to give a clear solution after sonication. The solution was filtered and 0.2 ml was withdrawn to a vial. The vial was covered with parafilm with one hole poked in it and allowed to stand. Recrystallized Compound 1 Form A was collected by filtering.

Fast Evaporation Method

For isopropyl alcohol, approximately 43 mg of Compound 1 was dissolved in 2.1 ml of isopropyl alcohol to give a clear solution after sonication. The solution was filtered into a vial and allowed to stand uncovered. Recrystallized Compound 1 Form A was collected by filtering.

For methanol, approximately 58 mg of Compound 1 was dissolved in 0.5 ml of methanol to give a clear solution after sonication. The solution was filtered and 0.2 ml was withdrawn to an uncovered vial and allowed to stand. Recrystallized Compound 1 Form A was collected by filtering.

Figure 10:
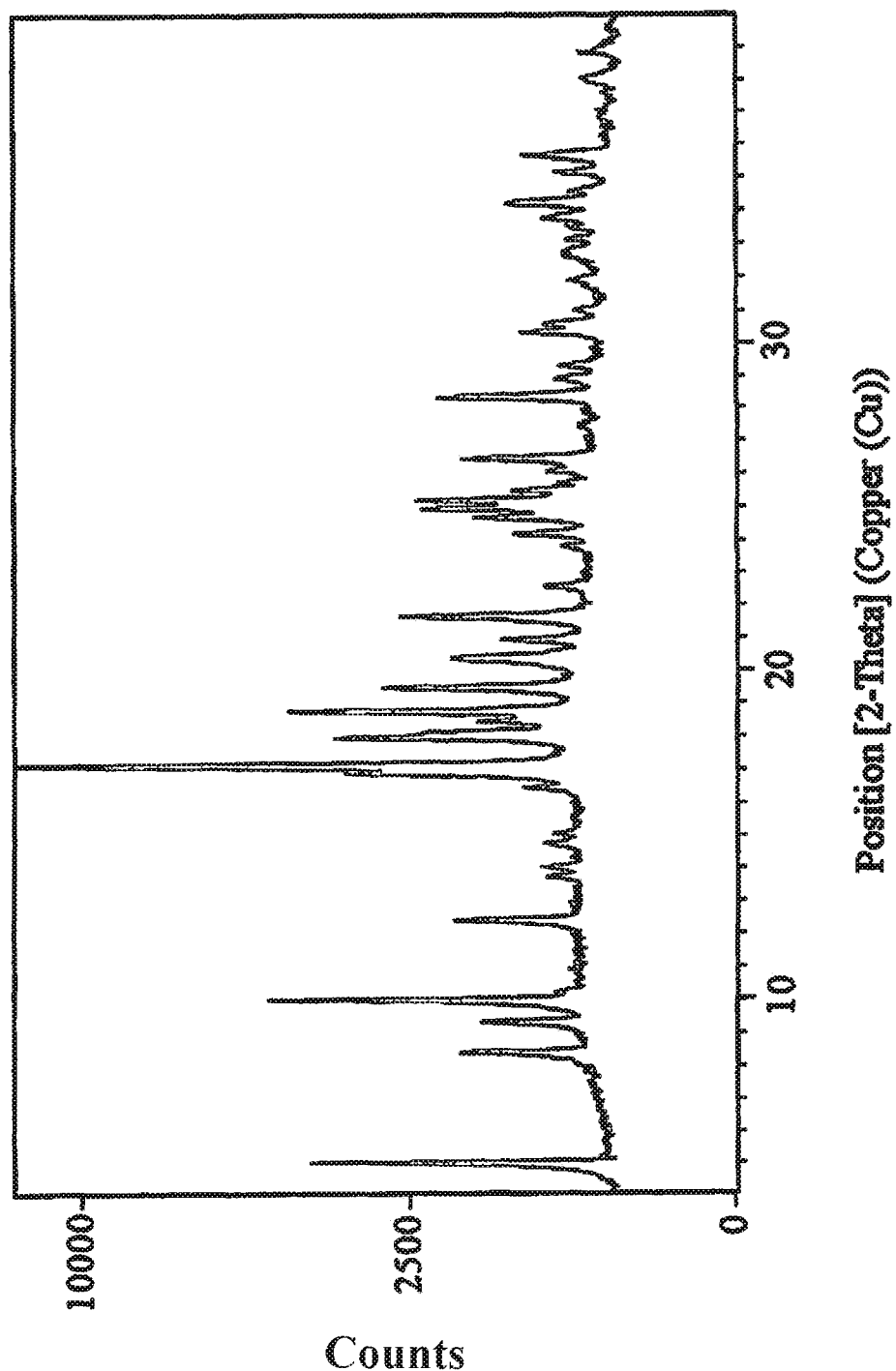
FIG. 10 is an actual X-ray powder diffraction pattern of Compound 1 Form A prepared by the fast evaporation method from acetonitrile.

For acetonitrile, approximately 51 mg of Compound 1 was dissolved in 2.5 ml of acetonitrile to give a clear solution after sonication. The solution was filtered and half the solution was withdrawn to an uncovered vial and allowed to stand. Recrystallized Compound 1 Form A was collected by filtering. FIG. 10 discloses an XRPD pattern of Compound 1 Form A prepared by this method.

Anti-Solvent Method

Figure 11:
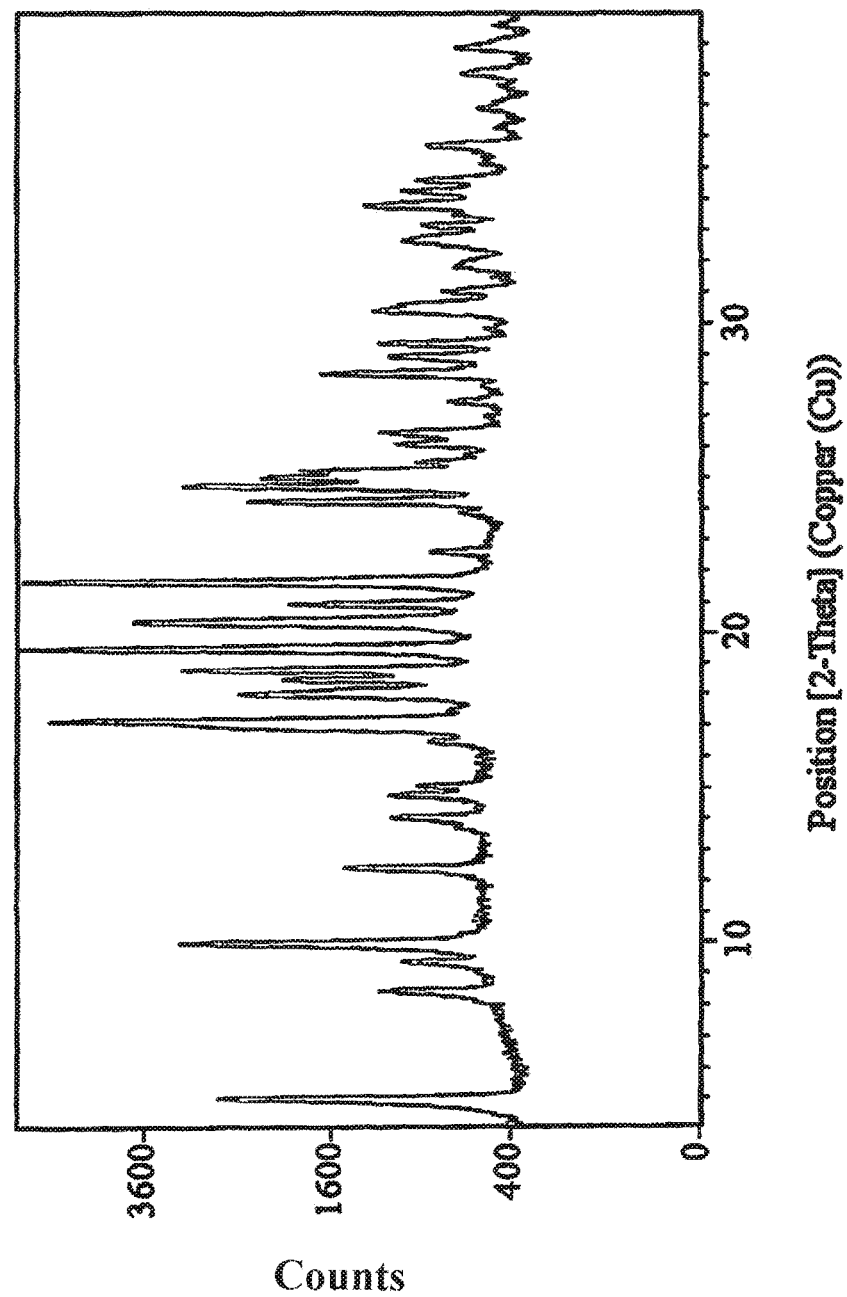
FIG. 11 is an actual X-ray powder diffraction pattern of Compound 1 Form A prepared by the anti solvent method using EtOAc and heptane.

For EtOAc/heptane, approximately 30 mg of Compound 1 was dissolved in 1.5 ml of EtOAc to give a clear solution after sonicating. The solution was filtered and 2.0 ml of heptane was added to the filtered solution while slowly stirring. The solution was stirred for an additional 10 minutes and allowed to stand. Recrystallized Compound 1 Form A was collected by filtering. FIG. 11 discloses an XRPD pattern of Compound 1 Form A prepared by this method.

For isopropyl alcohol/water, approximately 21 mg of Compound 1 was dissolved in 1.0 ml of isopropyl alcohol to give a clear solution after sonicating. The solution was filtered to give 0.8 ml of solution. 1.8 ml of water was added while slowly stirring. An additional 0.2 ml of water was added to give a cloudy suspension. Stirring was stopped for 5 minutes to give a clear solution. The solution was stirred for an additional 2 minutes and allowed to stand. Recrystallized Compound 1 Form A was collected by filtering.

For ethanol/water, approximately 40 mg of Compound 1 was dissolved in 1.0 ml of ethanol to give a clear solution after sonicating. The solution was filtered and 1.0 ml of water was added. The solution was stirred for 1 day at room temperature. Recrystallized Compound 1 Form A was collected by filtering.

For acetone/water, approximately 55 mg of Compound 1 was dissolved in 0.5 ml of acetone to give a clear solution after sonicating. The solution was filtered and 0.2 ml was withdrawn to a vial. 1.5 ml of water was added, and then an additional 0.5 ml of water to give a cloudy suspension. The suspension was stirred for 1 day at room temperature. Compound 1 Form A was collected by filtering.

Table 11 below summarizes the various techniques to form Compound 1 Form A.

TABLE 11

| Vehicle | Re-crystallization method | Results of residue solid |
| --- | --- | --- |
| ACN | Fast Evaporation | Form A |
| Methanol | Fast Evaporation | Form A |
| Ethanol | N/A | N/A |
| IPA | Fast Evaporation | Form A |
| Acetone | Slow Evaporation | Form A |
| EtOAc | Slurry | Form A |
| DCM | Slurry | Form A |
| MTBE | Slurry | Form A |
| Isopropyl acetate | Slurry | Form A |
| Water/Ethanol 1:9 | N/A | N/A |
| Water/Ethanol 1:1 | Slurry | Form A |
| Water/Ethanol 9:1 | Slurry | Form A |
| Water/ACN 9:4 | Slurry | Form A |
| Water/Methanol 2:1 | Slurry | Form A |
| Water/IPA 1:9 | N/A | N/A |
| Water/IPA 9:1 | Slurry | Form A |
| Water/IPA 7:3 | Slurry | Form A |
| Methanol/Water 4:3 | Slurry | Form A |
| EtOAc/Heptane 3:4 | Anti-solvent | Form A |
| IPA/Water 2:5 | Anti-solvent | Form A |
| Ethanol/Water 1:1 | Anti-solvent | Form A |
| Acetone/water 1:10 | Anti-solvent | Form A |
| Ethanol/Water 5:6 | Anti-solvent | N/A |

TABLE 11-continued

| Vehicle | Re-crystallization method | Results of residue solid |
| --- | --- | --- |
| Toluene | N/A | N/A |
| MEK | N/A | N/A |
| Water | N/A | N/A |

Single crystal data were obtained for Compound 1 Form A, providing additional detail about the crystal structure, including lattice size and packing.

Crystal Preparation

Crystals of Compound 1 Form A were obtained by slow evaporation from a concentrated solution of methanol (10 mg/ml). A colorless crystal of Compound 1 Form A with dimensions of 0.20×0.05×0.05 mm was selected, cleaned using mineral oil, mounted on a MicroMount and centered on a Bruker APEXII diffractometer. Three batches of 40 frames separated in reciprocal space were obtained to provide an orientation matrix and initial cell parameters. Final cell parameters were obtained and refined based on the full data set.

Experimental

A diffraction data set of reciprocal space was obtained to a resolution of 0.83 Å using 0.5° steps with 30 s exposure for each frame. Data were collected at room temperature [295 (2) K]. Integration of intensities and refinement of cell parameters were accomplished using APEXII software. Observation of the crystal after data collection showed no signs of decomposition.

TABLE 12

| Crystal data for Compound 1 Form A. | |
| --- | --- |
| $C_{26}H_{27}F_3N_2O_6$ | $F(000) = 1088$ |
| $M_r = 520.50$ | $D_x = 1.397$ Mg m$^{-3}$ |
| Monoclinic, C2 | Cu Kα radiation, λ = 1.54178 Å |
| Hall symbol: C2y | Cell parameters from 3945 reflections |
| a = 21.0952 (16) Å | θ = 2.5° |
| b = 6.6287 (5) Å | μ = 0.97 mm$^{-1}$ |
| c = 17.7917 (15) Å | T = 295K |
| β = 95.867 (6)° | Prism |
| V = 2474.8 (3) Å$^3$ | 0.20 × 0.05 × 0.05 mm |
| Z = 4 | |

Geometry: All esds (except the esd in the dihedral angle between two l.s. planes) are estimated using the full covariance matrix. The cell esds are taken into account individually in the estimation of esds in distances, angles and torsion angles; correlations between esds in cell parameters are only used when they are defined by crystal symmetry. An approximate (isotropic) treatment of cell esds is used for estimating esds involving l.s. planes.

TABLE 13

| Data collection parameters for Compomd 1 Form A crystal. | |
| --- | --- |
| APEX II diffractometer | $R_{int} = 0.027$ |
| Radiation source: fine-focus sealed tube graphite | $θ_{max} = 67.8°, θ_{min} = 2.5°$ |
| | h = −25 → 24 |
| 8766 measured reflections | k = −7 → 7 |
| 3945 independent reflections | l = −19 → 16 |
| 3510 reflections with I > 2σ(I) | |

Data collection: Apex II; cell refinement: Apex II; data reduction: Apex II; program(s) used to solve structure: SHELXS97 (Sheldrick, 1990); program(s) used to refine structure: SHELXL97 (Sheldrick, 1997); molecular graphics: Mercury; software used to prepare material for publication: publCIF.

TABLE 14

| Refinement parameters for Compound 1 Form A crystal. | |
|---|---|
| Refinement on $F^2$ | Hydrogen site location: inferred from neighbouring sites |
| Least-squares matrix: full | H atoms treated by a mixture of independent and constrained refinement |
| $R[F^2 > 2\sigma(F^2)] = 0.043$ | $w = 1/[\sigma^2(F_o^2) + (0.0821P)^2 + 0.2233P]$ where $P = (F_o^2 + 2F_c^2)/3$ |
| $wR(F^2) = 0.119$ | $(\Delta/\sigma)_{max} < 0.001$ |
| $S = 1.05$ | $\Delta\rangle_{max} = 0.14$ e Å$^{-3}$ |
| 3945 reflections | $\Delta\rangle_{min} = -0.13$ e Å$^{-3}$ |
| 443 parameters | Extinction correction: SHELXL, $Fc^* = kFc[1 + 0.001 \times Fc^2\lambda^3/\sin(2\theta)]^{-1/4}$ |
| 1 restraint | Extinction coefficient: 0.00016 (15) |
| 0 constraints | Absolute structure: Flack H D (1983), Acta Cryst. A39, 876-881 |
| Primary atom site location: structure-invariant direct methods | Flack parameter: 0.00 (18) |
| Secondary atom site location: difference Fourier map | |

Refinement: Refinement of $F^2$ against ALL reflections. The weighted R-factor wR and goodness of fit S are based on $F^2$, conventional R-factors R are based on F, with F set to zero for negative $F^2$. The threshold expression of $F^2 > 2\text{sigma}(F^2)$ is used only for calculating R-factors(gt) etc. and is not relevant to the choice of reflections for refinement. R-factors based on $F^2$ are statistically about twice as large as those based on F, and R-factors based on ALL data will be even larger.

Figure 12:
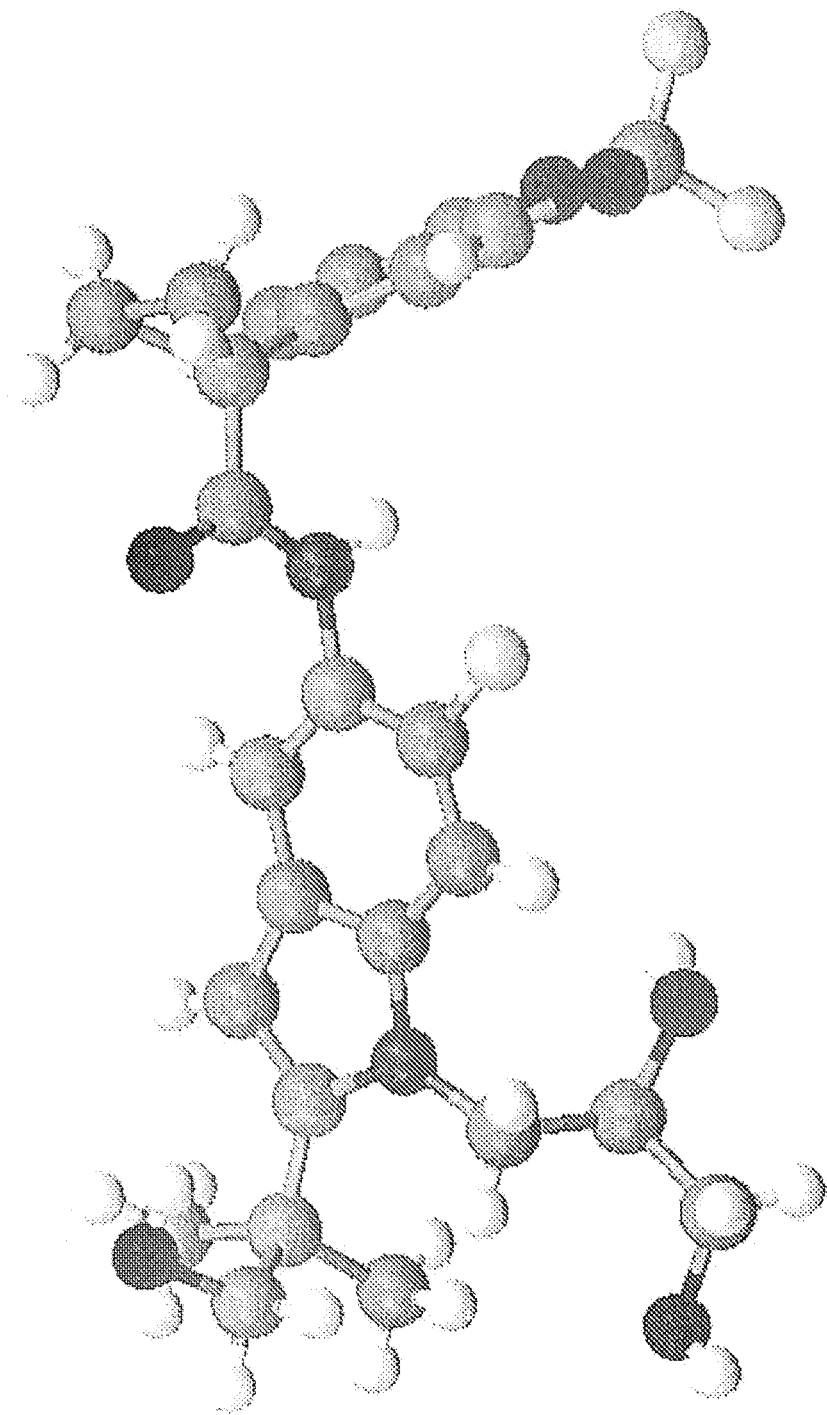
FIG. 12 is a conformational picture of Compound 1 Form A based on single crystal X-ray analysis.

A conformational picture of Compound 1 Form A based on single crystal X-ray analysis is shown in FIG. 12. The crystal structure reveals a dense packing of the molecules. Compound 1 Form A is monoclinic, C2 space group, with the following unit cell dimensions: a=21.0952(16) Å, b=6.6287(5) Å, c=17.7917(15) Å, β=95.867(6)°, γ=90°.

Figure 13:
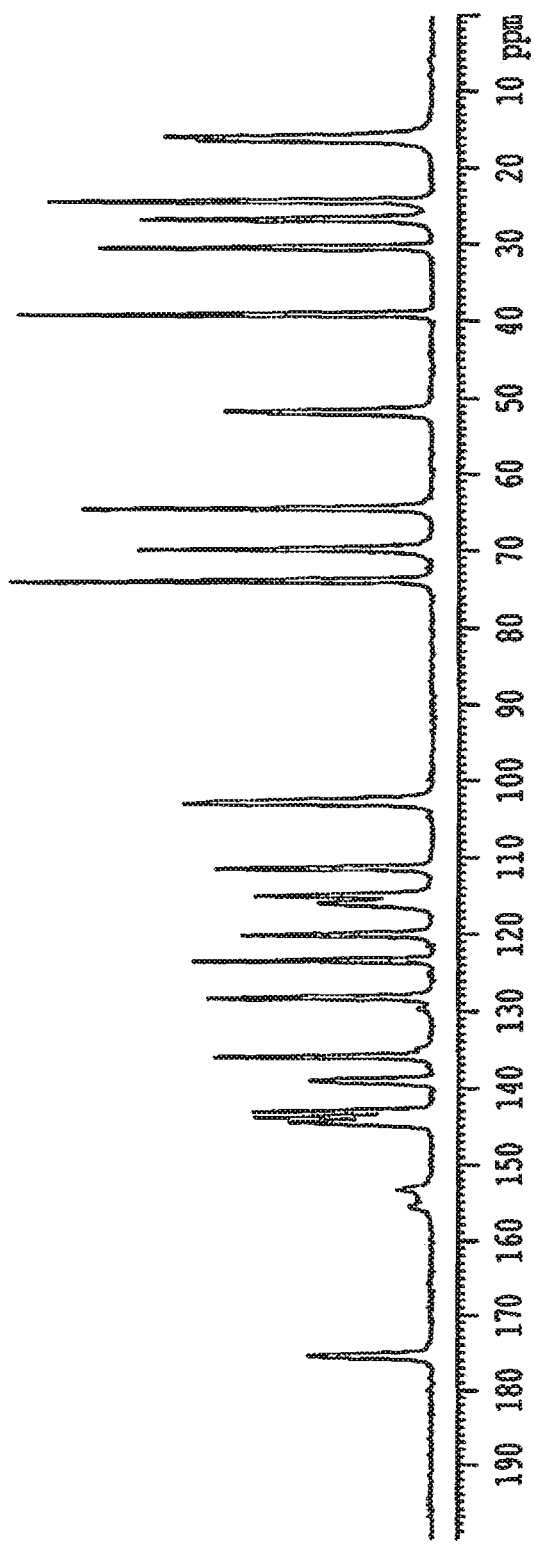
FIG. 13 is a solid state $^{13}$C NMR spectrum (15.0 kHz spinning) of Compound 1 Form A.

A solid state $^{13}$C NMR spectrum of Compound 1 Form A is shown in FIG. 13. Table 15 provides chemical shifts of the relevant peaks.

TABLE 15

| | Compound 1 Form A $^{13}$C Chem. Shifts | |
|---|---|---|
| Peak # | F1 [ppm] | Intensity |
| 1 | 175.3 | 2.9 |
| 2 | 155.4 | 0.54 |
| 3 | 153.3 | 0.81 |
| 4 | 144.3 | 3.35 |
| 5 | 143.7 | 4.16 |
| 6 | 143.0 | 4.24 |
| 7 | 139.0 | 2.86 |
| 8 | 135.8 | 5.19 |
| 9 | 128.2 | 5.39 |
| 10 | 123.3 | 5.68 |
| 11 | 120.0 | 4.55 |
| 12 | 115.8 | 2.66 |
| 13 | 114.9 | 4.2 |
| 14 | 111.3 | 5.17 |
| 15 | 102.8 | 5.93 |
| 16 | 73.8 | 10 |
| 17 | 69.8 | 7.06 |
| 18 | 64.5 | 8.29 |
| 19 | 51.6 | 4.96 |
| 20 | 39.1 | 9.83 |
| 21 | 30.5 | 7.97 |
| 22 | 26.8 | 6.94 |
| 23 | 24.4 | 9.19 |
| 24 | 16.3 | 5.58 |
| 25 | 15.8 | 6.33 |

Figure 14:
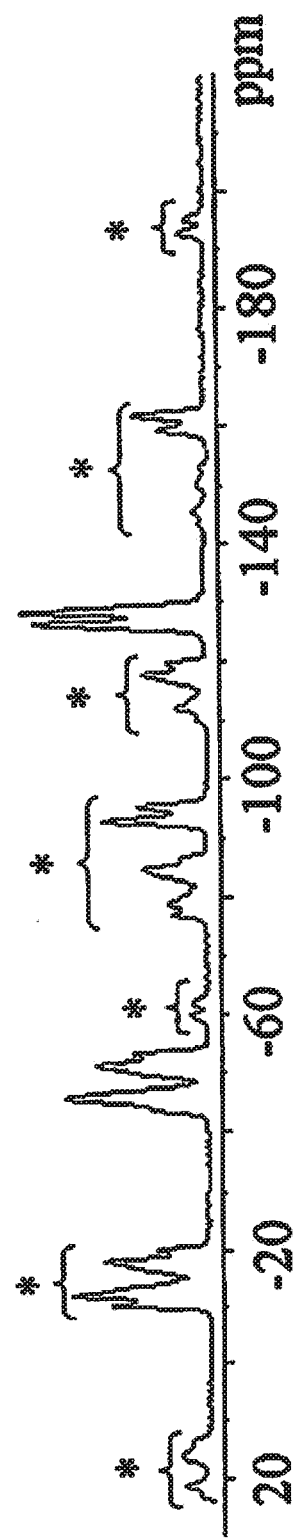
FIG. 14 is a solid state $^{19}$F NMR spectrum (12.5 kHz spinning) of Compound 1 Form A.

A solid state $^{19}$F NMR spectrum of Compound 1 Form A is shown in FIG. 14. Peaks with an asterisk denote spinning side bands. Table 16 provides chemical shifts of the relevant peaks.

TABLE 16

| | Compound 1 Form A $^{19}$F Chem. Shifts | |
|---|---|---|
| Peak # | F1 [ppm] | Intensity |
| 1 | −45.9 | 9.48 |
| 2 | −51.4 | 7.48 |
| 3 | −53.3 | 4.92 |
| 4 | −126.5 | 11.44 |
| 5 | −128.4 | 12.5 |

Exemplary Oral Pharmaceutical Formulations Comprising Compound 1

A tablet is prepared with the components and amounts listed in Tables 17-21.

TABLE 17

| Component | Function | Final Blend Composition % w/w | Tablet (mg/tablet) |
|---|---|---|---|
| 50% Compound 1/ 49.5% HPMCAS-HG/0.5% sodium lauryl sulfate | Active as a spray dried dispersion (SSD) | 50.00 | 10.0 SDD (5.00 Compound 1) |
| Microcrystalline cellulose | Filler | 22.62 | 4.52 |
| Lactose Monohydrate | Filler | 22.63 | 4.53 |
| Crosscarmelose Sodium | Disintegrant | 3.00 | 0.60 |
| Magnesium Stearate | Lubricant | 0.25 | 0.05 |
| Colloidal Silica Dioxide | Glidant | 1.00 | 0.20 |
| | Intragranular content | 99.5 | |
| Extragranular Blend | | | |
| Colloidal Silica Dioxide | Glidant | 0.25 | 0.05 |
| Magnesium Stearate | Lubricant | 0.25 | 0.05 |
| | Extragranular content | 0.5 | |
| Total | | 100.00 | 20.0 |

TABLE 18

| Component | Function | Final Blend Composition % w/w | Tablet (mg/tablet) |
|---|---|---|---|
| 50% Compound 1/ 49.5% HPMCAS-HG/0.5% sodium lauryl sulfate | Active as a spray dried dispersion (SSD) | 9.53 | 20.0 SDD (10.00 Compound 1) |

TABLE 18-continued

| Component | Function | Final Blend Composition % w/w | Tablet (mg/tablet) |
|---|---|---|---|
| Microcrystalline cellulose | Filler | 43.24 | 90.80 |
| Lactose Monohydrate | Filler | 43.24 | 90.80 |
| Crosscarmelose Sodium | Disintegrant | 3.00 | 6.30 |
| Magnesium Stearate | Lubricant | 0.50 | 1.05 |
| Colloidal Silica Dioxide | Glidant | 0.50 | 1.05 |
| Total | | 100.00 | 210.0 |

TABLE 19

| Component | Function | Final Blend Composition % w/w | Tablet (mg/tablet) |
|---|---|---|---|
| 50% Compound 1/ 49.5% HPMCAS-HG/0.5% SLS | Active as a spray dried dispersion (SSD) | 50.00 | 100.0 SDD (50.00 Compound 1) |
| Microcrystalline cellulose (Avicel PH101) | Filler | 22.63 | 45.25 |
| Lactose Monohydrate (Foremost 310) | Filler | 22.63 | 45.25 |
| Crosscarmelose Sodium (AcDiSol) | Disintegrant | 3.00 | 6.0 |
| Magnesium Stearate | Lubricant | 0.25 | 0.5 |
| Colloidal Silica Dioxide (Cabot M5P) | Glidant | 1.00 | 2.0 |
| Intragranular content | | 99.5 | |
| Extragranular Blend | | | |
| Colloidal Silica Dioxide (Cabot M5P) | Glidant | 0.25 | 0.5 |
| Magnesium Stearate | Lubricant Extragranular Content | 0.25 0.5 | 0.5 |
| Total | | 100.00 | 200.0 |

TABLE 20

| Component | Function | Final Blend Composition % w/w | Tablet (mg/tablet) |
|---|---|---|---|
| 50% Compound 1/ 49.5% HPMCAS-HG/0.5% SLS | Active as a spray dried dispersion (SSD) | 50.00 | 200.0 SDD (100.00 Compound 1) |
| Microcrystalline cellulose (Avicel PH101) | Filler | 22.63 | 90.5 |
| Lactose Monohydrate (Foremost 310) | Filler | 22.63 | 90.5 |
| Crosscarmelose Sodium (AcDiSol) | Disintegrant | 3.00 | 12.0 |
| Magnesium Stearate | Lubricant | 0.25 | 1.0 |
| Colloidal Silica Dioxide (Cabot M5P) | Glidant | 1.00 | 4.0 |
| Intragranular content | | 99.5 | |
| Extragranular Blend | | | |
| Colloidal Silica Dioxide (Cabot M5P) | Glidant | 0.25 | 1.0 |
| Magnesium Stearate | Lubricant Extragranular content | 0.25 0.5 | 1.0 |
| Total | | 100.00 | 400.0 |

TABLE 21

| Component | Function | Final Blend Composition % w/w | Tablet (mg/tablet) |
|---|---|---|---|
| 50% Compound 1/ 49.5% HPMCAS-HG/0.5% SLS | Active as a spray dried dispersion (SSD) | 50.00 | 500.0 SDD (250.00 Compound 1) |
| Microcrystalline cellulose (Avicel PH101) | Filler | 22.63 | 226.3 |
| Lactose Monohydrate (Foremost 310) | Filler | 22.63 | 226.3 |
| Crosscarmelose Sodium (AcDiSol) | Disintegrant | 3.00 | 30.0 |
| Magnesium Stearate | Lubricant | 0.25 | 2.5 |
| Colloidal Silica Dioxide (Cabot M5P) | Glidant | 1.00 | 10.0 |
| Intragranular content | | 99.5 | |
| Extragranular Blend | | | |
| Colloidal Silica Dioxide (Cabot M5P) | Glidant | 0.25 | 2.5 |
| Magnesium Stearate | Lubricant Extragranular content | 0.25 0.5 | 2.5 |
| Total | | 100.00 | 1000.0 |

Tablet Formation from Roller Compaction Granule Composition

Equipment/Process

Equipment

| Equipment | Description/Comment |
|---|---|
| Balance(s) (mg to kg scale) | To weigh the powder and individual tablets. |
| Screening and blending equipment | |
| 1. 2-L Turbula T2F Shaker Mixer<br>2. Quadro Comill 197<br>3. hand screen: size #20 US Mesh screen | Delump/blend/lubrication. Prepare blends for dry granulation and tableting. |
| Dry Granulation equipment | |
| 1. Tableting machine: Korsch XL100 rotary tablet press with gravity feed frame ½ inch diameter, round, flat faced tooling | Prepare slugs with 0.72-0.77 solid fraction. |
| Milling | |
| 1. Mortar/pestle<br>2. Quadro co-mill (US/193)<br>3. Fitzpatrick (Fitzmill L1A) | Particle size reduction. |
| Tablet Compression | |
| 1. Tablet machine: Korsch XL100 rotary tablet press with gravity feed frame with 0.2839" × 0.58979" modified oval tooling. | Single tooling press. Tablet manufacture. |

-continued

| Equipment | Description/Comment |
|---|---|
| Other ancillary equipment for determining. | |
| 1. Hardness | |
| 2. Weight sorter | |
| 3. Friability | |
| 4. Deduster | |
| 5. Metal Checker | |

Screening/Weighing

Compound 1 Amorphous Form as the solid spray dried dispersion and Cabot M5P are combined and screened through a 20 mesh screen, and blended in the 2-L Turbula T2F Shaker Mixer for 10 minutes at 32 RPM.

Intragranular Blending

The AcDiSol, Avicel PH101, and Foremost 310 are added and blended for an additional 15 minutes. The blend is then passed through the Quadro Comill 197 (screen: 0.032" R; impeller: 1607; RPM: 1000 RPM). Magnesium stearate is screened with 2-3 times that amount (volume) of the above blend through 20 mesh screen by hand. The resulting mixture is blended in the Turbula mixer for 4 minutes at 32 RPM.

Roller Compaction

Slug the above blend in the Korsch XL 100 rotary tablet press (gravity feed frame ½" diameter, round, flat-faced tooling) to about 0.72-0.77 solid fraction. Calculate solid fraction by measuring the weight, height and using the true density of the material determined during the development. For the rotary tablet press slug process, compression force will vary depending on fill volume of the die and final weight of the slug. Lightly break slugs into roughly ¼ inch pieces with mortar and pestle. Pass the broken slugs through the Quadro Comill 197 (screen: 0.079" G; impeller: 1607; RPM: 1000).

Extragranular Blending

The extragranular Cabot M5P is screened with 2-3 times that amount (volume) of the above blend through a 20 mesh screen by hand. Add this extragranular Cabot M5P pre-blend to the main blend and blend in the 2-L Turbula T2F Shaker Mixer for 15 minutes at 32 RPM. Screen the extragranular magnesium stearate through a 20 mesh screen with 2-3 times that amount (volume) of the above blend by hand. Add this extragranular magnesium stearate pre-blend to the main blend and blend in the Turbular mixer for 4 minutes at 32 RPM.

Compression

Tablets are compressed to target hardness of 14.5±3.5 kp using a Korsch XL 100 with gravity feed frame and 0.289"× 0.5879" modified oval tooling.

Film Coating

Tablets may be film coated using a pan coater, such as, for example an O'Hara Labcoat.

Printing

Film coated tablets may be printed with a monogram on one or both tablet faces with, for example, a Hartnett Delta printer.

Dosing Administration Schedule

In another aspect, the invention relates to a method of treating a CFTR mediated disease in a subject comprising administering to a subject in need thereof an effective amount of the pharmaceutical composition provided by the invention. In another embodiment, the pharmaceutical composition is administered to the subject once every two weeks. In another embodiment, the pharmaceutical composition is administered to the subject once a week. In another embodiment, the pharmaceutical composition is administered to the subject once every three days. In another embodiment, the pharmaceutical composition is administered to the subject once a day. In one embodiment, when the pharmaceutical composition is a tablet according to Table 1, 2, 3, 4, or 5 dosing is once a day.

Assays

Assays for Detecting and Measuring ΔF508-CFTR Correction Properties of Compounds Membrane Potential Optical Methods for Assaying ΔF508-CFTR Modulation Properties of Compounds.

The optical membrane potential assay utilized voltage-sensitive FRET sensors described by Gonzalez and Tsien (See Gonzalez, J. E. and R. Y. Tsien (1995) "Voltage sensing by fluorescence resonance energy transfer in single cells" *Biophys J* 69(4): 1272-80; and Gonzalez, J. E. and R. Y. Tsien (1997) "Improved indicators of cell membrane potential that use fluorescence resonance energy transfer" *Chem Biol* 4(4): 269-77) in combination with instrumentation for measuring fluorescence changes such as the Voltage/Ion Probe Reader (VIPR) (See Gonzalez, J. E., K. Oades, et al. (1999) "Cell-based assays and instrumentation for screening ion-channel targets" *Drug Discov Today* 4(9): 431-439).

These voltage sensitive assays are based on the change in fluorescence resonant energy transfer (FRET) between the membrane-soluble, voltage-sensitive dye, $DiSBAC_2(3)$, and a fluorescent phospholipid, CC2-DMPE, which is attached to the outer leaflet of the plasma membrane and acts as a FRET donor. Changes in membrane potential ($V_m$) cause the negatively charged $DiSBAC_2(3)$ to redistribute across the plasma membrane and the amount of energy transfer from CC2-DMPE changes accordingly. The changes in fluorescence emission were monitored using VIPR™ II, which is an integrated liquid handler and fluorescent detector designed to conduct cell-based screens in 96- or 384-well microtiter plates.

1. Identification of Correction Compounds

To identify small molecules that correct the trafficking defect associated with ΔF508-CFTR; a single-addition HTS assay format was developed. The cells were incubated in serum-free medium for 16 hrs at 37° C. in the presence or absence (negative control) of test compound. As a positive control, cells plated in 384-well plates were incubated for 16 hrs at 27° C. to "temperature-correct" ΔF508-CFTR. The cells were subsequently rinsed 3× with Krebs Ringers solution and loaded with the voltage-sensitive dyes. To activate ΔF508-CFTR, 10 μM forskolin and the CFTR potentiator, genistein (20 μM), were added along with Cl⁻-free medium to each well. The addition of Cl⁻-free medium promoted Cl⁻ efflux in response to ΔF508-CFTR activation and the resulting membrane depolarization was optically monitored using the FRET-based voltage-sensor dyes.

2. Identification of Potentiator Compounds

To identify potentiators of ΔF508-CFTR, a double-addition HTS assay format was developed. During the first addition, a Cl⁻-free medium with or without test compound was added to each well. After 22 sec, a second addition of Cl⁻-free medium containing 2-10 μM forskolin was added to activate ΔF508-CFTR. The extracellular Cl⁻ concentration following both additions was 28 mM, which promoted Cl⁻ efflux in response to ΔF508-CFTR activation and the resulting membrane depolarization was optically monitored using the FRET-based voltage-sensor dyes.

3. Solutions

Bath Solution #1: (in mM) NaCl 160, KCl 4.5, $CaCl_2$ 2, $MgCl_2$ 1, HEPES 10, pH 7.4 with NaOH.

Chloride-free bath solution: Chloride salts in Bath Solution #1 are substituted with gluconate salts.

CC2-DMPE: Prepared as a 10 mM stock solution in DMSO and stored at −20° C. DiSBAC$_2$(3): Prepared as a 10 mM stock in DMSO and stored at −20° C.

4. Cell Culture

NIH3T3 mouse fibroblasts stably expressing ΔF508-CFTR are used for optical measurements of membrane potential. The cells are maintained at 37° C. in 5% CO$_2$ and 90% humidity in Dulbecco's modified Eagle's medium supplemented with 2 mM glutamine, 10% fetal bovine serum, 1×NEAA, β-ME, 1× pen/strep, and 25 mM HEPES in 175 cm$^2$ culture flasks. For all optical assays, the cells were seeded at 30,000/well in 384-well matrigel-coated plates and cultured for 2 hrs at 37° C. before culturing at 27° C. for 24 hrs for the potentiator assay. For the correction assays, the cells are cultured at 27° C. or 37° C. with and without compounds for 16-24 hours.

Electrophysiological Assays for Assaying ΔF508-CFTR Modulation Properties of Compounds 1. Ussing Chamber Assay Using chamber experiments were performed on polarized epithelial cells expressing ΔF508-CFTR to further characterize the ΔF508-CFTR modulators identified in the optical assays. FRT$^{\Delta F508\text{-}CFTR}$ epithelial cells grown on Costar Snapwell cell culture inserts were mounted in an Ussing chamber (Physiologic Instruments, Inc., San Diego, Calif.), and the monolayers were continuously short-circuited using a Voltage-clamp System (Department of Bioengineering, University of Iowa, IA, and, Physiologic Instruments, Inc., San Diego, Calif.). Transepithelial resistance was measured by applying a 2-mV pulse. Under these conditions, the FRT epithelia demonstrated resistances of 4 KΩ/cm$^2$ or more. The solutions were maintained at 27° C. and bubbled with air. The electrode offset potential and fluid resistance were corrected using a cell-free insert. Under these conditions, the current reflects the flow of Cl$^−$ through ΔF508-CFTR expressed in the apical membrane. The I$_{SC}$ was digitally acquired using an MP100A-CE interface and AcqKnowledge software (v3.2.6; BIOPAC Systems, Santa Barbara, Calif.).

2. Identification of Correction Compounds

Typical protocol utilized a basolateral to apical membrane Cl$^−$ concentration gradient. To set up this gradient, normal ringer was used on the basolateral membrane, whereas apical NaCl was replaced by equimolar sodium gluconate (titrated to pH 7.4 with NaOH) to give a large Cl$^−$ concentration gradient across the epithelium. All experiments were performed with intact monolayers. To fully activate ΔF508-CFTR, forskolin (10 μM) and the PDE inhibitor, IBMX (100 μM), were applied followed by the addition of the CFTR potentiator, genistein (50 μM).

As observed in other cell types, incubation at low temperatures of FRT cells stably expressing ΔF508-CFTR increases the functional density of CFTR in the plasma membrane. To determine the activity of correction compounds, the cells were incubated with 10 μM of the test compound for 24 hours at 37° C. and were subsequently washed 3× prior to recording. The cAMP- and genistein-mediated I$_{SC}$ in compound-treated cells was normalized to the 27° C. and 37° C. controls and expressed as percentage activity. Preincubation of the cells with the correction compound significantly increased the cAMP- and genistein-mediated I$_{SC}$ compared to the 37° C. controls.

3. Identification of Potentiator Compounds

Typical protocol utilized a basolateral to apical membrane Cl$^−$ concentration gradient. To set up this gradient, normal ringers was used on the basolateral membrane and was permeabilized with nystatin (360 μg/ml), whereas apical NaCl was replaced by equimolar sodium gluconate (titrated to pH 7.4 with NaOH) to give a large Cl$^−$ concentration gradient across the epithelium. All experiments were performed 30 min after nystatin permeabilization. Forskolin (10 μM) and all test compounds were added to both sides of the cell culture inserts. The efficacy of the putative ΔF508-CFTR potentiators was compared to that of the known potentiator, genistein.

4. Solutions

Basolateral solution (in mM): NaCl (135), CaCl$_2$ (1.2), MgCl$_2$ (1.2), K$_2$HPO$_4$ (2.4), KHPO$_4$ (0.6), N-2-hydroxyethylpiperazine-N'-2-ethanesulfonic acid (HEPES) (10), and dextrose (10). The solution was titrated to pH 7.4 with NaOH.

Apical solution (in mM): Same as basolateral solution with NaCl replaced with Na Gluconate (135).

5. Cell Culture

Fisher rat epithelial (FRT) cells expressing ΔF508-CFTR (FRT$^{\Delta F508\text{-}CFTR}$) were used for Ussing chamber experiments for the putative ΔF508-CFTR modulators identified from our optical assays. The cells were cultured on Costar Snapwell cell culture inserts and cultured for five days at 37° C. and 5% CO$_2$ in Coon's modified Ham's F-12 medium supplemented with 5% fetal calf serum, 100 U/ml penicillin, and 100 μg/ml streptomycin. Prior to use for characterizing the potentiator activity of compounds, the cells were incubated at 27° C. for 16-48 hrs to correct for the ΔF508-CFTR. To determine the activity of corrections compounds, the cells were incubated at 27° C. or 37° C. with and without the compounds for 24 hours.

6. Whole-Cell Recordings

The macroscopic ΔF508-CFTR current (I$_{\Delta F508}$) in temperature- and test compound-corrected NIH3T3 cells stably expressing ΔF508-CFTR were monitored using the perforated-patch, whole-cell recording. Briefly, voltage-clamp recordings of I$_{\Delta F508}$ were performed at room temperature using an Axopatch 200B patch-clamp amplifier (Axon Instruments Inc., Foster City, Calif.). All recordings were acquired at a sampling frequency of 10 kHz and low-pass filtered at 1 kHz. Pipettes had a resistance of 5-6 MΩ when filled with the intracellular solution. Under these recording conditions, the calculated reversal potential for Cl$^−$ (E$_{Cl}$) at room temperature was −28 mV. All recordings had a seal resistance >20 GΩ and a series resistance <15 MΩ. Pulse generation, data acquisition, and analysis were performed using a PC equipped with a Digidata 1320 A/D interface in conjunction with Clampex 8 (Axon Instruments Inc.). The bath contained <250 μl of saline and was continuously perifused at a rate of 2 ml/min using a gravity-driven perfusion system, 7. Identification of Correction Compounds To determine the activity of correction compounds for increasing the density of functional ΔF508-CFTR in the plasma membrane, we used the above-described perforated-patch-recording techniques to measure the current density following 24-hr treatment with the correction compounds. To fully activate ΔF508-CFTR, 10 μM forskolin and 20 μM genistein were added to the cells. Under our recording conditions, the current density following 24-hr incubation at 27° C. was higher than that observed following 24-hr incubation at 37° C. These results are consistent with the known effects of low-temperature incubation on the density of ΔF508-CFTR in the plasma membrane. To determine the effects of correction compounds on CFTR current density, the cells were incubated with 10 μM of the test compound for 24 hours at 37° C. and the current density was compared to the 27° C. and 37° C. controls (% activity). Prior to recording, the cells were washed 3× with extracellular recording medium to remove any remaining test compound. Preincubation with 10 µM of correction compounds significantly increased the cAMP- and genistein-dependent current compared to the 37° C. controls.

8. Identification of Potentiator Compounds

The ability of ΔF508-CFTR potentiators to increase the macroscopic ΔF508-CFTR Cl⁻ current ($I_{\Delta F508}$) in NIH3T3 cells stably expressing ΔF508-CFTR was also investigated using perforated-patch-recording techniques. The potentiators identified from the optical assays evoked a dose-dependent increase in $I_{\Delta F508}$ with similar potency and efficacy observed in the optical assays. In all cells examined, the reversal potential before and during potentiator application was around −30 mV, which is the calculated $E_{Cl}$ (−28 mV).

9. Solutions

Intracellular solution (in mM): Cs-aspartate (90), CsCl (50), MgCl$_2$ (1), HEPES (10), and 240 µg/ml amphotericin-B (pH adjusted to 7.35 with CsOH).

Extracellular solution (in mM): N-methyl-D-glucamine (NMDG)-Cl (150), MgCl$_2$ (2), CaCl$_2$ (2), HEPES (10) (pH adjusted to 7.35 with HCl).

10. Cell Culture

NIH3T3 mouse fibroblasts stably expressing ΔF508-CFTR are used for whole-cell recordings. The cells are maintained at 37° C. in 5% CO$_2$ and 90% humidity in Dulbecco's modified Eagle's medium supplemented with 2 mM glutamine, 10% fetal bovine serum, 1×NEAA, β-ME, 1× pen/strep, and 25 mM HEPES in 175 cm² culture flasks. For whole-cell recordings, 2,500-5,000 cells were seeded on poly-L-lysine-coated glass coverslips and cultured for 24-48 hrs at 27° C. before use to test the activity of potentiators; and incubated with or without the correction compound at 37° C. for measuring the activity of correctors.

11. Single-Channel Recordings

The single-channel activities of temperature-corrected ΔF508-CFTR stably expressed in NIH3T3 cells and activities of potentiator compounds were observed using excised inside-out membrane patch. Briefly, voltage-clamp recordings of single-channel activity were performed at room temperature with an Axopatch 200B patch-clamp amplifier (Axon Instruments Inc.). All recordings were acquired at a sampling frequency of 10 kHz and low-pass filtered at 400 Hz. Patch pipettes were fabricated from Corning Kovar Sealing #7052 glass (World Precision Instruments, Inc., Sarasota, Fla.) and had a resistance of 5-8 MΩ when filled with the extracellular solution. The ΔF508-CFTR was activated after excision, by adding 1 mM Mg-ATP, and 75 nM of the cAMP-dependent protein kinase, catalytic subunit (PKA; Promega Corp. Madison, Wis.). After channel activity stabilized, the patch was perifused using a gravity-driven microperfusion system. The inflow was placed adjacent to the patch, resulting in complete solution exchange within 1-2 sec. To maintain ΔF508-CFTR activity during the rapid perifusion, the nonspecific phosphatase inhibitor F⁻ (10 mM NaF) was added to the bath solution. Under these recording conditions, channel activity remained constant throughout the duration of the patch recording (up to 60 min). Currents produced by positive charge moving from the intra- to extracellular solutions (anions moving in the opposite direction) are shown as positive currents. The pipette potential ($V_p$) was maintained at 80 mV.

Channel activity was analyzed from membrane patches containing <2 active channels. The maximum number of simultaneous openings determined the number of active channels during the course of an experiment. To determine the single-channel current amplitude, the data recorded from 120 sec of ΔF508-CFTR activity was filtered "off-line" at 100 Hz and then used to construct all-point amplitude histograms that were fitted with multigaussian functions using Bio-Patch Analysis software (Bio-Logic Comp. France). The total microscopic current and open probability ($P_o$) were determined from 120 sec of channel activity. The $P_o$ was determined using the Bio-Patch software or from the relationship $P_o=I/i(N)$, where I=mean current, i=single-channel current amplitude, and N=number of active channels in patch.

12. Solutions

Extracellular solution (in mM): NMDG (150), aspartic acid (150), CaCl$_2$ (5), MgCl$_2$ (2), and HEPES (10) (pH adjusted to 7.35 with Tris base).

Intracellular solution (in mM): NMDG-Cl (150), MgCl$_2$ (2), EGTA (5), TES (10), and Tris base (14) (pH adjusted to 7.35 with HCl).

13. Cell Culture

NIH3T3 mouse fibroblasts stably expressing ΔF508-CFTR are used for excised-membrane patch-clamp recordings. The cells are maintained at 37° C. in 5% CO$_2$ and 90% humidity in Dulbecco's modified Eagle's medium supplemented with 2 mM glutamine, 10% fetal bovine serum, 1×NEAA, β-ME, 1× pen/strep, and 25 mM HEPES in 175 cm² culture flasks. For single channel recordings, 2,500-5,000 cells were seeded on poly-L-lysine-coated glass coverslips and cultured for 24-48 hrs at 27° C. before use.

Using the procedures described above, the activity, i.e., EC50s, of Compound 1 has been measured and is shown in Table 22.

TABLE 22

| IC50/EC50 Bins: +++ <= 2.0 µL < ++ <= 5.0 µL < + | | |
| PercentActivity Bins: + <= 25.0 < ++ <= 100.0 < +++ | | |
|---|---|---|
| Cmpd. No. | BinnedEC50 | BinnedMaxEfficacy |
| 1 | +++ | +++ |

OTHER EMBODIMENTS

All publications and patents referred to in this disclosure are incorporated herein by reference to the same extent as if each individual publication or patent application were specifically and individually indicated to be incorporated by reference. Should the meaning of the terms in any of the patents or publications incorporated by reference conflict with the meaning of the terms used in this disclosure, the meaning of the terms in this disclosure are intended to be controlling. Furthermore, the foregoing discussion discloses and describes merely exemplary embodiments of the invention. One skilled in the art will readily recognize from such discussion and from the accompanying drawings and claims, that various changes, modifications and variations can be made therein without departing from the spirit and scope of the invention as defined in the following claims.

We claim:

1. A method for treating cystic fibrosis in a patient, comprising coadministering:
   a) a pharmaceutical composition comprising 5 to 250 mg of (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide (Compound 1) and a pharmaceutically acceptable carrier, wherein Compound 1 is in a spray dried dispersion; and
b) another pharmaceutical composition comprising 100 to 300 mg N-(5-hydroxy-2,4-ditert-butyl-phenyl)-4-oxo-1H-quinoline-3-carboxamide (Compound 2) and a pharmaceutically acceptable carrier;
wherein the patient has a ΔF508 or G551D cystic fibrosis transmembrane conductance regulator (CFTR) gene mutation and a second CFTR gene mutation selected from R117H, A455E, 2789+5G→A, and 3849+10kbC→T;
wherein the pharmaceutical composition of step (a) is administered concurrently with the pharmaceutical composition of step (b).

2. The method of claim 1, wherein Compound 1 is substantially amorphous, wherein less than 15% of Compound 1 is in crystalline form.

3. The method of claim 2, wherein less than 10% of Compound 1 is in crystalline form.

4. The method of claim 3, wherein less than 5% of Compound 1 is in crystalline form.

5. The method of claim 4, wherein less than 1% of Compound 1 is in crystalline form.

6. The method of claim 1, wherein Compound 1 is present in an amount of about 100 mg.

7. The method of claim 1, wherein the pharmaceutical composition of step (a) and the pharmaceutical composition of step (b) are administered once a day.

8. The method of claim 1, wherein 150 mg of Compound 2 is administered.

9. The method of claim 1, wherein the method comprises administering an additional therapeutic agent.

10. The method of claim 9, wherein the additional therapeutic agent is a mucolytic agent, bronchodilator, an antibiotic, an anti-infective agent, an anti-inflammatory agent, a CFTR modulator other than Compound 2, or a nutritional agent.

11. The method of claim 9, wherein the additional therapeutic agent is a CFTR modulator other than Compound 2.

12. The method of claim 1, wherein the second CFTR gene mutation is A455E.

13. The method of claim 1, wherein the second CFTR gene mutation is 2789+5G→A.

14. The method of claim 1, wherein the second CFTR gene mutation is 3849+10kbC→T.

* * * * *